(12) United States Patent
Chevrier et al.

(10) Patent No.: US 11,285,100 B2
(45) Date of Patent: *Mar. 29, 2022

(54) FREEZE-DRIED POLYMER COMPOSITIONS FOR MIXING WITH PLATELET RICH PLASMA TO FORM IMPLANTS FOR TISSUE REPAIR AND/OR COMPOSITIONS FOR THERAPEUTIC INTRA-ARTICULAR INJECTIONS

(71) Applicant: ORTHO REGENERATIVE TECHNOLOGIES INC., Kirkland (CA)

(72) Inventors: Anik Chevrier, Point-Claire (CA); Michael D. Buschmann, Montreal (CA); Daniel Veilleux, Montreal (CA); Caroline Hoemann, Montreal (CA); Marc Lavertu, Point-Claire (CA)

(73) Assignee: Ortho Regenerative Technologies Inc., Kirkland (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/119,397

(22) PCT Filed: Feb. 20, 2015

(86) PCT No.: PCT/CA2015/050129
§ 371 (c)(1),
(2) Date: Aug. 17, 2016

(87) PCT Pub. No.: WO2015/123778
PCT Pub. Date: Aug. 27, 2015

(65) Prior Publication Data
US 2017/0049696 A1  Feb. 23, 2017

Related U.S. Application Data

(60) Provisional application No. 61/942,544, filed on Feb. 20, 2014.

(51) Int. Cl.
| | | |
|---|---|---|
| *A61K 9/00* | (2006.01) | |
| *A61K 9/19* | (2006.01) | |
| *A61L 27/20* | (2006.01) | |
| *A61K 35/16* | (2015.01) | |
| *A61K 33/14* | (2006.01) | |
| *A61L 27/36* | (2006.01) | |
| *A61L 27/54* | (2006.01) | |
| *A61K 35/19* | (2015.01) | |
| *C08J 3/12* | (2006.01) | |
| *C08B 37/08* | (2006.01) | |
| *C08L 5/08* | (2006.01) | |
| *A61K 33/42* | (2006.01) | |
| *A61K 47/36* | (2006.01) | |
| *A61K 31/722* | (2006.01) | |
| *A61K 45/06* | (2006.01) | |
| *A61K 33/10* | (2006.01) | |
| *A61K 33/06* | (2006.01) | |

(Continued)

(52) U.S. Cl.
CPC .............. *A61K 9/0024* (2013.01); *A61K 9/19* (2013.01); *A61K 31/722* (2013.01); *A61K 33/06* (2013.01); *A61K 33/10* (2013.01); *A61K 33/14* (2013.01); *A61K 33/42* (2013.01); *A61K 35/16* (2013.01); *A61K 35/19* (2013.01); *A61K 45/06* (2013.01); *A61K 47/36* (2013.01); *A61L 27/20* (2013.01); *A61L 27/3616* (2013.01); *A61L 27/54* (2013.01); *C08B 37/003* (2013.01); *C08J 3/12* (2013.01); *C08J 3/21* (2013.01); *C08L 5/08* (2013.01); *A61K 47/26* (2013.01); *A61L 2400/06* (2013.01); *A61L 2430/24* (2013.01); *C08J 2305/08* (2013.01)

(58) Field of Classification Search
CPC ...... A61K 9/0024; A61K 9/19; A61K 31/722; A61L 27/54; A61L 27/3616; A61L 2400/06; A61L 2430/24
See application file for complete search history.

(56) References Cited

U.S. PATENT DOCUMENTS

| | | | | |
|---|---|---|---|---|
| 6,896,809 B2 * | 5/2005 | Qian | ..................... | C08B 37/003 210/638 |
| 8,258,117 B2 * | 9/2012 | Hoemann | ............ | A61K 31/727 424/529 |
| 8,945,609 B2 | 2/2015 | Schuetz et al. | | |

(Continued)

FOREIGN PATENT DOCUMENTS

| | | |
|---|---|---|
| CA | 2729923 A1 | 1/2009 |
| JP | 2009-520705 | 5/2009 |

(Continued)

OTHER PUBLICATIONS

Hafner et al. Short- and Long-Term Stability of Lyophilized Melatonin-Loaded Lecithin/Chitosan Nanoparticles; Chemical and Pharmaceutical Bulletin, vol. 59, No. 9 (2011) pp. 1117-1123.*
Santagapita et al. Effect of the Composition, PH and Type of Drying on Enzyme Release From Dried and Wet Polyelectrode Capsules; Frontiers in Water Biophysics Conference, Abstract, pp. 1 (Year: 2010).*

(Continued)

*Primary Examiner* — Susan M Hanley
*Assistant Examiner* — Paul C Martin
(74) *Attorney, Agent, or Firm* — Eric L. Lane; Green Patent Law

(57) ABSTRACT

The present application relates to a freeze-dried polymer composition containing chitosan and at least one lyoprotectant, a process for preparing a freeze-dried composition containing chitosan and at least one lyoprotectant and the use of a reconstituted freeze-dried chitosan composition to prepare implants for tissue repair.

25 Claims, 26 Drawing Sheets

(51) Int. Cl.
C08J 3/21 (2006.01)
A61K 47/26 (2006.01)

(56) References Cited

U.S. PATENT DOCUMENTS

2009/0004230 A1  1/2009  Chuetz et al.
2014/0324169 A1* 10/2014  Maher ............... A61F 2/30756
                                                  623/14.12

FOREIGN PATENT DOCUMENTS

WO    WO 2008/064487 A1    6/2008
WO    WO 2011/060555 A1    5/2011

OTHER PUBLICATIONS

Luca et al. Injectable RHBMP-2-Loaded Chitosan Hydrogel Composite: Osteoinduction at Ectopic Site and in Segmental Long Bone Defect; Journal of Biomedical Materials, vol. 96, No. 1, pp. 66-74. (Year: 2010).*
Zhou et al. Effect of Molecular Weight and Degree of Chitosan Deacetylation on the Preparation and Characteristics of Chitosan Thermosensitive Hydrogel as a Delivery System; Carbohydrate Polymers, vol. 73, pp. 265-273. (Year: 2008).*
Fernandez et al. Preparation and Characterization of Chitosan Gels; Journal of the Chilean Chemical Society, vol. 51, No. 4, pp. 1-7. (Year: 2006).*
Katas et al. Storage Stabilization of Albumin-Loaded Chitosan Nanoparticles by Lyoprotectants; Tropical Journal of Pharmaceutical Research, vol. 12, No. 2, pp. 135-142. (Year: 2013).*
Dounighi et al. Preparation and in Vitro Characterization of Chitosan Nanoparticles Containing *Mesobuthus eupeus* Scorpion Venum as an Antigen Delivery System; The Journal of Animals and Toxins including Tropical Diseases, vol. 18, No. 1, pp. 44-52. (Year: 2012).*
Ayensu et al. Development and Evaluation of Lyophilized Thiolated-Chitosan Wafers for Buccal Delivery of Protein; Journal of Science and TEchnology, vol. 32, No. 2 pp. 46-55. (Year: 2012).*
Anonymous. BSA Solution (0.1%), Recipe, Cold Spring Harbor Protocols, downloaded from http://www.cshprptocols.cshlp.org/content/2008/11/pdb.rec11503.full on Jul. 21, 2021. (Year: 2008).*
Kurita, K. Chitin and Chitosan: Functional Biopolymers From Marine Crustaceans; Marine Biotechnology, vol. 8, pp. 203-226. (Year: 2006).*
Patois, E. et al. "Novel thermosensitive chitosan hydrogels: in vivo evaluation" J. Biomed. Mater. Res. A Nov. 2009, vol. 91 (No. 2), pp. 324-330.
Rampino, A. et al. "Chitosan nanoparticles: preparation, size evolution and stability" Int. J. Pharm. Oct. 15, 2013, vol. 455 (No. 1-2), pp. 219-228.
Vandana, M. et al. "Optimization of physiochemical parameters influencing the fabrication of protein-loaded chitosan nanoparticles" Nanomedicine Oct. 2009, vol. 4 (No. 7).
International Search Report and Written Opnion dated Jun. 15, 2015 in related International Application No. PCT/CA2015/050129.
Patel et al., Treatment With Platelet-Rich Plasma is More Effective Than Placebo for Knee Osteoarthritis, 2013.
Patois et al., Novel thermosensitive chitosan hydrogels: In vivo evaluation, 2008.
Petrera et al., Supplementation With Platelet-Rich Plasma Improves the in Vitro Formation of Tissue-Engineered Cartilage With Enhanced Mechanical Properties, 2013.
Petterson et al., Human articular chondrocytes on macroporous gelatin m icrocarriers form structurally stable constructs with blood-derived biotigicat glues in vitro, 2009.
Qi et al., Local Delivery of Autologous Platelet in Collagen Matrix Synergistically Stimulated in-situ Articular Cartilage Repair, 2009.
Qi et al., Local Delivery of Autologous Platelet in Collagen Matrix Simulated in Situ Articular Cartilage Repair, 2009.
Rossi et al., Wound Dressings Based on Chitosans and Hyaluronic Acid for the Release of Chlorhexidine Diacetate in Skin Ulcer Therapy, 2007.
Rossi et al., "Sponge-like" dressings based on biopolymers for the delivery of platelet lysate to skin chronic wounds, 2013.
Saito et al., Intraarticular administration of platelet-rich plasma withbiodegradable gelatin hydrogel microspheres prevents osteoarthritis progression in the rabbit knee,2009.
Sanchez et al., Intra-articular injection of an autologous preparation rich in growth factors for the treatment of knee OA: a retrospective cohort study, 2008.
Van Buul et al., Platelet-Rich Plasma Releasate Inhibits Inflammatory Processes in Osteoarthritic Ghondrocytes, 2011.
Wang et al., Sugar-mediated chitosan/poly(ethylene glycol)-dicalcium pyrophosphate composite: Mechanical and microstructural properties, 2003a.
Wang et al., Effects of Hylan G-F 20 supplementation oncartilage preservation . . . , BMC Musculoskeletal Disorders, 2011.
Wang-Saegusa et al., InWltration of plasma rich in growth factors for osteoarthritis of the knee short-term eVects on function and quality of life, Orthopaedic Surgery, 2011.
Wedmore et al., A Special Report on the Chitosan-based Hemostatic Dressing: Experience in Current Combat Operations, The Journal of TRAUMA Injury, 2006.
Wu et al., Autologous Injectable Tissue-Engineered Cartilage by Using Platelet-Rich Plasma: Experimental Study in a Rabbit Model, 2007.
Wu et al., Platelet-rich plasma—A promising cell carrier for microinvasive articular cartilage repair, 2009.
Wu et al., Regenerative potentials of platelet-rich plasma enhanced by collagen in retrieving pro-inflammatory cytokine-inhibited chondrogenesis, 2011.
Xie et al., Comparative evaluation of MSCs from bone marrow and adipose tissue seeded in PRP-derived scaffold for cartilage regeneration, 2012.
Yeo et al., The Effects of PVA/Chitosan/Fibroin (PCF)-Blended Spongy Sheets on Wound Healing in Rats, 2000.
Milano et al., The Effect Ofautologous Conditioned Plasma on the Treatment of Focal Chondral Defects of the Knee. An Experimental Study, 2011.
Mishra et al., Buffered Platelet-Rich Plasma Enhances Mesenchymal Stem Cell Proliferation and Chondrogenic Differentiation, 2009.
Napolitano et al., Autologous platelet gel for tissue regeneration in degenerative disorders of the knee, 2012.
Nettles et al., Potential Use of Chitosan as a Cell Scaffold Material for Cartilage Tissue Engineering, 2002.
Nguyen et al., Improved reproducibility in the determination of the molecular weight of chitosan by analytical size exclusion chromatography, 2009.
Noel et al., Efficacy and safety of Hylan G-F 20 in shoulder osteoarthritis with an intact rotator cuff. Open-label prospective multicenter study, 2009.
Ong et al., Development of a chitosan-based wound dressing with improved hemostatic and antimicrobial properties, 2008.
Park et al., Time-sequential modulation in expression of growth factors from platelet-rich plasma (PRP) on the chondrocyte cultures, 2012.
Cho et al., Evaluation of protein stability and in vitro permeation of lyophilized polysaccharides-based microparticles for intranasal protein delivery, 2011.
Concaro et al., Effect of cell seeding concentration on the quality of tissue engineered constructs loaded with adult human articular chondrocytes, 2008.
Conrozier et al., Prospective, multi-centre, randomised evaluation of the safety and efficacy.., Arch Orthop Trauma Surg (2009) 129:417-423, 2009.
Costa-Pinto et al., Scaffolds Based Bone Tissue Engineering: The Role of Chitosan, Tissue Engineering: Part B, 2011.
Cox et al., New hemostatic agents in the combat setting, 2009.
Dai et al., Chitosan Acetate Bandage as a Topical Antimicrobial Dressing for Infected Burns, 2008.

(56) References Cited

OTHER PUBLICATIONS

Del Fante et al., Platelet Lysate Mucohadesive Formulation to Treat Oral Mucositis in Graft Versus Host Disease Patients: A New Therapeutic Approach, 2011.
Devlin et al., Comparison of ChitoFlex®, Celox™, and QuikClot® in Control of Hemorrhage, The Journal of Emergency Medicine, vol. 41, No. 3, pp. 237-245, 2011.
Drengk et al., Influence of Platelet-Rich Plasma on Chondrogenic Differentiation and Proliferation of Chondrocytes and Mesenchymal Stem Cells, 2009.
Ezoddini-Ardakani et al., Histologic evaluation of chitosan as an accelerator of bone regeneration in microdrilled rat tibias, Dent Res J (Isfahan). Nov.-Dec. 2012; 9(6).
Arnaud et al., "Comparison of 10 hemostatic dressings in a groin puncture model in swine," J Vasc. Surgery, vol. 50 No. 3 (2009).
Ayensu et al., "Development and physico-mechanical characterisation of lyophilised chitosan wafers . . . ", Colloids and Surfaces B: Biointerfaces 91 (2012) 258-265.
Ayensu et al., "In vitro characterisation of chitosan based xerogels for potential buccal delivery of proteins", Carbohydrate Polymers 89 (2012) 935-941.
Bendinelli et al., "Molecular Basis of Anti-Inflammatory Action of Platelet-Rich Plasma on Human Chondrocytes", Journal of Cellular Physiology (2010).
Betsch et al., "Bone Marrow Aspiration Concentrate and Platelet Rich Plasma for Osteochondral Repair in a PorcineOsteochondral Defect Model", Aug. 2013, vol. 8.
Bi et al., Reconstruction of goat tibial defects using an injectable tricalcium phosphate/ chitosan in combination with autologous platelet-rich plasma, 2010.
Brown et al., Experience With Chitosan Dressings in a Civilian EMS System, The Journal of Emergency Medicine, vol. 37, No. 1, pp. 1-7, 2009.
Burkatovskaya et al., Use of chitosan bandage to prevent fatal infections developing from highly contaminated wounds in mice, Biomaterials 27 (2006) 4157-4164.
Burkatovskaya et al., Effect of chitosan acetate bandage on wound healing in infected and noninfected wounds in mice, Wound Repair and Regeneration, 2008.
Chen et al., Composite chondroitin-6-sulfate/dermatan sulfate/chitosan scaffolds for cartilage tissue engineering, Biomaterials 28 (2007) 2294-2305.
Lee et al., Platelet-rich plasma loaded hydrogel scaffold enhances chondrogenic differentiation and maturation with up-regulation of CB1 and CB2, 2012.
Li et al., Chitosan-alginate as scaffolding material for cartilage tissue engineering, 2005.
Li et al., Preparation and evaluation of thiolated chitosan scaffolds for tissue engineering, 2010.
Lippross et al., Intraarticular Injection of Platelet-Rich Plasma Reduces Inflammation in a Pig Model of Rheumatoid Arthritis of the Knee Joint, 2013.
Littlejohn et al., Comparison of Celox-A, ChitoFlex, WoundStat, and Combat Gauze Hemostatic Agents Versus Standard Gauze Dressing . . . , 2011.
Lopez-Vidriero et al., The Use of Platelet-Rich Plasma in Arthroscopy and Sports Medicine: Optimizing the Healing Environment, 2010.
Ma et al., A preliminary in vitro study on the fabrication and tissue engineering applications of a novel chitosan bilayer material . . . , 2001.
Marmotti et al., One-step osteochondral repair with cartilage fragments in a composite scaffold, 2012.
Martel-Estrada et al., In vitro bioactivity of chitosan/poly (D,L-lactide-co-glycolide) composites, 2011.
Milano et al., The effect of platelet rich plasma combined with microfractures on the treatment of chondral defects: an experimental study in a sheep model, 2010.
Filardo et al., Platelet-rich plasma intra-articular knee injections for the treatment of degenerative cartilage lesions and osteoarthritis, 2011.
Fortier et al., The Effects of Platelet-Rich Plasma on Cartilage: Basic Science and Clinical Application, 2011.
Gobbi et al., Platelet-Rich Plasma Treatment in Symptomatic Patients With Knee Osteoarthritis, 2012.
Gong et al., Use of synovium-derived stromal cells and chitosan/collagen type I scaffolds for cartilage tissue engineering, 2010.
Granville-Chapman et al., Pre-hospital haemostatic dressings: A systematic review, 2011.
Gustafson et al., Chitosan Dressing Provides Hemostasis in Swine Femoral Arterial Injury Model, 2007.
Hapa et al., Does platelet-rich plasma enhance microfracture treatment for chronic focal chondral defects?, Acta Orthop Traumatol Turc 2013;47(3):201-207, 2013.
Hart et al., Platelet-rich plasma in patients with tibiofemoral cartilage degeneration, Arch Orthop Trauma Surg (2013) 133:1295-1301, 2013.
Hoffmann et al., Glutaraldehyde and oxidised dextran as crosslinker reagents for chitosan-based scaffolds for cartilage tissue engineering, 2009.
Huskin et al., Multicentre, prospective, open study to evaluate the safety and efficacy of hylan G-F 20, Knee Surg Sports Traumatol Arthrosc (2008) 16:747-752, 2008.
Sandri et al., Platelet lysate formulations based on mucoadhesive polymers for the treatment of corneal lesions, 2011.
Schuetz et al., A novel thermoresponsive hydrogel based on chitosan, 2008.
Serra et al., Effect of autologous platelet-rich plasma on the repair of full-thickness articular defects in rabbits, 2013.
Sitek et al., PRP-fibrinogen gel-like chondrocyte carrier stabilized by TXA-preliminary study, 2013.
Smyth et al., Establishing proof of concept: Platelet-rich plasma and bonemarrow aspirate concentrate may improve cartilage repair . . . , 2012.
Smyth et al., Platelet-Rich Plasma in the Pathologic Processes of Cartilage: Review of Basic Science Evidence, 2013.
Sohn et al., Efficacy of Three Topical Hemostatic Agents Applied by Medics in a Lethal Groin Injury Model, 2009.
Spreafico et al., Biochemical Investigation of the Effects of Human Platelet Releasates on Human Articular Chondrocytes, 2009.
Sun et al., The regenerative effect of platelet-rich plasma on healing in large osteochondral defects, 2010.
Van Bergen et al., Demineralized bone matrix and platelet-rich plasma do not improve healing of osteochondral defects of the talus: an experimental goat study, 2013.
Ishida et al., The Regenerative Effects of Platelet-Rich Plasma on Meniscal Cells in Vitro and Its in Vivo Application with Biodegradable Gelatin Hydrogel, 2007.
Kon et al., Platelet-rich plasma: intra-articular knee injections produced favorable results on degenerative cartilage lesions, 2010.
Kon et al., Platelet autologous growth factors decrease the osteochondral regeneration capability of a collagen-hydroxyapatite scaffold in a sheep model, 2010.
Kon et al., Platelet-Rich Plasma Intra-Articular Injection Versus Hyaluronic Acid Viscosupplementation as Treatments for Cartilage Pathology . . . , 2011.
Kon et al., Platelet-rich plasma (PRP) to treat sports injuries: evidence to support its use, 2011.
Kon et al., PRP-Augmented ScaffoldsforCartilageRegeneration: A Systematic Review, 2013.
Kozen et al., An Alternative Hemostatic Dressing: Comparison of CELOX, HemCon, and QuikClot, 2008.
Krueger et al., Human Platelet-Rich Plasma Stimulates Migration and Chondrogenic Differentiation of Human Subchondral Progenitor Cells, 2012.
Kutlu et al., Platelet-rich plasma-loaded chitosan scaffolds: preparation and growth factor release kinetics, 2013.
Lee et al., Platelet-rich plasma loaded in situ-formed hydrogel enhances hyaline cartilage regeneration by CB1 upregulation, 2012.
Abarrategi et al., "Chitosan scaffolds for osteochondral tissue regeneration," Wiley Online Library, Sep. 28, 2010.

(56) References Cited

OTHER PUBLICATIONS

Abruzzo et al., "Chitosan/alginate complexes for vaginal delivery of chlorhexidine digluconate," Carbohydrate Polymers 91 (2013).

Ahmad et al., "The role of platelet rich plasma in musculoskeletal science," J R Soc Med Sh Rep 2012; 3:40.

Akeda et al., "Platelet-rich plasma stimulates porcine articular chondrocyte proliferation and matrix biosynthesis," OsteoArthritis and Cartilage (2006).

Andia et al., "Joint pathology and platelet-rich plasma therapies," Informa Healthcare 2012.

Anitua et al., "Autologous preparations rich in growth factors promote proliferation and induce VEGF and HGF production by human tendon cells in culture," J Orth Research 2005.

Anitua et al., "Platelet-released growth factors enhance the secretion of hyaluronic acid and induce hepatocyte growth factor production by synovial . . . " Rheumatology 2007.

Anitua et al., "Fibroblastic response to treatment with different preparations rich in growth factors," Cell Prolif. 2009.

Arca et al., "Chitosan Based Systems for Tissue Engineering Part I: Hard Tissues," FABAD J. Pharm. Sci., 33, 35-49, 2008.

Arca et al., "Chitosan Based Systems for Tissue Engineering Part II: Soft Tissues," FABAD J. Pharm. Sci., 33, 211-216s 2008.

Zaky et al., Platelet lysate favours in vitro expansion of human bone marrow stromal cells . . . , Journal of Tissue Engineering, J Tissue Eng Regen Med 2008; 2.

Zellner et al., Role of mesenchymal stem cells in tissue engineering of meniscus, Apr. 14, 2010 in Wiley InterScience.

Zellner et al., Stem cell-based tissue-engineering for treatment of meniscal tears in the avascular zone, (wileyonlinelibrary.com), 2013.

Zhu et al., Basic science and clinical application of platelet-rich plasma for cartilage defects and osteoarthritis: a review, Osteoarthritis and Cartilage 21 (2013) 1627-1637.

Zumstein et al., The Future of Platelet Concentrates inSports Medicine: Platelet-Rich Plasma, Platelet-Rich Fibrin, and the Impact of Scaffolds and Cells on the Long-term2011.

Shive, et al., BST-CarGel: In Situ ChondroInduction for Cartilage Repair, Operative Techniques in Orthopedics, vol. 16 No. 4, Oct. 1, 2006.

Kutlu et al., Platelet-rich plasma-loaded chitosan scaffolds: Preparation and growth factor release kinetics, J. Biomed Materials Research, vol. 101B, No. 1, Jan. 15, 2013.

Chevrier et al., Injectable chitosan-platelet-rich plasma implants to promote tissue regeneration, J. Tissue Eng'g & Regen Med., May 24, 2017.

Extended European Search Report dated Jul. 5, 2017 in European Patent Application No. 15752804.3.

Lee et al. Platelet-rich plasma loaded in situ-formed hydrogel enhances hyaline cartilage regeneration by CB1 upregulation, Soc. for Biomaterials, Jun. 26, 2012.

Patois et al. "Novel thermosensitive chitosan hydrogels: In vivo evaluation" Wiley InterScience Nov. 3, 2006.

Shive et al. "BST-CarGel: In Situ ChondroInduction for Cartilage Repair" Oper Tech Orthop 16:271-278 (2006).

English Translation of Office Action dated Oct. 9, 2018 in related Japanese Patent Application No. 2016-553370.

Chenite et al. "Novel injectable neutral solutions of chitosan form biodegradable gels in situ" Biomaterials 21 (2000) 2155-2161.

English Translation of Office Action dated Sep. 3, 2019 in related Japanese Patent Application No. 2016-553370.

* cited by examiner

Swirling

Formulation #4

Beads

Formulation #4

R: Clot reaction time is the time in minutes from the start of the tracing to the point where the branches have diverged 2 mm
MA: Maximal amplitude is the maximal distance in mm between the 2 diverging branches and corresponds to clot strength

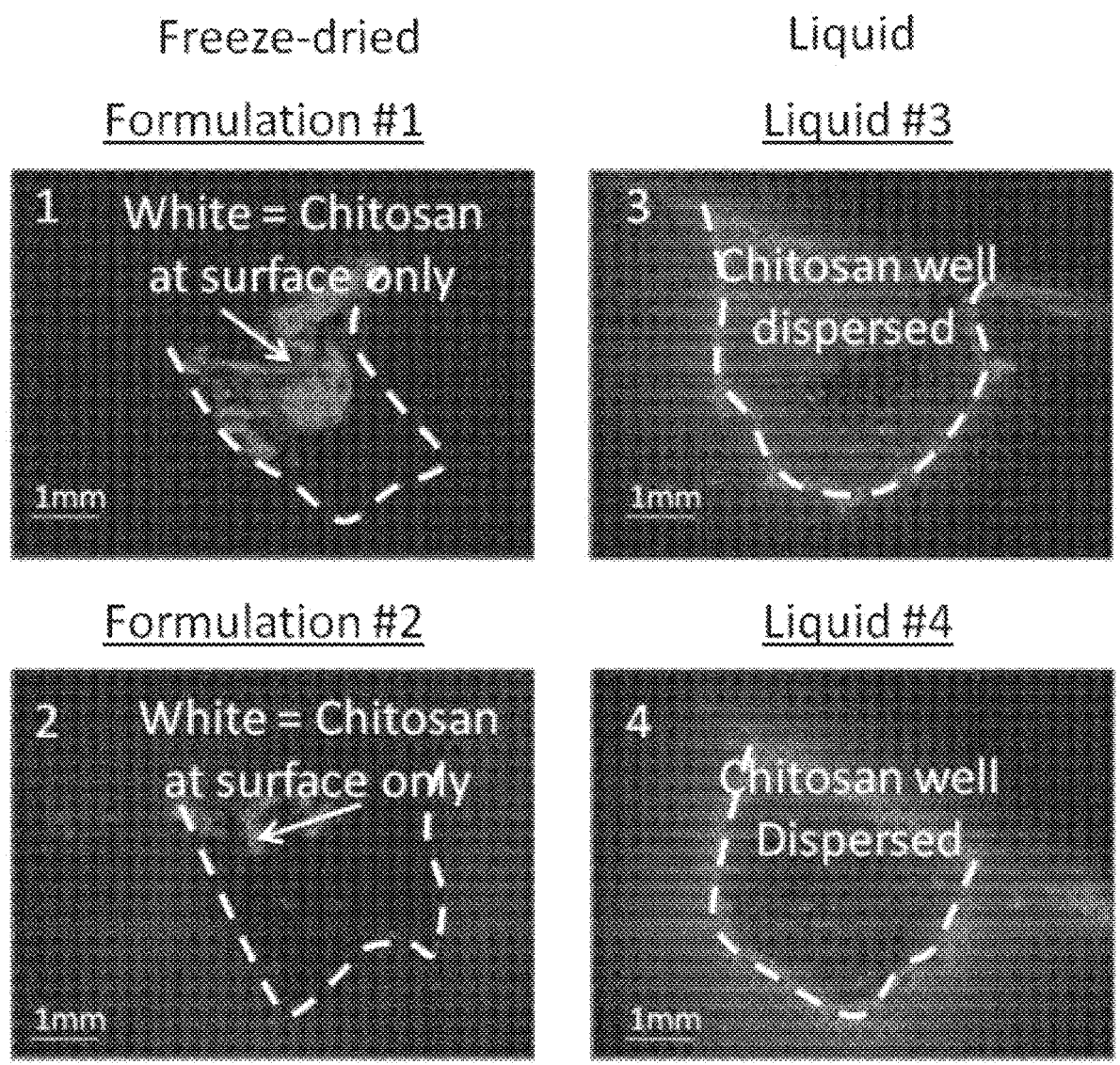

Formulation #3

Formulation #18

Formulation #23

Formulation #9
Solubility excellent

Formulation #12

Formulation #11
Solubility excellent

Formulation #16

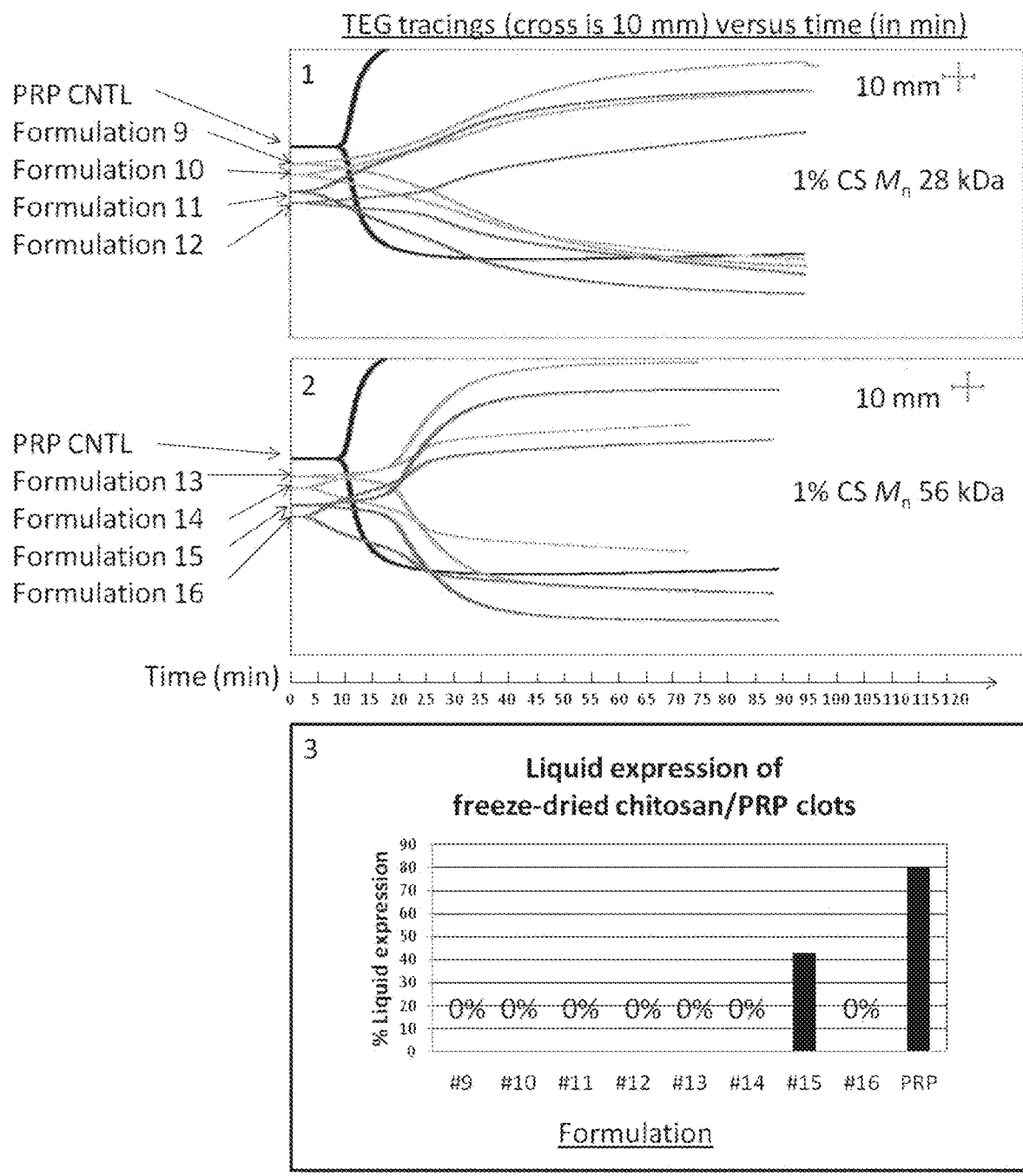

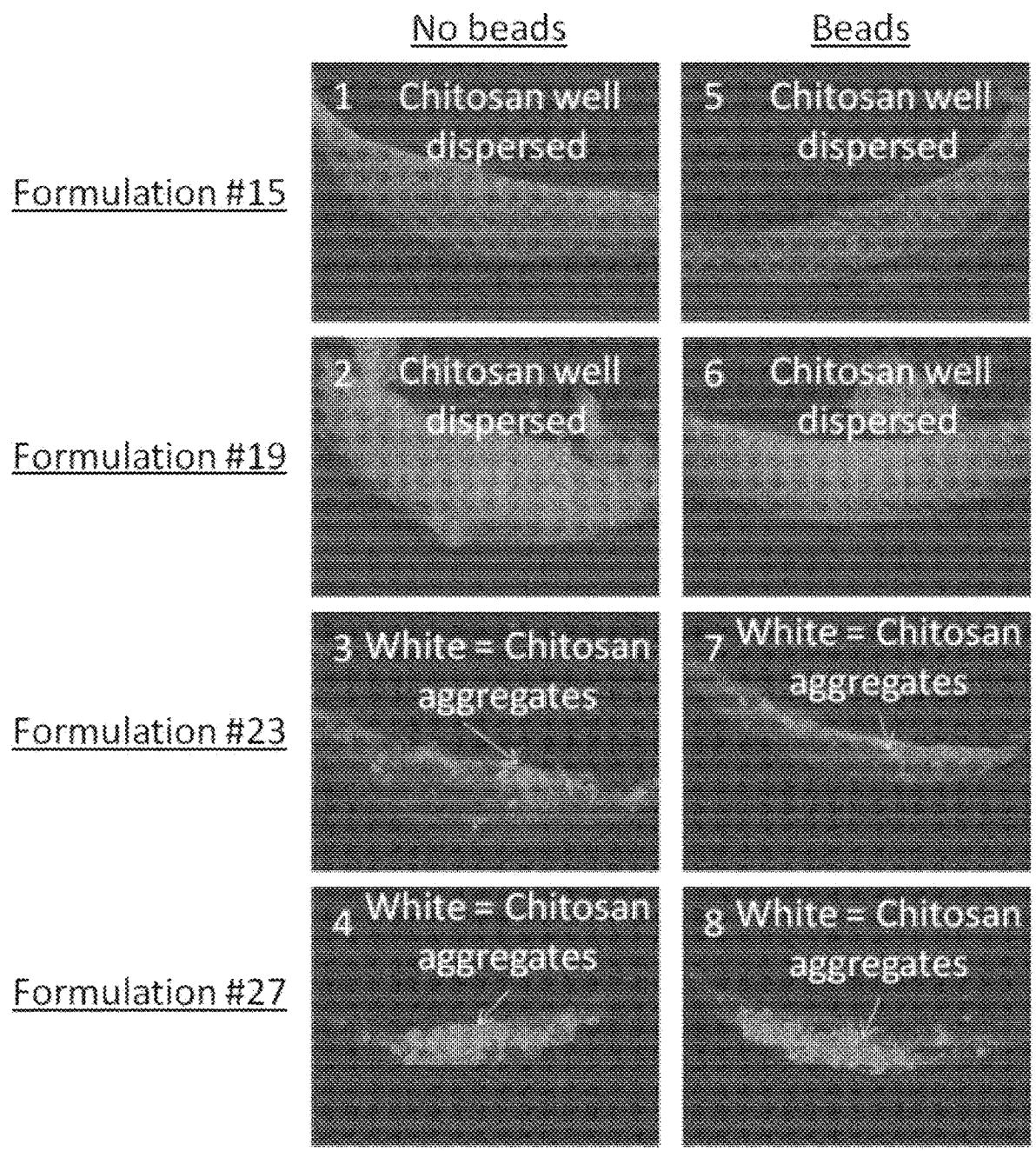

Figure 7B

| Formu-lation | Crush test | | Liquid expression (%) | | Runniness (mm) | | MA (mm) | |
|---|---|---|---|---|---|---|---|---|
| | - Beads | + Beads | - Beads | + Beads | - Beads | + Beads | - Beads | + Beads |
| #15 | 4+ | 4+ | 31.3 | 22.4 | 11.6 | 10.9 | 81.4 | 82.8 |
| #19 | 3+ | 3+ | 0 | 0 | 33.9 | 34.4 | 64.9 | 50.3 |
| #23 | 3+ | 3+ | 57.5 | 42.2 | 46.8 | 35.6 | 60.3 | 75.6 |
| #27 | 4+ | 4+ | 7.5 | 13.6 | 9.5 | 12.1 | 81.0 | 78.3 |
| PRP CNTL | Donor 1 | Donor 2 | Donor 1 | Donor 2 | Donor 1 | Donor 2 | Donor 1 | Donor 2 |
| | 4+ | 4+ | 71.2 | 83.3 | 179.5 | 201.4 | 80.0 | 67.4 |

Formulation #13 (2%T)

Formulation #14 (6%T)

PRP CNTL

Formulation #13 (2%T)

Formulation #14 (6%T)

PRP CNTL

Formulation #13 (2%T)

Cake appearance

Cake solubility

Create surgical defect

Elongate defect

Rasp defect

Pre-place sutures

Pre-place needles

Deliver Chitosan-PRP

1 Day

3 Weeks

Chitosan-PRP    vs    PRP alone

| Microdrilled defect treated with PRP after 21 days | Microdrilled defect treated with CS-PRP after 21 days |

| Histological appearance of defect treated with PRP | Histological appearance of defect treated with CS-PRP |

FREEZE-DRIED POLYMER COMPOSITIONS FOR MIXING WITH PLATELET RICH PLASMA TO FORM IMPLANTS FOR TISSUE REPAIR AND/OR COMPOSITIONS FOR THERAPEUTIC INTRA-ARTICULAR INJECTIONS

FIELD

This disclosure relates to freeze-dried polymer compositions for mixing with platelet-rich plasma (PRP) or blood to form implants for tissue repair and/or compositions for therapeutic intra-articular injections.

BACKGROUND

Chitosan (CS) has been used as a scaffold for engineering hard and soft tissues [Arca, H. C. and S. Senel, *Chitosan Based Systems for Tissue Engineering Part 1: Hard Tissues*. FABAD J. Pharm. Sci., 2008a. 33: p. 35-49, Arca, H. C. and S. Senel, *Chitosan Based Systems for Tissue Engineering Part II: Soft Tissues*. FABAD J. Pharm. Sci., 2008b. 33: p. 211-216]. Freeze-dried scaffolds have been fabricated from pure chitosan [Nettles, D. L., S. H. Elder, and J. A. Gilbert, *Potential use of chitosan as a cell scaffold material for cartilage tissue engineering*. Tissue engineering, 2002. 8(6): p. 1009-16, Concaro, S., et al., *Effect of cell seeding concentration on the quality of tissue engineered constructs loaded with adult human articular chondrocytes*. Journal of tissue engineering and regenerative medicine, 2008. 2 (1): p. 14-21], cross-linked chitosan [Hoffmann, B., et al., *Glutaraldehyde and oxidised dextran as crosslinker reagents for chitosan-based scaffolds for cartilage tissue engineering*. Journal of Materials Science-Materials in Medicine, 2009. 20(7): p. 1495-1503], modified chitosan [Li, Z., et al., *Preparation and evaluation of thiolated chitosan scaffolds for tissue engineering*. Journal of Biomedical Materials Research Part A, 2010a. 92A(3): p. 973-978], and from chitosan blended with glycosaminoglycans [Chen, Y.-L., et al., *Composite chondroitin-6-sulfate/dermatan sulfate/chitosan scaffolds for cartilage tissue engineering*. Biomaterials, 2007. 28 (14): p. 2294-2305], polysaccharides [Li, Z. and M. Zhang, *Chitosan-alginate as scaffolding material for cartilage tissue engineering*. Journal of biomedical materials research. Part A, 2005. 75(2): p. 485-93], polypeptides [Gong, Z., et al., *Use of synovium-derived stromal cells and chitosan/collagen type I scaffolds for cartilage tissue engineering*. Biomedical materials (Bristol, England), 2010. 5(5): p. 055005] or synthetic polymers [Martel-Estrada, S. A., et al., *In vitro bioactivity of chitosan/poly (D,L-lactide-co-glycolide) composites*. Materials Letters, 2011. 65(1): p. 137-141]. Several freeze-dried scaffolds combining chitosan and bioactive ceramics, bioactive glasses or glass-ceramics have also been developed [Costa-Pinto, A. R., R. L. Reis, and N. M. Neves, *Scaffolds Based Bone Tissue Engineering: The Role of Chitosan*. Tissue Engineering Part B-Reviews, 2011. 17(5): p. 331-347]. Freeze-dried scaffolds consisting of chitosan of different molecular weight, degree of deacetylation (DDA) and high or low calcium content were previously implanted in rabbit osteochondral femoral condylar defects for cartilage repair [Abarrategi, A., et al., *Chitosan scaffolds for osteochondral tissue regeneration*. Journal of Biomedical Materials Research Part A, 2010. 95A(4): p. 1132-1141].

Chitosan has been freeze-dried in the presence of lyoprotectants for different applications. A bilayer structure of chitosan sponge adhering to a chitosan film was freeze-dried in the presence of sodium chloride, glucose or sucrose to culture human neofetal dermal fibrobroblasts [Ma, J., et al., *A preliminary in vitro study on the fabrication and tissue engineering applications of a novel chitosan bilayer material as a scaffold of human neofetal dermal fibroblasts*. Biomaterials, 2001. 22(4): p. 331-6]. Chitosan/poly (ethylene glycol)-β-dicalcium pyrophosphate scaffolds were freeze-dried in the presence of sucrose, glucose or fructose [Wang, J. W. and M. H. Hon, *Sugar-mediated chitosan/poly (ethylene glycol)-beta-dicalcium pyrophosphate composite: mechanical and microstructural properties*. Journal of biomedical materials research. Part A, 2003a. 64(2): p. 262-72]. Freeze-dried chitosan microspheres containing sucrose, maltose or trehalose were prepared for nasal drug delivery [Cho, H. J., et al., *Evaluation of protein stability and in vitro permeation of lyophilized polysaccharides-based microparticles for intranasal protein delivery*. International journal of pharmaceutics, 2011. 416(1): p. 77-84]. Lyophilised chitosan wafers and thiolated chitosan-based xerogels were freeze-dried in the presence of glycerol and mannitol as potential buccal delivery systems [Ayensu, I., J. C. Mitchell, and J. S. Boateng, *In vitro characterisation of chitosan based xerogels for potential buccal delivery of proteins*. Carbohydrate Polymers, 2012b. 89(3): p. 935-941, Ayensu, I., J. C. Mitchell, and J. S. Boateng, *Development and physico-mechanical characterisation of lyophilised chitosan wafers as potential protein drug delivery systems via the buccal mucosa*. Colloids and Surfaces B-Biointerfaces, 2012a. 91: p. 258-265]. Mannitol was used as a bulking agent for lyophilised chitosan/alginate vaginal inserts [Abruzzo, A., et al., *Chitosan/alginate complexes for vaginal delivery of chlorhexidine digluconate*. Carbohydrate Polymers, 2013. 91(2): p. 651-658].

Wound dressings containing freeze-dried chitosan acetate (U.S. Pat. Nos. 7,371,403, 7,482,503, 7,897,832) are regularly distributed to combat troops. These dressings have been widely tested in pre-clinical animal models [Burkatovskaya, M., et al., *Use of chitosan bandage to prevent fatal infections developing from highly contaminated wounds in mice*. Biomaterials, 2006. 27(22): p. 4157-4164; Gustafson, S. B., et al., *Chitosan dressing provides hemostasis in swine femoral arterial injury model*. Prehospital Emergency Care, 2007. 11(2): p. 172-178; Sohn, V. Y., et al., *Efficacy of Three Topical Hemostatic Agents Applied by Medics in a Lethal Groin Injury Model*. Journal of Surgical Research, 2009. 154 (2): p. 258-261; Burkatovskaya, M., et al., *Effect of chitosan acetate bandage on wound healing in infected and noninfected wounds in mice*. Wound Repair and Regeneration, 2008. 16(3): p. 425-431; Kozen, B. G., et al., *An alternative hemostatic dressing: Comparison of CELOX, HemCon, and QuikClot*. Academic Emergency Medicine, 2008. 15(1): p. 74-81; Arnaud, F., et al., *Comparison of 10 hemostatic dressings in a groin puncture model in swine*. Journal of Vascular Surgery, 2009. 50(3): p. 632-639; Dai, T., et al., *Chitosan Acetate Bandage as a Topical Antimicrobial Dressing for Infected Burns*. Antimicrobial Agents and Chemotherapy, 2009. 53(2): p. 393-400; Devlin, J. J., et al., *COMPARISON OF ChitFlex®, CELOX™, AND QuikClot® IN CONTROL OF HEMORRHAGE*. Journal of Emergency Medicine, 2011. 41(3): p. 237-245; Littlejohn, L. F., et al., *Comparison of Celox-A, ChitoFlex, WoundStat, and Combat Gauze Hemostatic Agents Versus Standard Gauze Dressing in Control of Hemorrhage in a Swine Model of Penetrating Trauma*. Academic Emergency Medicine, 2011. 18(4): p. 340-350] but clinical data is less extensive [Wedmore, I., et al., *A special report on the chitosan-based hemostatic dressing: Experience in current combat operations*. Journal of Trauma-Injury Infection and Critical Care, 2006. 60(3): p. 655-658; Brown, M. A., M. R. Daya, and J. A. Worley, *EXPERIENCE WITH CHITOSAN DRESSINGS IN A CIVILIAN EMS SYSTEM*. Journal of Emergency Medicine, 2009. 37(1): p. 1-7; Cox, E. D., et al., *New hemostatic agents in the combat setting*. Transfusion, 2009. 49: p. 248S-255S; Granville-Chapman, J., N. Jacobs, and M. J. Midwinter, *Prehospital haemostatic dressings: A systematic review*. Injury-International Journal of the Care of the Injured, 2011. 42 (5): p. 447-459]. Blended and anti-microbial-loaded chitosan freeze-dried dressings have also been described [Yeo, J. H., et al., *The effects of Pva/chitosan/fibroin (PCF)-blended spongy sheets on wound healing in rats*. Biological & pharmaceutical bulletin, 2000. 23(10): p. 1220-3; Rossi, S., et al., *Wound dressings based on chitosans and hyaluronic acid for the release of chlorhexidine diacetate in skin ulcer therapy*. Pharmaceutical development and technology, 2007. 12(4): p. 415-22; Ong, S.-Y., et al., *Development of a chitosan-based wound dressing with improved hemostatic and antimicrobial properties*. Biomaterials, 2008. 29(32): p. 4323-4332].

In all of the above, the scaffolds/dressings were designed to remain solid at the time of use/implantation. A different in situ gelling approach has been used for chitosan thermosetting hydrogel formulations containing different gelling agents (1,2-propanediol, glycerol, trehalose or mannitol) (US2009004230) [Schuetz, Y. B., R. Gurny, and O. Jordan, *A novel thermoresponsive hydrogel based on chitosan*. European journal of pharmaceutics and biopharmaceutics: official journal of Arbeitsgemeinschaft fur Pharmazeutische Verfahrenstechnik e.V, 2008. 68(1): p. 19-25; Patois, E., et al., *Novel thermosensitive chitosan hydrogels: in vivo evaluation*. Journal of biomedical materials research. Part A, 2009. 91(2): p. 324-30]. In this case, the freeze-dried chitosan cakes were reconstituted and solubilised by adding cold water under magnetic stirring at 4° C. Thermogelling properties were preserved for formulations containing chitosan (59% DDA-410 kDa or 63% DDA-1220 kDa) with 8% or 10% trehalose, as well as with 10% mannitol upon freeze-drying [Schuetz, Y. B., R. Gurny, and O. Jordan, *A novel thermoresponsive hydrogel based on chitosan*. European journal of pharmaceutics and biopharmaceutics: official journal of Arbeitsgemeinschaft fur Pharmazeutische Verfahrenstechnik e.V, 2008. 68 (1): p. 19-25]. Freeze-dried formulations containing 1.4% (w/v) chitosan and 8% trehalose reconstituted in water were shown to be thermosensitive and resident subcutaneously for up to 3 months in vivo in the rat, where they induced mild inflammation [Patois, E., et al., *Novel thermosensitive chitosan hydrogels: in vivo evaluation*. Journal of biomedical materials research. Part A, 2009. 91(2): p. 324-30].

The use of platelet-rich plasma (PRP) in orthopaedics and sports medicine has been reviewed recently [Fortier, L. A., C. H. Hackett, and B. J. Cole, *The Effects of Platelet-Rich Plasma on Cartilage: Basic Science and Clinical Application*. Operative Techniques in Sports Medicine, 2011b. 19(3): p. 154-159; Kon, E., et al., *Platelet-rich plasma (PRP) to treat sports injuries: evidence to support its use*. Knee Surgery Sports Traumatology Arthroscopy, 2011b. 19(4): p. 516-527; Lopez-Vidriero, E., et al., *The Use of Platelet-Rich Plasma in Arthroscopy and Sports Medicine: Optimizing the Healing Environment*. Arthroscopy—the Journal of Arthroscopic and Related Surgery, 2010. 26(2): p. 269-278; Andia, I., M. Sanchez, and N. Maffulli, *Joint pathology and platelet-rich plasma therapies*. Expert Opinion on Biological Therapy, 2012. 12(1): p. 7-22; Ahmad, Z., et al., *The role of platelet rich plasma in musculoskeletal science*. JRSM short reports, 2012. 3(6): p. 40, 8 pages; Smyth, N. A., et al., *Establishing proof of concept: Platelet-rich plasma and bone marrow aspirate concentrate may improve cartilage repair following surgical treatment for osteochondral lesions of the talus*. World journal of orthopedics, 2012. 3(7): p. 101-8; Smyth, N. A., et al., *Platelet-Rich Plasma in the Pathologic Processes of Cartilage: Review of Basic Science Evidence*. Arthroscopy—the Journal of Arthroscopic and Related Surgery, 2013. 29 (8): p. 1399-1409; Kon, E., et al., *PRP-Augmented Scaffolds for Cartilage Regeneration: A Systematic Review*. Operative Techniques in Sports Medicine, 2013. 21(2): p. 108-115; Zhu, Y., et al., *Basic science and clinical application of platelet-rich plasma for cartilage defects and osteoarthritis: a review*. Osteoarthritis and Cartilage, 2013a. 21(11): p. 1627-1637]. A classification system comprising four PRP families has been proposed [Zumstein, M. A., T. Bielecki, and D. M. D. Ehrenfest, *The Future of Platelet Concentrates in Sports Medicine: Platelet-Rich Plasma, Platelet-Rich Fibrin, and the Impact of Scaffolds and Cells on the Long-term Delivery of Growth Factors*. Operative Techniques in Sports Medicine, 2011. 19(3): p. 190-197]. The first two families are platelet-rich fibrin (PRF), solid fibrin materials in which leukocytes are present (Leukocyte-PRF) or absent (Pure-PRF). The last 2 families are liquid platelet suspensions containing leukocytes (Leukocyte-PRP) or devoid of leukocytes (Pure-PRP), which can be activated by thrombin, calcium chloride ($CaCl_2$), calcium gluconate or other activators to form gels. Platelet lysates have been produced by freeze-thawing PRP prior to use, which ruptures platelets and releases platelet-derived growth factors [Del Fante, C., et al., *Platelet Lysate Mucohadesive Formulation to Treat Oral Mucositis in Graft Versus Host Disease Patients: A New Therapeutic Approach*. AAPS PharmSciTech, 2011. 12 (3): p. 893-899; Sandri, G., et al., *Platelet lysate formulations based on mucoadhesive polymers for the treatment of corneal lesions*. Journal of Pharmacy and Pharmacology, 2011. 63(2): p. 189-198; Rossi, S., et al., *"Sponge-like" dressings based on biopolymers for the delivery of platelet lysate to skin chronic wounds*. International journal of pharmaceutics, 2013. 440(2): p. 207-215].

In vitro, activated PRP releasates have been shown to increase skin, synovium and tendon fibroblast proliferation [Anitua, E., et al., *Fibroblastic response to treatment with different preparations rich in growth factors*. Cell proliferation, 2009. 42(2): p. 162-70; Anitua, E., et al., *Autologous preparations rich in growth factors promote proliferation and induce VEGF and HGF production by human tendon cells in culture*. Journal of orthopaedic research: official publication of the Orthopaedic Research Society, 2005. 23(2): p. 281-6], hyaluronic acid (HA) and hepatocyte growth factor (HGF) secretion from synovial fibroblasts isolated from OA (osteoarthritic) patients [Anitua, E., et al., *Platelet-released growth factors enhance the secretion of hyaluronic acid and induce hepatocyte growth factor production by synovial fibroblasts from arthritic patients*. Rheumatology (Oxford, England), 2007. 46(12): p. 1769-72], proliferation, proteoglycan (PG) and collagen synthesis from chondrocytes [Park, S. I., et al., *Time-sequential modulation in expression of growth factors from platelet-rich plasma (PRP) on the chondrocyte cultures*. Mol Cell Biochem, 2012. 361 (1-2): p. 9-17] and from chondrocytes embedded in alginate beads [Akeda, K., et al., *Platelet-rich plasma stimulates porcine articular chondrocyte proliferation and matrix biosynthesis*. Osteoarthritis and Cartilage, 2006. 14 (12): p. 1272-1280] and to decrease expression of cyclooxygenase-2 (COX-2) and chemokine-receptor (CXCR4) in chondrocytes [Bendinelli, P., et al., *Molecular Basis of Anti-Inflammatory Action of Platelet-Rich Plasma on Human Chondrocytes: Mechanisms of NF-kappa B Inhibition Via HGF*. Journal of Cellular Physiology, 2010. 225 (3): p. 757-766]. PRP increased cell proliferation of both sheep chondrocytes and mesenchymal stem cells [Drengk, A., et al., *Influence of platelet-rich plasma on chondrogenic differentiation and proliferation of chondrocytes and mesenchymal stem cells*. Cells Tissues Organs, 2009. 189(5): p. 317-26]. Chondrocytes seeded onto gelatin microcarriers, mixed with PRP and activated with $CaCl_2$ form structurally stable constructs [Pettersson, S., et al., *Human articular chondrocytes on macroporous gelatin microcarriers form structurally stable constructs with blood-derived biological glues in vitro*. Journal of tissue engineering and regenerative medicine, 2009. 3(6): p. 450-460]. Supplementing the culture medium of human mesenchymal stem cells (MSCs) with unactivated PRP increased proliferation and expression of Runx, Sox9 and aggrecan [Mishra, A., et al., *Buffered Platelet-Rich Plasma Enhances Mesenchymal Stem Cell Proliferation and Chondrogenic Differentiation*. Tissue Engineering Part C-Methods, 2009. 15(3): p. 431-435]. Adding PRP to the culture medium of bi-phasic constructs composed of bovine chondrocytes seeded on top of a porous ceramic substrate enhanced cartilage formation [Petrera, M., et al., *Supplementation With Platelet-Rich Plasma Improves the In Vitro Formation of Tissue-Engineered Cartilage With Enhanced Mechanical Properties*. Arthroscopy—the Journal of Arthroscopic and Related Surgery, 2013. 29 (10): p. 1685-1692]. Grafts composed of chondrocytes, fibrinogen and PRP remained viable throughout a 3-week culture period [Sitek, P., et al., *PRP-fibrinogen gel-like chondrocyte carrier stabilized by TXA-preliminary study* Cell Tissue Banking 2013. 14 (1): p. 133-140]. PRP inhibited the pro-inflammatory effects of IL-1β in cultures of human chondrocytes [van Buul, G. M., et al., *Platelet-Rich Plasma Releasate Inhibits Inflammatory Processes in Osteoarthritic Chondrocytes* American Journal of Sports Medicine, 2013. 39 (11): p. 2362-2370; Wu, C.-C., et al., *Regenerative potentials of platelet-rich plasma enhanced by collagen in retrieving pro-inflammatory cytokine-inhibited chondrogenesis* Biomaterials, 2011. 32 (25): p. 5847-5854]. Releasates of activated platelet lysate had a strong effect on OA chondrocyte proliferation as well as Sox9 and aggrecan expression [Spreafico, A., et al., *Biochemical Investigation of the Effects of Human Platelet Releasates on Human Articular Chondrocytes*. Journal of Cellular Biochemistry, 2009. 108 (5): p. 1153-1165]. Platelet lysate increased migration of human cortico-spongious progenitors and induced their chondrogenic differentiation in high-density pellet cultures [Krueger, J. P., et al., *Human platelet-rich plasma stimulates migration and chondrogenic differentiation of human subchondral progenitor cells*. Journal of Orthopaedic Research, 2012. 30(6): p. 845-852]. Platelet lysates also increased chondrogenic differentiation of human bone marrow stromal cells [Zaky, S. H., et al., *Platelet lysate favours in vitro expansion of human bone marrow stromal cells for bone and cartilage engineering* J Tiss Eng Reg Med, 2008. 2 (8): p. 472-481].

In pre-clinical models, rabbit chondrocytes were mixed with PRP, the PRP was activated with thrombin/$CaCl_2$ and injected subcutaneously to form dorsal cartilage nodules after 2 months [Wu, W., et al., *Autologous injectable tissue-engineered cartilage by using platelet-rich plasma: Experimental study in a rabbit model*. Journal of Oral and Maxillofacial Surgery, 2007b. 65 (10): p. 1951-1957], suggesting that a similar approach could be used for cartilage repair [Wu, W., et al., *Platelet-rich plasma—A promising cell carrier for micro-invasive articular cartilage repair*. Medical Hypotheses, 2009. 72 (4): p. 455-457]. Freeze-dried collagen bilayer scaffolds loaded with PRP [Qi, Y. Y., et al., *Local Delivery of Autologous Platelet in Collagen Matrix Synergistically Stimulated In-situ Articular Cartilage Repair, in 13th International Conference on Biomedical Engineering*, Vols 1-3, C. T. Lim and J. C. H. Goh, Editors. 2009a. p. 1289-1292; Qi, Y. Y., et al., *Local Delivery of Autologous Platelet in Collagen Matrix Simulated In Situ Articular Cartilage Repair*. Cell Transplantation, 2009b. 18(10-11): p. 1161-1169] and poly-lactic-glycolic acid (PLGA) scaffolds loaded with PRP along with thrombin/$CaCl_2$ [Sun, Y., et al., *The regenerative effect of platelet-rich plasma on healing in large osteochondral defects*. International orthopaedics, 2010. 34 (4): p. 589-97] improved healing in rabbit patellar groove defect models. Loading PRP on a bi-phasic scaffold led to improved histological scores in an osteochondral defect model in the mini-pig condyle [Betsch, M., et al., *Bone Marrow Aspiration Concentrate and Platelet Rich Plasma for Osteochondral Repair in a Porcine Osteochondral Defect Model*. PLOS ONE, 2013. 8 (8): p. e71602]. PRP-augmented microfracture improved healing in a chronic defect model of the rat medial femoral condyle [Hapa, O., et al., *Does platelet-rich plasma enhance micro fracture treatment for chronic focal chondral defects? An in-vivo study performed in a rat model*. Acta Orthop Traum Turc, 2013. 47 (3): p. 201-207]. Gelatin-poly (ethylene glycol)-tyramine (GPT) conjugate hydrogel was used as scaffold in conjunction with autologous chondrocytes and PRP to treat rat xyphoid defects [Lee, H.-R., et al., *i Platelet-rich plasma loaded in situ-formed hydrogel enhances hyaline cartilage regeneration by CB1 upregulation*. Journal of Biomedical Materials Research Part A, 2012a. 100A(11): p. 3099-3107] and rabbit patellar groove defects [Lee, H.-R., et al., *Platelet-rich plasma loaded hydrogel scaffold enhances chondrogenic differentiation and maturation with up-regulation of CB1 and CB2*. Journal of Controlled Release, 2012b. 159(3): p. 332-337]. PRP used as a gel in conjunction with microfracture was more effective compared to liquid injections of unactivated PRP in a sheep condylar defect model [Milano, G., et al., *The effect of platelet rich plasma combined with microfractures on the treatment of chondral defects: an experimental study in a sheep model*. Osteoarthritis and cartilage 2010. 18 (7): p. 971-80]. Good healing was observed when a hyaluronic acid membrane was used in conjunction with PRP and cartilage fragments in a trochlear osteochondral defect model in adult rabbits [Marmotti, A., et al., *One-step osteochondral repair with cartilage fragments in a composite scaffold*. Knee Surg Sports Traumatol Arthrosc, 2012. 20(12): p. 2590-601]. A 3-D scaffold was prepared from PRP and loaded with bone-marrow derived stromal cells to successfully treat osteochondral trochlear defects in rabbits [Xie, X., et al., *Comparative evaluation of MSCs from bone marrow and adipose tissue seeded in PRP-derived scaffold for cartilage regeneration*. Biomaterials, 2012. 33 (29): p. 7008-18]. In a sheep condylar defect model however, a 3-layer biomimetic scaffold performed better on its own than when PRP activated with $CaCl_2$ was soaked onto the scaffold [Kon, E., et al., *Platelet autologous growth factors decrease the osteochondral regeneration capability of a collagen-hydroxyapatite scaffold in a sheep model*. Bmc Musculoskeletal Disorders, 2010b. 11]. Dimineralized bone matrix rehydrated with PRP failed to improve osteochondral repair in the talus of goats [van Bergen, C. J. A., et al., *Demineralized bone matrix and platelet-rich plasma do not improve healing of* osteochondral defects of the talus: an experimental goat study. Osteoarthritis and Cartilage, 2013. 21(11): p. 1746-1754]. PRP also did not improve healing in the medial femoral condyle of immature NZW rabbits [Serra, I. C., et al., *Effect of autologous platelet-rich plasma on the repair of full-thickness articular defects in rabbits*. Knee Surgery Sports Traumatology Arthroscopy, 2013. 21(8): p. 1730-1736]. Intra-articular injections of autologous conditioned plasma improved healing in sheep condylar defect models [Milano, G., et al., *Repeated Platelet Concentrate Injections Enhance Reparative Response of Microfractures in the Treatment of Chondral Defects of the Knee: An Experimental Study in an Animal Model*. Arthroscopy—the Journal of Arthroscopic and Related Surgery, 2012. 28(5): p. 688-701; Milano, G., et al., *The effect of autologous conditioned plasma on the treatment of focal chondral defects of the knee. An experimental study*. International journal of immunopathology and pharmacology, 2011. 24(1 Suppl 2): p. 117-24]. Intra-articular injections of PRP embedded in gelatin hydrogel microspheres were used in a rabbit OA model [Saito, M., et al., *Intraarticular administration of platelet-rich plasma with biodegradable gelatin hydrogel microspheres prevents osteoarthritis progression in the rabbit knee*. Clinical and Experimental Rheumatology, 2009. 27(2): p. 201-207]. Intra-articular injections of PRP were used in an inflammatory arthritis model in pigs to restore cartilaginous phenotype and decrease inflammation [Lippross, S., et al., *Intraarticular Injection of Platelet-Rich Plasma Reduces Inflammation in a Pig Model of Rheumatoid Arthritis of the Knee Joint* Arthritis Rheumatism, 2011. 63(11): p. 3344-3353]. In a rabbit meniscal defect model, cross-linked and freeze-dried gelatin loaded with platelet lysate improved healing [Ishida, K., et al., *The regenerative effects of platelet-rich plasma on meniscal cells in vitro and its in vivo application with biodegradable gelatin hydrogel*. Tissue engineering, 2007. 13(5): p. 1103-1112]. PRP was loaded onto hyaluronan-ester-gelatin scaffolds but failed to improve repair in two different rabbit meniscus defect models [Zellner, J., et al., *Stem cell-based tissue-engineering for treatment of meniscal tears in the avascular zone*. Journal of Biomedical Materials Research Part B: Applied Biomaterials, 2013. 101(7):1133-42; Zellner, J., et al., *Role of mesenchymal stem cells in tissue engineering of meniscus*. Journal of Biomedical Materials Research Part A, 2010. 94A(4): p. 1150-1161].

Two clinical trials investigating PRP for meniscal healing are posted on www.clinicaltrials.gov (Identifiers: NCT00961597 and NCT01991353).

Combinations of chitosan and blood-derived products have been described previously by others. Freeze-drying methods were used to prepare solid formats of chitosan (scaffolds or wound dressings) combined with blood-derived products in the following 3 papers. In Oktay et al, chitosan freeze-dried solid sponges were loaded with PRP activated with 10% $CaCl_2$ and autologous blood (containing thrombin) and implanted in cranial defect where they induced an inflammatory reaction [Oktay, E. O., et al., *Effects of platelet-rich plasma and chitosan combination on bone regeneration in experimental rabbit cranial defects*. The Journal of oral implantology, 2010. 36 (3): p. 175-84]. Two different fabrication methods were used to prepare solid scaffolds containing unactivated PRP and chitosan in Kutlu et al [Kutlu, B., et al., *Platelet-rich plasma-loaded chitosan scaffolds: Preparation and growth factor release kinetics*. Journal of Biomedical Materials Research Part B-Applied Biomaterials, 2013. 101B(1): p. 28-35]. For the first method, chitosan was dissolved in acetic acid and mixed with increasing volumes of PRP prior to freeze-drying. For the second method, increasing volumes of PRP were dropped onto freeze-dried chitosan scaffolds. In Rossi et al (US20110280952), sponge-like solid dressings composed of either platelet lysate and chitosan glutamate/glycine or of platelet lysate and chitosan glutamate/glycine/glycerophosphate were prepared for delivery to chronic skin wounds [Rossi, S., et al., *"Sponge-like" dressings based on biopolymers for the delivery of platelet lysate to skin chronic wounds*. International journal of pharmaceutics, 2013. 440 (2): p. 207-215]. In all of the above, the chitosan formulations were solid and designed to remain so immediately post-implantation. In Ezodini-Erdanaki et al, sterilised chitosan powder in solid form was mixed with a drop of autologous blood and implanted into a tibial defect in a rat model [Ezoddini-Ardakani, F., et al., *Histologic evaluation of chitosan as an accelerator of bone regeneration in microdrilled rat tibias*. Dental research journal, 2012. 9(6): p. 694-9]. In Sandri et al (WO2010064267), composites of chitosan glutamate and hydroxypropylmethyl cellulose mixed with platelet lysate were prepared for wound healing applications [Sandri, G., et al., *Platelet lysate formulations based on mucoadhesive polymers for the treatment of corneal lesions*. Journal of Pharmacy and Pharmacology, 2011. 63 (2): p. 189-198]. In Bi et al, injectable composites consisting of chitosan/citric acid/glucose mixed with β-tricalcium phosphate powder and PRP activated with bovine thrombin and 10% $CaCl_2$ were used in a goat bone defect model [Bi, L., et al., *Reconstruction of goat tibial defects using an injectable tricalcium phosphate/chitosan in combination with autologous platelet-rich plasma*. Biomaterials, 2010. 31(12): p. 3201-11].

None of the above prior art describes soluble formulations of freeze-dried chitosan and concentrated PRP that are physiological, viable and active. Whole blood is used in Ezodini-Erdanaki et al. In Sandri et al, the pH of the chitosan glutamate vehicle was reported to be acidic at 5.5, the platelet lysate (containing ruptured platelets and platelet-derived growth factors) is diluted two-fold during preparation and the preparation process entails storage of the platelet-derived growth factors for 2 weeks at 4° C., which more than likely destroys activity [Sandri, G., et al., *Platelet lysate formulations based on mucoadhesive polymers for the treatment of corneal lesions*. Journal of Pharmacy and Pharmacology, 2011. 63(2): p. 189-198]. In Bi et al, the clot activators are 10% $CaCl_2$, which has osmolality of ~2500 mOsm (far above physiological ~300 mOsm), and bovine thrombin, which has been linked to serious coagulopathies [Bi, L., et al., *Reconstruction of goat tibial defects using an injectable tricalcium phosphate/chitosan in combination with autologous platelet-rich plasma*. Biomaterials, 2010. 31(12): p. 3201-11].

A need exists for stable lyophilized chitosan formulations for reconstitution and simultaneous activation in PRP to form physiological injectable solutions, preferably that gel in situ forming tissue implants that are volume conserving. There is also a need for formulations that do not retract and that adhere to tissue surfaces. Liquid solutions of the polymer chitosan with whole blood and PRP have been discussed in (U.S. Pat. No. 8,258,117; WO2008064487; WO2011060555; WO2011060545). However, mixing a freeze-dried polymer directly into PRP or blood to form tissue implants has not. None of the above mentioned prior art fulfills these needs. To our knowledge, there are no publications to date describing the direct solubilisation of freeze-dried chitosan formulations in PRP or in blood to form viable non-retracting in situ gelling implants.

Research in viscosupplementation has mainly focused on the use of hyaluronic acid in various forms [Huskin, J. P., et al., *Multicentre, prospective, open study to evaluate the safety and efficacy of hylan G-F 20 in knee osteoarthritis subjects presenting with pain following arthroscopic meniscectomy*. Knee Surgery Sports Traumatology Arthroscopy, 2008. 16(8): p. 747-752; Conrozier, T., et al., *Prospective, multi-centre, randomised evaluation of the safety and efficacy of five dosing regimens of viscosupplementation with hylan G-F 20 in patients with symptomatic tibio-femoral osteoarthritis: a pilot study*. Archives of Orthopaedic and Trauma Surgery, 2009. 129(3): p. 417-423; Noel, E., et al., *Efficacy and safety of Hylan G-F 20 in shoulder osteoarthritis with an intact rotator cuff. Open-label prospective multicenter study*. Joint Bone Spine, 2009. 76(6): p. 670-673; Wang, Y., et al., *Effects of Hylan G-F 20 supplementation on cartilage preservation detected by magnetic resonance imaging in osteoarthritis of the knee: a two-year single-blind clinical trial*. Bmc Musculoskeletal Disorders, 2011. 12], with some studies reporting on the use of PRP intra-articular injections for the treatment of OA or cartilage disease [Wang-Saegusa, A., et al., *Infiltration of plasma rich in growth factors for osteoarthritis of the knee short-term effects on function and quality of life*. Archives of Orthopaedic and Trauma Surgery, 2011. 131(3): p. 311-317; Napolitano, M., et al., *Autologous platelet gel for tissue regeneration in degenerative disorders of the knee*. Blood Transfusion, 2012. 10(1): p. 72-77; Sanchez, M., et al., *Intra-articular injection of an autologous preparation rich in growth factors for the treatment of knee OA: a retrospective cohort study*. Clinical and Experimental Rheumatology, 2008. 26(5): p. 910-913; Kon, E., et al., *Platelet-rich plasma: intra-articular knee injections produced favorable results on degenerative cartilage lesions*. Knee Surgery Sports Traumatology Arthroscopy, 2010a. 18(4): p. 472-479; Kon, E., et al., *Platelet-Rich Plasma Intra-Articular Injection Versus Hyaluronic Acid Viscosupplementation as Treatments for Cartilage Pathology: From Early Degeneration to Osteoarthritis*. Arthroscopy—the Journal of Arthroscopic and Related Surgery, 2011a. 27(11): p. 1490-1501; Filardo, G., et al., *Platelet-rich plasma intra-articular knee injections for the treatment of degenerative cartilage lesions and osteoarthritis*. Knee Surgery Sports Traumatology Arthroscopy, 2011. 19(4): p. 528-535; Patel, S., et al., *Treatment With Platelet-Rich Plasma Is More Effective Than Placebo for Knee Osteoarthritis A Prospective, Double-Blind, Randomized Trial*. American Journal of Sports Medicine, 2013. 41(2): p. 356-364; Gobbi, A., et al., *Platelet-rich plasma treatment in symptomatic patients with knee osteoarthritis: preliminary results in a group of active patients*. Sports health, 2012. 4(2): p. 162-72; Hart, R., et al., *Platelet-rich plasma in patients with tibiofemoral cartilage degeneration*. Archives of Orthopaedic and Trauma Surgery, 2013. 133 (9): p. 1295-1301]. In the only randomized controlled trial published to date, a single injection of leukocyte-filtered PRP activated with $CaCl_2$ was found to alleviate early knee OA symptoms at 6 months [Patel, S., et al., *Treatment With Platelet-Rich Plasma Is More Effective Than Placebo for Knee Osteoarthritis A Prospective, Double-Blind, Randomized Trial*. American Journal of Sports Medicine, 2013. 41(2): p. 356-364]. Several clinical trials investigating the effect of intra-articular injections of PRP on OA or cartilage degeneration are posted on www.clinicaltrials.gov (Identifiers NCT01418755, NCT01670578, NCT01270412, NCT02012530).

There is a need for: freeze-dried chitosan formulations that contain lyoprotectants for storage stability but still remain physiological upon reconstitution with PRP; formulations that may be quickly, preferably completely and easily reconstituted (rehydrated) in PRP to form injectable homogenous chitosan/PRP composites; formulations that contain a clot activator for in situ gelling if required; chitosan formulations with at least one of the following characteristics: 1) Freeze-dried cakes with mechanical properties suitable for storage and shipping; 2) Cakes that reconstitute, preferably completely and rapidly, in PRP, PPP, whole blood or water as required; 3) Coagulation is not inhibited by cake components when a solid chitosan/PRP hybrid implant needs to be formed; 4) Hybrid implants are solid and stable to resist mechanical loading in vivo; 5) Hybrid implants inhibit platelet-mediated clot retraction to fill tissue defects; 6) Hybrid implants are homogenous, preferably without phase separation of the polymer and blood components improving, preferably optimizing in vivo responses; 7) The mixtures are viscous and paste-like for tissue repair applications; 8) The reconstituted mixtures have physiological properties for in vivo implantation.

The above mentioned prior art has not addressed PRP mixed with polymer solutions to provide effective viscosupplementation without requiring any solidification. Physiological freeze-dried chitosan formulations reconstituted with PRP are expected to provide viscosupplementation (due to the presence of chitosan) and to provide slow release of platelet-derived factors into the articular cavity by chitosan binding to PRP. There is a need for freeze-dried chitosan formulations designed for viscosupplementation comprising at least one of the following performance criteria: 1) Good mechanical properties of cakes for storage and shipping; 2) Reconstitution or rehydration of cake, preferably complete, more preferably complete and rapid; 3) Reconstituted mixtures are viscous for intra-articular viscosupplementation; 4) Reconstituted mixtures have physiological properties suitable for intra-articular injections.

BRIEF SUMMARY

In one aspect, there is provided a freeze-dried polymer composition comprising chitosan and at least one lyoprotectant. Preferably, the composition is reconstituted in platelet-rich plasma (PRP) and/or blood-derived products forming: i) at least one viable in situ solidifying and non-retracting implant for tissue repair; ii) a composition for therapeutic intra-articular injection. The at least one lyoprotectant is selected from the group consisting of monosaccharide, polyol, disaccharide, trisaccharide, oligosaccharide/polysaccharide, high molecular weight excipient, amino acid, protein and combinations thereof.

In one embodiment the blood and/or blood-derived products are selected from the group consisting of PRP, PPP, PRF, autologous conditioned plasma, platelet suspension, platelet lysate and combinations thereof.

In another aspect, there is provided a freeze-dried chitosan composition comprising at least one lyoprotectant. The at least one lyoprotectant is selected from the group consisting of monosaccharide, polyol, disaccharide, trisaccharide, oligosaccharide/polysaccharide, high molecular weight excipient, amino acid, protein and combinations thereof.

Preferably, the monosaccharide is selected from the group consisting of glucose, fructose, fucose, galactose, mannose, ribose, xylosearabinose and combinations thereof. Preferably, the disaccharide is selected from the group consisting of lactose, maltose, sucrose, trehalose, cellobiose, melibiose and combinations thereof. Preferably, the trisaccharide is selected from maltotriose, raffinose and combinations thereof. Preferably the polyol is selected from mannitol, sorbitol, xylitol, inositol and combinations thereof. Preferably, the amino acid is selected from the group consisting of histidine, glycine, arginine, alanine, glutamic acid, lysine, phenylalanine and combinations thereof. Preferably, the oligosaccharide/polysaccharide is selected from the group consisting of dextran, cyclodextrin, maltodextrin, hydroxyethyl starch, ficoll, cellulose, hydroxypropylmethyl cellulose, inulin and combinations thereof. Preferably, the protein is selected from the group consisting of bovine serum albumin (BSA), casein, globulin, lactalbumin, lactate dehydrogenase (LDH), lysozyme, myoglobin, ovalbumin and combinations thereof.

Preferably the amount of the at least one lyoprotectant is from about 0.1% to about 30%, more preferably from about 0.5% to about 10% and most preferably from about 0.5% to about 6% w/v.

Preferably, the chitosan in the freeze-dried chitosan composition has a molecular weight number from about 20 to about 250 kDa, more preferably from about 25 to about 125 kDa and most preferably from about 30 to about 100 kDa. Preferably the concentration of chitosan in the freeze-dried chitosan composition is from about 0.25% to about 10%, more preferably from about 0.25% to about 5% and most preferably from about 0.25% to about 2.5% w/v.

In another embodiment, the freeze-dried chitosan composition optionally further comprises at least one clot activator. Preferably, the clot activator is selected from the group consisting of calcium chloride, calcium gluconate, calcium acetate, calcium carbonate, calcium glubionate, calcium gluceptate, calcium lactate, calcium lactobionate, calcium phosphate and combinations thereof.

In another aspect, there is provided a freeze-dried chitosan composition preferably having at least one, more preferably more than one, most preferably all of the following general characteristics: 1—Homogenous solid freeze-dried cake with good mechanical properties for shipping (Assessed with cake appearance); 2—Rapid and complete reconstitution, preferably less than 5 minutes, more preferably less than 2 minutes, in at least one of PRP, platelet-poor plasma (PPP), blood or water, as required (Assessed with visual inspection upon reconstitution).

For mixing the freeze-dried chitosan composition with PRP or blood, the composition preferably has at least one, more preferably more than one, most preferably all of the following characteristics: 3—The mixture does not inhibit coagulation when a solid implant needs to be formed (in one embodiment, assessed with thromboelastography); 4—The coagulated mixture (preferably an implant) is mechanically stable (in one embodiment, assessed with manual crushing test); 5—The coagulated mixture (preferably an implant) inhibits clot retraction that occurs with blood or PRP alone (in one embodiment, assessed with liquid expression measurements); 6—Good mixing is achieved without phase separation of the polymer and blood components (in one embodiment assessed with histology); 7—The mixture, prior to reconstitutition is viscous and paste-like for tissue repair applications or a viscous suspension in the case of intra-articular viscosupplementation (in one embodiment assessed with runniness test); 8—The mixture has close-to-physiological properties, preferably from about 165 mOsm to about 660 mOsm, more preferably from about 195 mOsm to about 550 mOsm, most preferably about 330 mOsm, preferably from about pH 6.4 to about pH 7.9, more preferably from about pH 6.9 to about pH 7.9, most preferably about pH 7.4 after reconstitution for in vivo implantation or intra-articular injections (in one embodiment assessed with osmolality and pH measurements).

In another aspect, there is provided a process for preparing a freeze-dried polymer composition comprising chitosan comprising the steps of:

a) contacting the chitosan with water to form an aqueous mixture, b) contacting the aqueous mixture with at least one lyoprotectant, c) optionally contacting the aqueous mixture with at least one clot activator, d) sterilizing the chitosan, the at least one lyoprotectant and the optionally at least one clot activator, individually, prior to mixing or after addition of the at least one lyoprotectant and the optional at least one clot activator to said chitosan/water aqueous mixture; and e) freeze-drying the aqueous mixture containing the at least one lyoprotectant and optional at least one clot activator.

In one embodiment of the process, the chitosan in the freeze-dried polymer/chitosan composition has a molecular weight number from about 20 to about 250 kDa, more preferably from about 25 to about 125 kDa and most preferably from about 30 to about 100 kDa. Preferably the concentration of chitosan in the freeze-dried chitosan composition is less than about 10%, more preferably less than about 5% and most preferably less than 2.5%.

In another embodiment, the at least one lyoprotectant is selected from the group consisting of monosaccharide, polyol, disaccharide, trisaccharide, oligosaccharide/polysaccharide, high molecular weight excipient, amino acid, protein and combinations thereof.

Preferably, the monosaccharide is selected from the group consisting of glucose, fructose, fucose, galactose, mannose, ribose, xylose, arabinose and combinations thereof. Preferably, the disaccharide is selected from the group consisting of lactose, maltose, sucrose, trehalose, cellobiose, melibiose and combinations thereof. Preferably, the trisaccharide is selected from maltotriose, raffinose and combinations thereof. Preferably the polyol is selected from mannitol, sorbitol, xylitol, inositol and combinations thereof. Preferably, the amino acid is selected from the group consisting of histidine, glycine, arginine, alanine, glutamic acid, lysine, phenylalanine and combinations thereof. Preferably, the oligosaccharide/polysaccharide is selected from the group consisting of dextran, cyclodextrin, maltodextrin, hydroxyethyl starch, ficoll, cellulose, hydroxypropylmethyl cellulose, inulin and combinations thereof. Preferably, the protein is selected from the group consisting of bovine serum albumin (BSA), casein, globulin, lactalbumin, lactate dehydrogenase (LDH), lysozyme, myoglobin, ovalbumin and combinations thereof.

Preferably the amount of the at least one lyoprotectant is from about 0.5% to about 30%, more preferably from about 0.5% to about 10% and most preferably from about 0.5% to about 6% w/v.

The optional at least one clot activator is preferably selected from the group consisting of calcium chloride, calcium gluconate, calcium acetate, calcium carbonate, calcium glubionate, calcium gluceptate, calcium lactate, calcium lactobionate calcium phosphate and combinations thereof.

In another embodiment, different sterile chitosan formulations may be prepared for freeze-drying. Variants may include chitosan weight average molecular weight ($M_w$), number average molecular weight ($M_n$), degree of deacetylation (DDA), concentration and protonation levels as described in the different examples. Other variables may include the mixing method, the at least one clot activator (preferably a metal salt, more preferably a metal halide, most preferably $CaCl_2$) concentration and method of addition, lyoprotectant concentration (preferably selected from the group consisting of trehalose, mannitol and sucrose), salt concentration (preferably a metal salt, more preferably a metal halide, most preferably NaCl) and buffer concentration (preferably histidine). In one embodiment, a tracer is added for imaging purposes, preferably a filter-sterilised rhodamine-chitosan tracer is added to the cakes, preferably to a final ratio of 0.01% (vol tracer/vol solution) for imaging purposes.

In another aspect, the freeze-dried chitosan composition may be reconstituted in blood or a blood product selected from the group consisting of PRP, PPP, PRF, autologous conditioned plasma, platelet suspension and platelet lysate and combinations thereof. Preferably, the reconstituted freeze-dried chitosan composition is used to prepare implants for tissue repair. Preferably, the tissue repair is selected from the group consisting of meniscus repair, cartilage repair, bone repair, rotator cuff repair, epicondylitis, ligament/tendon repair, acute injury, tendinopathy, tear, muscle repair, oral/maxillofacial surgery, skin repair, wound management, ulcer treatment and combinations thereof.

In another aspect, PRP and PPP are used to test the performance characteristics of the freeze-dried cakes. In a preferred embodiment, anticoagulated whole blood is centrifuged, preferably at about 160 g for about 10 minutes preferably at room temperature resulting in a supernatant. The supernatant is collected along with the first about 2 mm of erythrocytes and centrifuged again at about 400 g for about 10 minutes preferably at room temperature in order to separate the PRP (bottom 1.5 mL in the tube, classified as a Leukocyte-PRP, also containing a fraction of erythrocytes) and PPP (clear plasma).

In another embodiment, to test cake reconstitution, about 1 mL of PRP or PPP (preferable for visual assessment because it is clear) is pipetted into each vial containing freeze-dried cake. Mixing is done, preferably by swirling or by shaking vigorously for 10 seconds in the presence (or absence) of three 0.39 g stainless steel balls. In one embodiment, the freeze-dried cakes resolubilised within about 3 to about 5 minutes. pH and osmolality of reconstituted mixtures were also recorded to determine whether they close to physiological.

In another embodiment, to test cake performance, about 1 mL of PRP may be pipetted into each vial containing freeze-dried cake. Formulations were either mixed by swirling or by shaking vigorously for 10 seconds in the presence or absence of three 0.39 g stainless steel balls.

In another embodiment, coagulation properties of the formulations may be tested by thromboelastography (TEG). The mixture does not inhibit coagulation when a solid implant needs to be formed.

In another embodiment, hybrid clot volume retention may be assessed by measuring liquid expression from the hybrid clots that occurs upon clot retraction. The coagulated mixtures (implants) should largely inhibit clot retraction that occurs with blood or PRP alone in order to fill tissue defects completely.

Chitosan dispersion in hybrid clots may be assessed by histology. Good mixing should be achieved without phase separation of the polymer and blood components to ensure timely biodegradability and beneficial in situ biological responses.

Paste-like properties of the formulations may be assessed with a runniness test. Preferably, the mixtures should have appropriate handling properties which would preferably be viscous and paste-like for tissue repair applications or a viscous suspension in the case of intra-articular viscosupplementation Mechanical properties of the formulations may be assessed with a crushing test. Preferably, the coagulated mixtures (implants) should be mechanically stable to withstand loading at implantation sites.

Handling properties of the formulations may be tested ex vivo in a meniscal defect model and in a cartilage defect model. Preferably, the mixtures should be easily delivered to tissue defects with standard operating room apparatus.

In vivo clearing of the freeze-dried formulations may be assessed in a rabbit chondral defect model and in a subcutaneous implantation rabbit model. Preferably, the mixtures should be biodegradable and cleared in a timely fashion without inducing deleterious effects such as chronic inflammation. More preferably, hybrid implants composed of chitosan/PRP should be retained longer than PRP in vivo in order to modulate wound healing events.

Hybrid Chitosan/PRP implants may be injected in vivo into meniscus defects and acute as well as chronic cartilage defects to modulate healing mechanisms and improve repair.

BRIEF DESCRIPTION OF THE FIGURES

FIGS. 3A and 3B depict hybrid clots prepared with freeze-dried formulations and liquid solutions of Example 3.

FIG. 6B depicts TEG testing and liquid expression testing of various formulations under various testing conditions of Example 6.

FIG. 7A depicts hybrid clots of Example 7.

FIG. 7B depicts hybrid clots undergoing various tests of Example 7.

DETAILED DESCRIPTION OF THE FIGURES

Figure 1A:
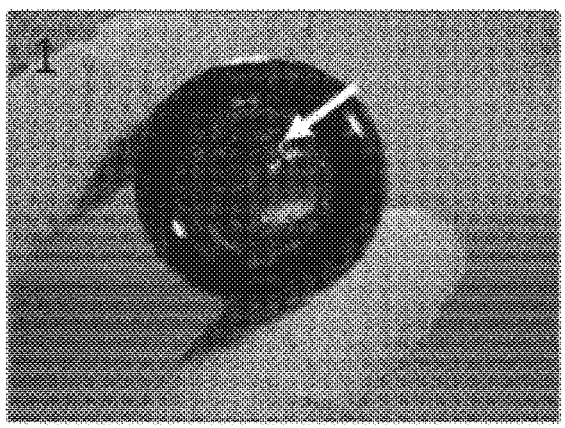
FIGS. 1A and 1B depict various freeze-dried chitosan cakes and testing thereof of Example 1.
Figure 1A:
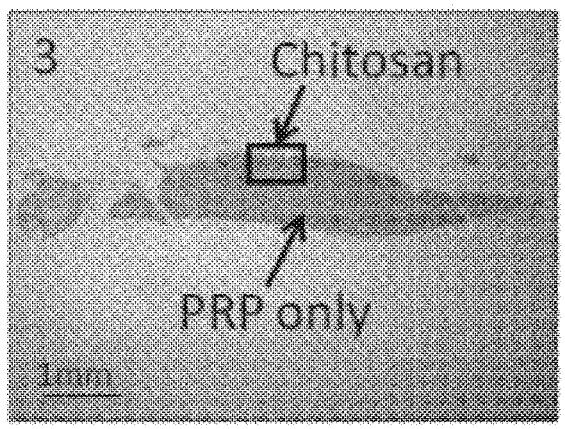
Figure 1A:
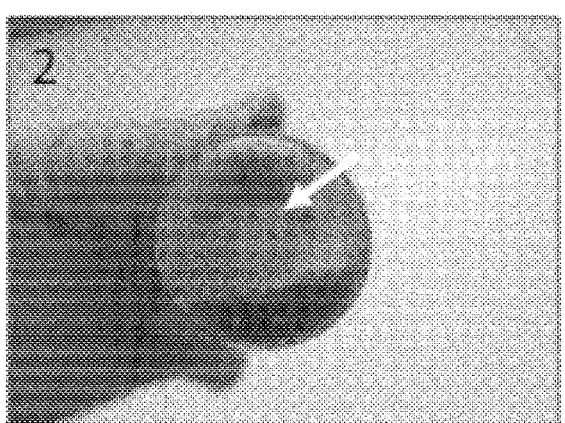
Figure 1A:
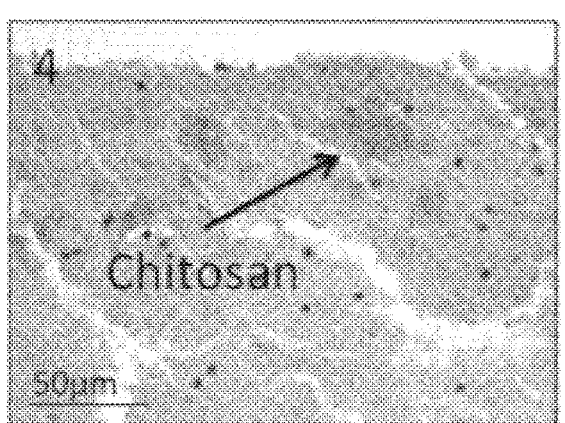

Referring now to FIG. 1A, white arrows point to undissolved chitosan particles after reconstituting freeze-dried chitosan cakes with PRP using a swirling method (1A1) and by mixing with stainless steel beads (1A2). Chitosan dispersion in the PRP hybrid clots was not homogenous for any of the formulations (1A3 and 1A4 depict results of formulation #4). The rectangle in 1A3 underwent high magnification resulting in 1A4 and shows chitosan aggregates. Formulation #4: 0.56% (w/v) CS 80.6% DDA $M_w$ 380 kDa with 7% (w/v) trehalose and 45 mM $CaCl_2$.

Figure 1B:
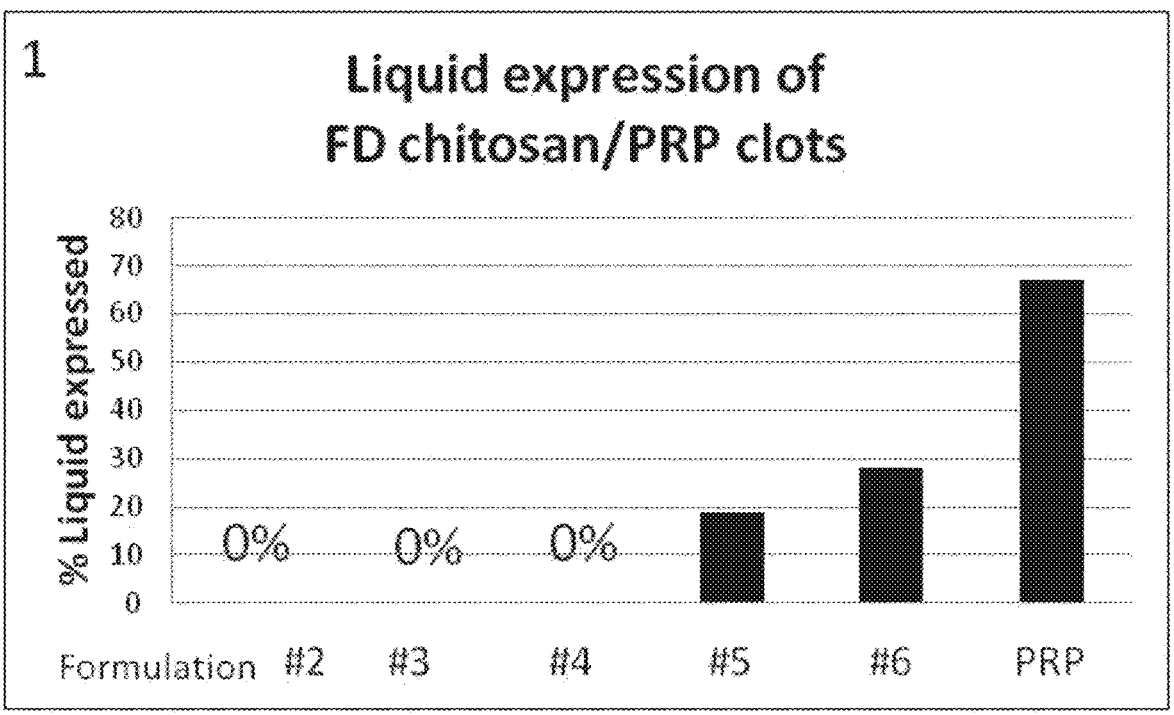
Figure 1B:
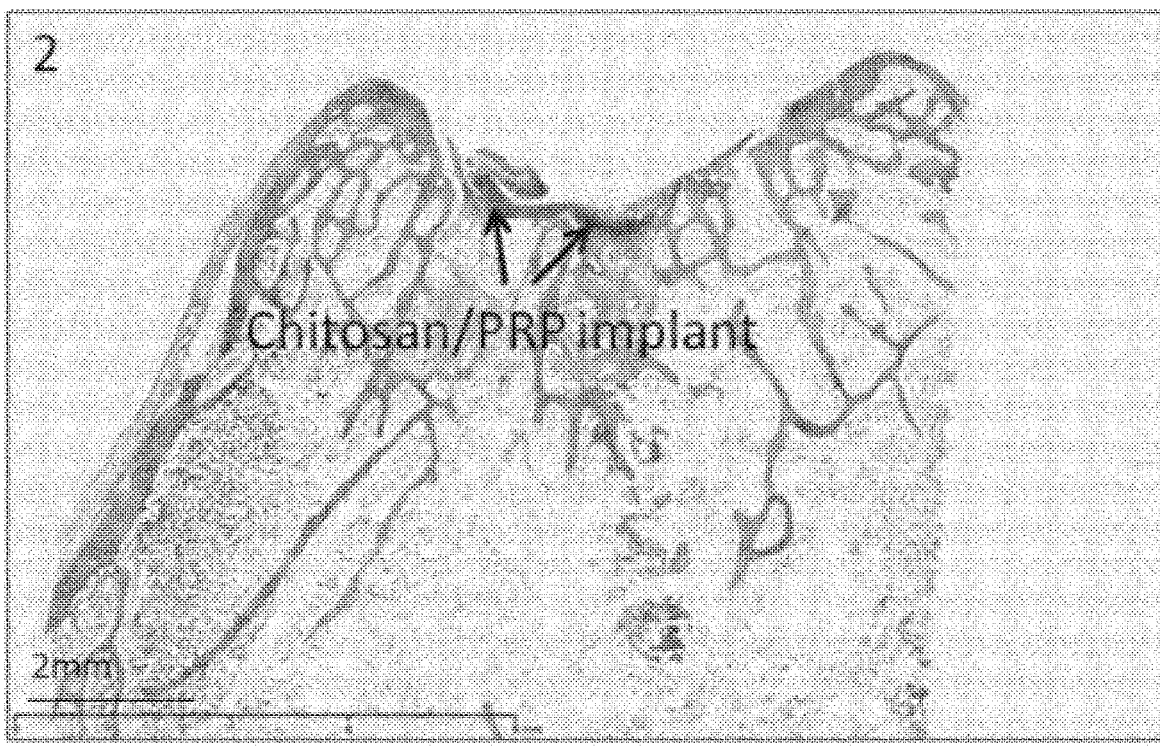

Referring now to FIG. 1B, liquid expression from the hybrid clots (formulations #2, 3, 4, 5, 6) was less than for PRP alone (1B1). Freeze-dried chitosan/PRP implant (formulation #3) was detected at the top of the microdrill holes 10 days post-treatment in a rabbit cartilage repair model (1B2). Formulation #2: 0.67% (w/v) CS 80.6% DDA $M_w$ 341 kDa with 201 mM NaCl activated post-reconstitution with liquid $CaCl_2$; Formulation #3: 0.56% (w/v) CS 80.6% DDA $M_w$ 389 kDa with 6.3% (w/v) sucrose and 45 mM $CaCl_2$; Formulation #4: 0.56% (w/v) CS 80.6% DDA $M_w$ 380 kDa with 7% (w/v) trehalose and 45 mM $CaCl_2$; Formulation #5: 0.56% (w/v) CS 80.6% DDA $M_w$ 400 kDa with 5.2% (w/v) sucrose, 45 mM $CaCl_2$ and 33 mM histidine; Formulation #6: 0.56% (w/v) CS 80.6% DDA $M_w$ 391 kDa with 5.8% (w/v) trehalose, 45 mM $CaCl_2$ and 33 mM histidine.

Figure 2A:
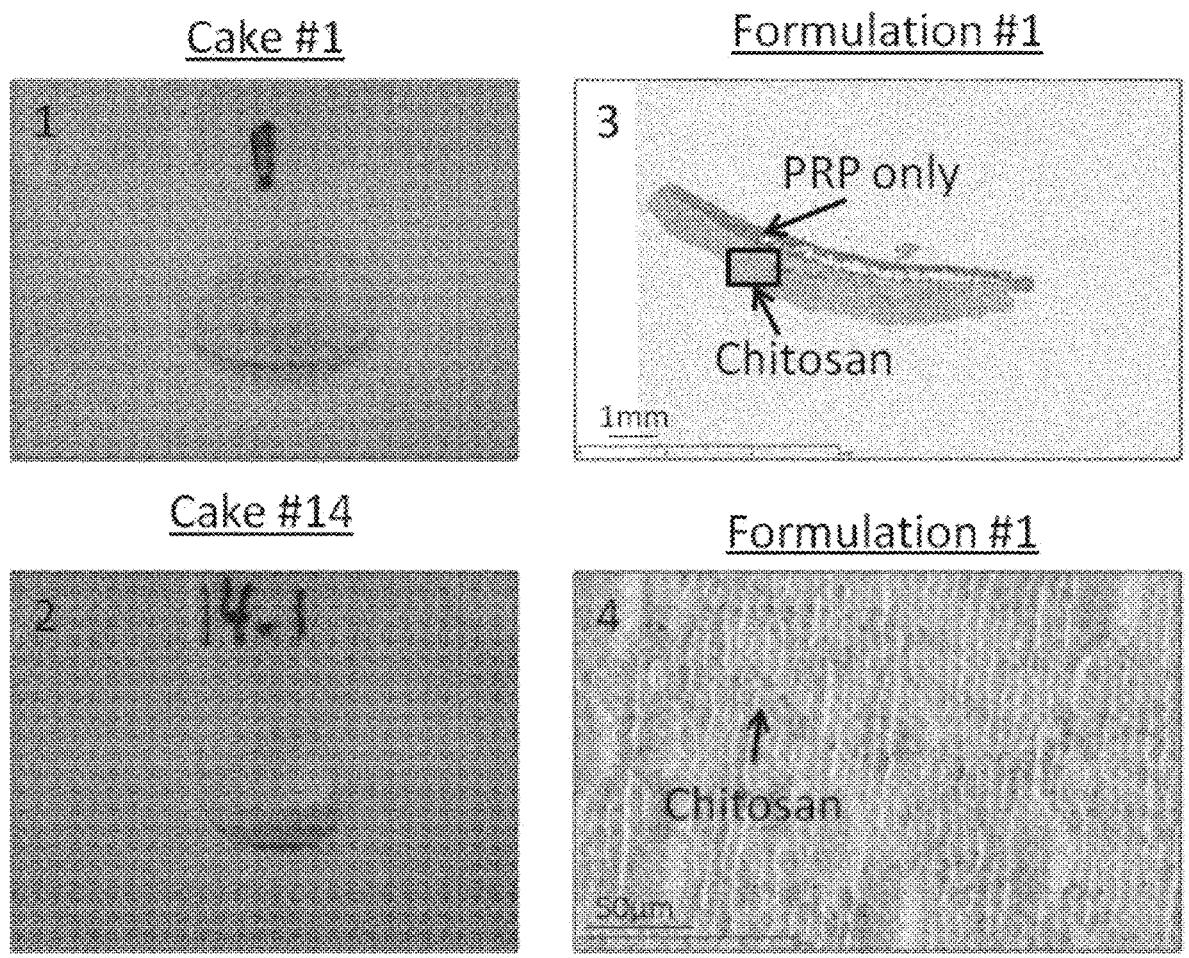
FIGS. 2A and 2B depict freeze-dried chitosan cakes and testing thereof of Example 2.

Referring now to FIG. 2A, freeze-dried chitosan cakes obtained with formulation #1 (2A1) and formulation #14 (2A2) are depicted. Chitosan dispersion in the hybrid clots was not homogenous for any of the formulations (2A3 and 2A4 show formulation #1). The rectangle in 2A3 underwent high magnification resulting in 2A4 which depicts the presence of chitosan while the region above the rectangle in 2A3 did not. Formulation #1: 0.56% (w/v) CS 80.6% DDA $M_n$ 151 kDa with 42.2 mM $CaCl_2$; Formulation #14: 0.56% (w/v) CS 80.6% DDA $M_n$ 148 kDa with 10% (w/v) trehalose and 42.2 mM $CaCl_2$.

Figure 2B:
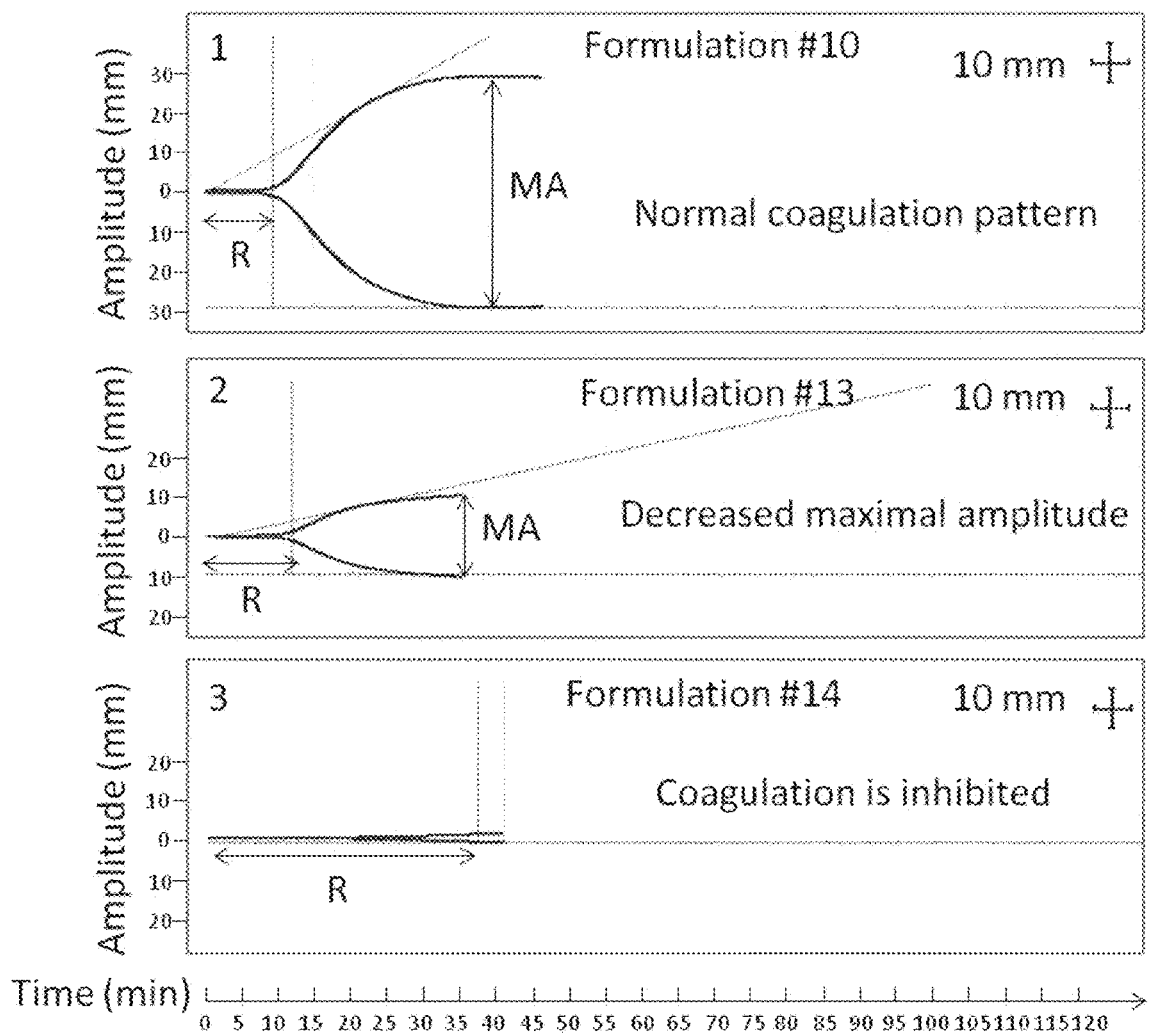

Referring now to FIG. 2B, coagulation of freeze-dried chitosan/PRP hybrids was normal in the presence of 2% (w/v) lyoprotectant (Formulation #10 shown in 2B1) but was inhibited in the presence of 8% (w/v) or 10% (w/v) lyoprotectant (Formulations #13 and 14 shown in 2B2 and 2B3 respectively). Formulation #10: 0.56% (w/v) CS 80.6% DDA $M_n$ 162 kDa with 2% (w/v) trehalose and 42.2 mM $CaCl_2$; Formulation #13: 0.56% (w/v) CS 80.6% DDA with 8% (w/v) trehalose and 42.2 mM $CaCl_2$; Formulation #14: 0.56% (w/v) CS 80.6% DDA $M_n$ 148 kDa with 10% (w/v) trehalose and 42.2 mM $CaCl_2$.

Figure 3A:
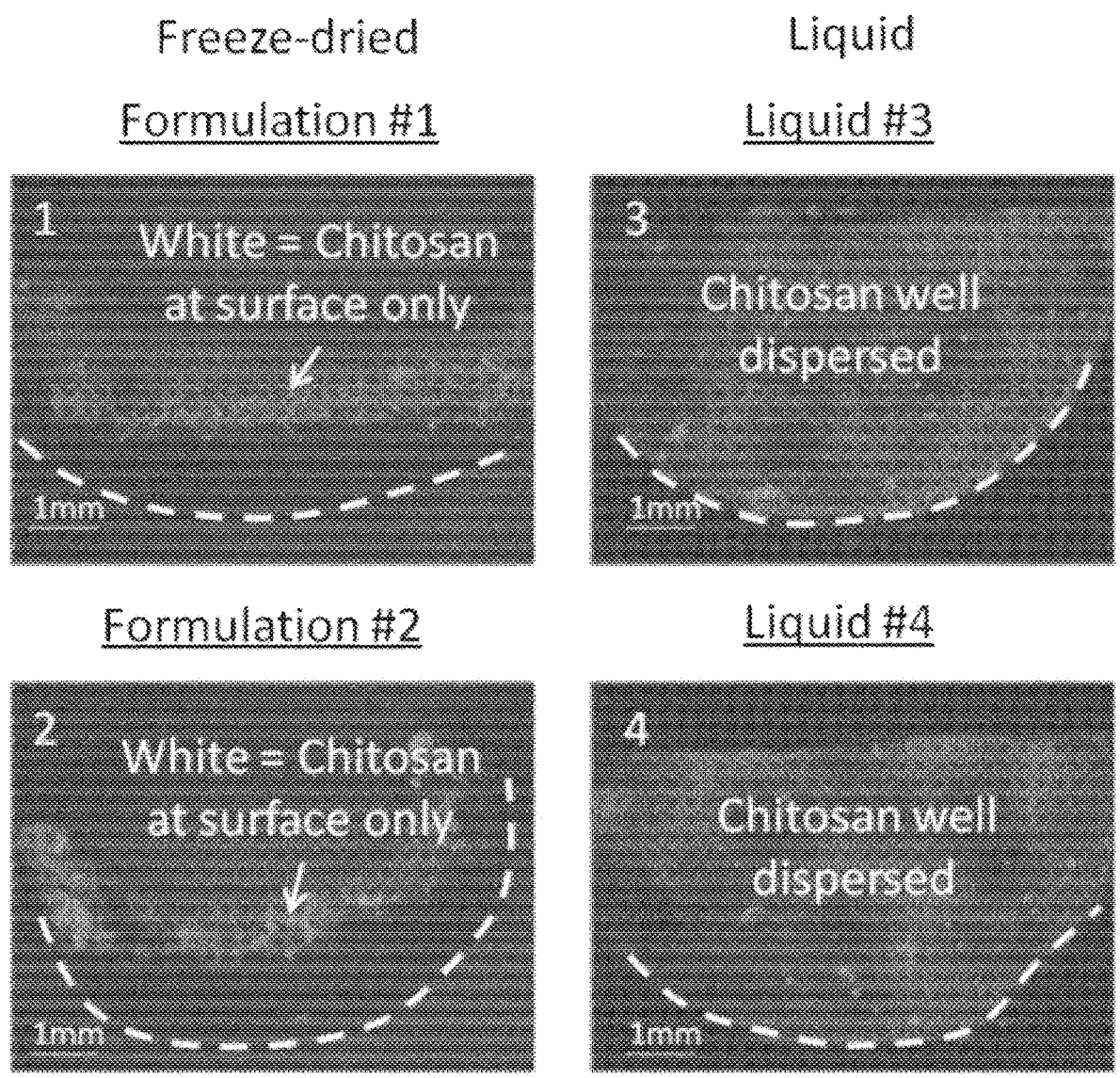

Referring now to FIGS. 3A and 3B, chitosan aggregates were not dispersed throughout the freeze-dried hybrid clots prepared in glass tubes (Formulations #1&2 shown in 3A1 and 3A2 respectively) nor in meniscal defects (Formulations #1&2 shown in 3B1 & and 3B2 respectively). Hybrid clots prepared with liquid solutions were homogenous whether prepared in glass tubes (Liquid formulations #3&4 shown in 3A3 and 3A4 respectively) or in meniscal defects (Liquid formulations #3&4 shown in 3B3 and 3B4 respectively). White dashed lines in 3A1 to 3A4 represent the bottom edge of the hybrid clots in glass tubes. White dashed lines in 3B1 to 3B4 represent the borders of the meniscal defects. Rhodamine-chitosan tracer appears white under epifluorescence. Formulation #1: 0.56% (w/v) CS 80.6% DDA $M_n$ 159 kDa with 130 mM NaCl and 42.2 mM $CaCl_2$; Formulation #2: 0.56% (w/v) CS 80.6% DDA $M_n$ 162 kDa with 2% (w/v) trehalose and 42.2 mM $CaCl_2$; Liquid formulation #3: 0.56% (w/v) CS 80.6% DDA $M_n$ 163 kDa with 42 mM NaCl and 45 mM $CaCl_2$ after mixing with PRP; Liquid formulation #4: 0.56% (w/v) CS 80.6% DDA $M_n$ 145 kDa with 2% (w/v) trehalose and 45 mM $CaCl_2$ after mixing with PRP.

Figure 4A:
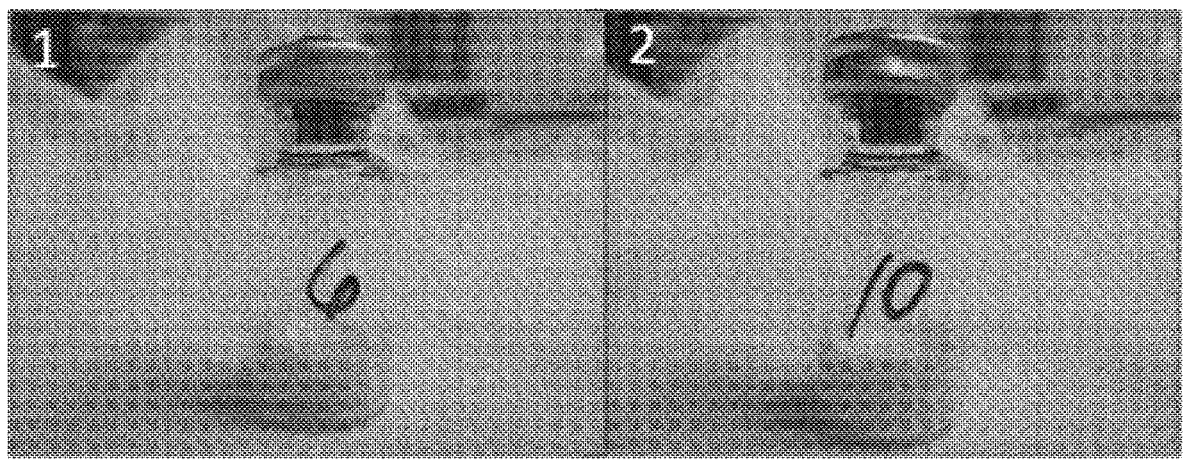
FIGS. 4A and 4B depict freeze-dried chitosan cakes and hybrid clots of Example 4.
Figure 4B:
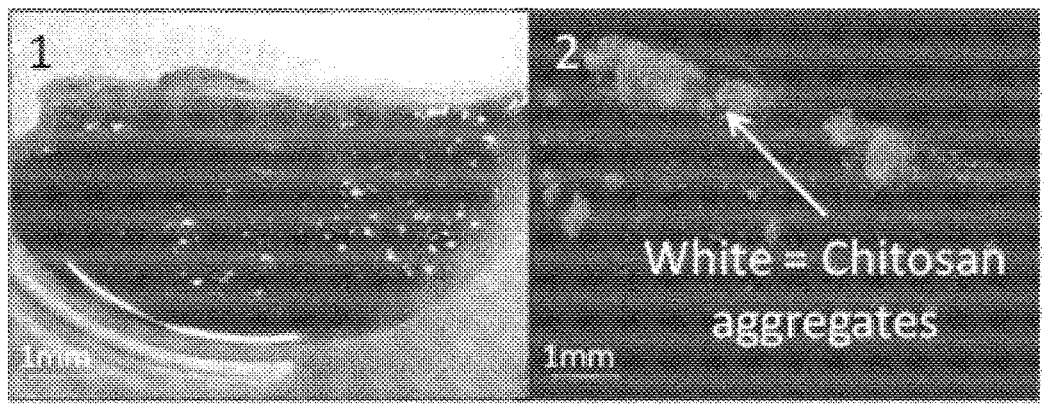
Figure 4B:
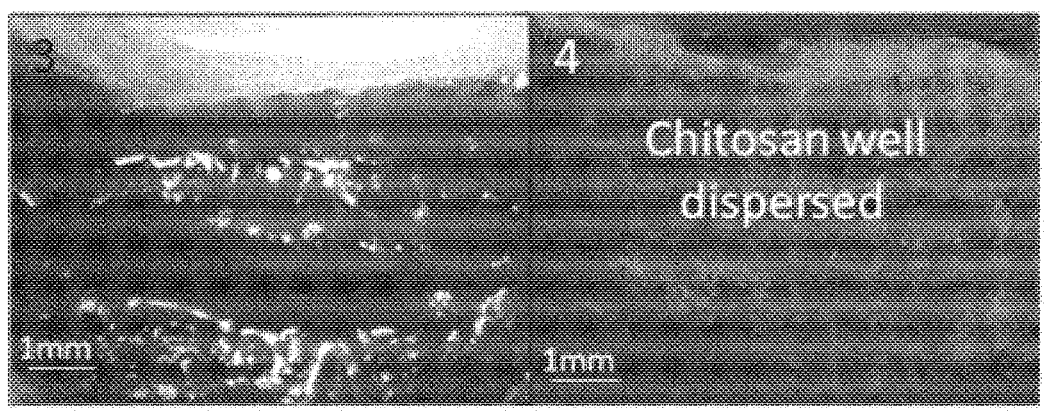
Figure 4B:
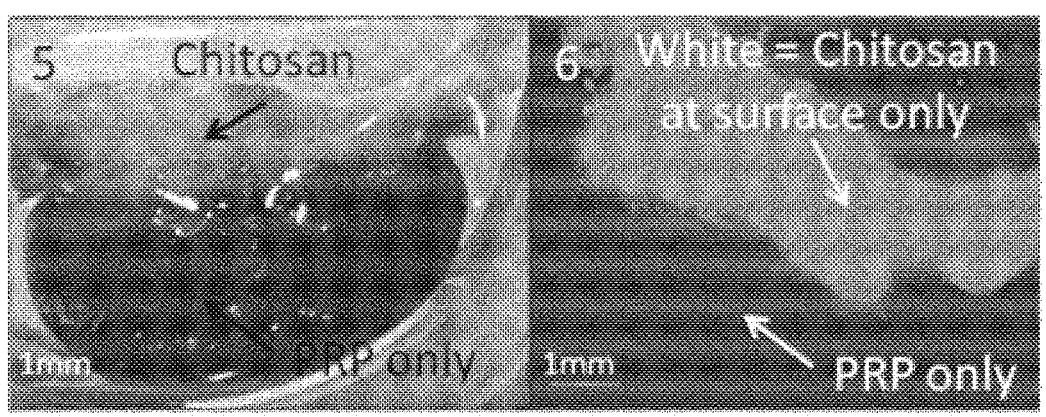

Referring now to FIG. 4A, freeze-dried chitosan cakes were obtained with formulation #6 (4A1) and formulation #10 (4A2). Formulation #6: 0.56% (w/v) CS 80.6% DDA $M_n$ 183 kDa with 6% (w/v) trehalose, 3.8 mM histidine and 42.2 mM $CaCl_2$; Formulation #10: 0.56% (w/v) CS 80.6% DDA $M_n$ 167 kDa with 6% (w/v) mannitol, 3.8 mM histidine and 42.2 mM $CaCl_2$;

Referring now to FIG. 4B, chitosan dispersion in the hybrid clots was homogenous when chitosan of medium $M_n$ was used to prepared the freeze-dried cakes (Formulation #18 with CS 82.5% DDA $M_n$ 38 kDa shown in 4B3 and 4B4), but not when chitosan of high $M_n$ (Formulation #3 with CS 80.6% DDA $M_n$ 131 kDa shown in 4B1 and 4B2) or of low $M_n$ were used (Formulation #23 with CS 84.4% DDA $M_n$ 11 kDa shown in 4B5 and 4B6). Rhodamine-chitosan tracer appears white under epifluorescence in the Figures. Formulation #3: 0.56% (w/v) CS 80.6% DDA $M_n$ 131 kDa with 2% (w/v) trehalose and 42.2 mM $CaCl_2$; Formulation #18: 0.56% (w/v) CS 82.5% DDA $M_n$ 38 kDa with 2% (w/v) mannitol, 3.8 mM histidine and 42.2 mM $CaCl_2$; Formulation #23: 0.56% (w/v) CS 84.4% DDA $M_n$ 11 kDa with 2% (w/v) trehalose and 42.2 mM $CaCl_2$.

Figure 5A:
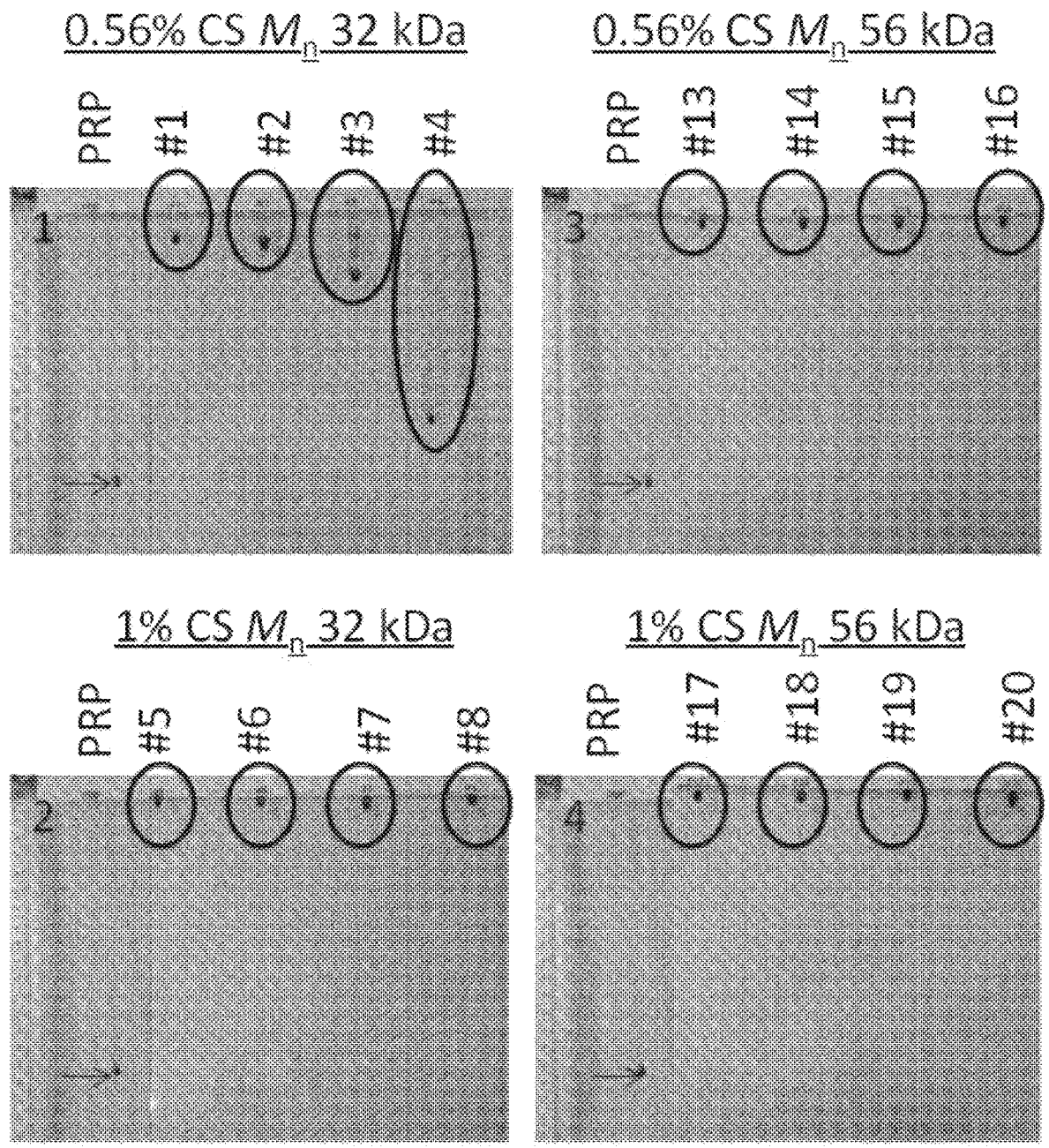
FIGS. 5A and 5B depict runniness test and TEG of varying chitosan formulations of Example 5.

Referring now to FIG. 5A, increasing chitosan concentration from 0.56% (w/v) to 1% (w/v) or chitosan $M_n$ from 32 kDa to 56 kDa improved paste-like properties of freeze-dried formulations according to a runniness test on an inclined plastic plate (compare 5A1 to 5A2 and 5A1 to 5A3). Black arrows in 5A1 to 5A4 point out runniness of PRP without chitosan. Black ovals in 5A1 to 5A4 point out the runniness of different chitosan-PRP formulations.

Figure 5B:
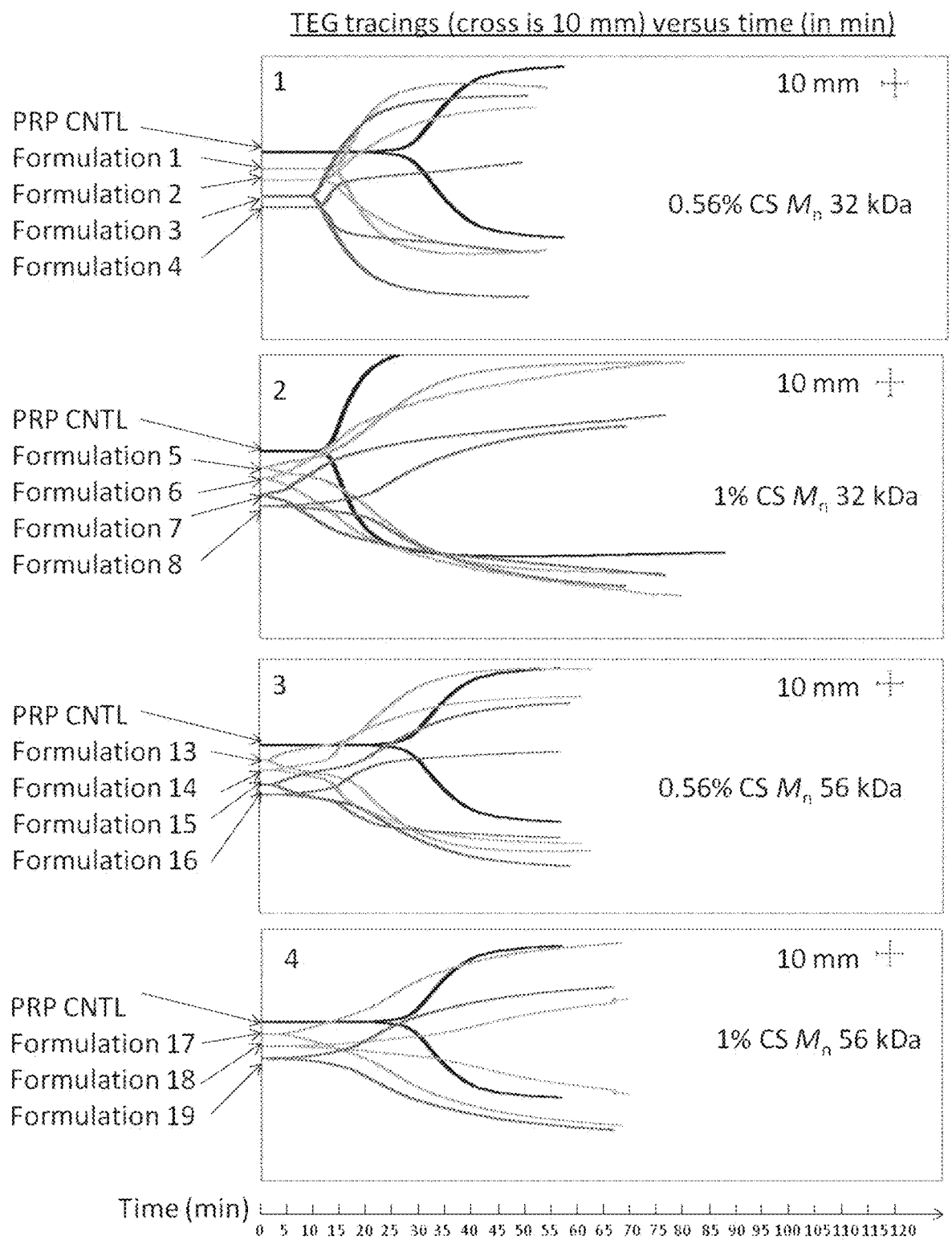

Referring now to FIG. 5B, formulations containing 0.56% (w/v) chitosan $M_n$ 32 kDa clotted in 1-phase fashion similar to PRP only controls (5B1). Increasing chitosan $M_n$ or concentration induced a 2-phase coagulation mechanism as revealed by TEG tracings (5B2 to 5B4). Formulation #1: 0.56% (w/v) CS 81.2% DDA $M_n$ 32 kDa with 2% (w/v) trehalose and 42.2 mM $CaCl_2$; Formulation #2: 0.56% (w/v) CS 81.2% DDA $M_n$ 32 kDa with 6% (w/v) trehalose and 42.2 mM $CaCl_2$; Formulation #3: 0.56% (w/v) CS 81.2% DDA $M_n$ 32 kDa with 2% (w/v) mannitol and 42.2 mM $CaCl_2$; Formulation #4: 0.56% (w/v) CS 81.2% DDA $M_n$ 32 kDa with 6% (w/v) mannitol and 42.2 mM $CaCl_2$; Formulation #5: 1% (w/v) CS 81.2% DDA $M_n$ 32 kDa with 2% (w/v) trehalose and 42.2 mM $CaCl_2$; Formulation #6: 1% (w/v) CS 81.2% DDA $M_n$ 32 kDa with 6% (w/v) trehalose and 42.2 mM $CaCl_2$; Formulation #7: 1% (w/v) CS 81.2% DDA $M_n$ 32 kDa with 2% (w/v) mannitol and 42.2 mM $CaCl_2$; Formulation #8: 1% (w/v) CS 81.2% DDA $M_n$ 32 kDa with 6% (w/v) mannitol and 42.2 mM $CaCl_2$; Formulation #13: 0.56% (w/v) CS 80.1% DDA $M_n$ 56 kDa with 2% (w/v) trehalose and 42.2 mM $CaCl_2$; Formulation #14: 0.56% (w/v) CS 80.1% DDA $M_n$ 56 kDa with 6% (w/v) trehalose and 42.2 mM $CaCl_2$; Formulation #15: 0.56% (w/v) CS 80.1% DDA $M_n$ 56 kDa with 2% (w/v) mannitol and 42.2 mM $CaCl_2$; Formulation #16: 0.56% (w/v) CS 80.1% DDA $M_n$ 56 kDa with 6% (w/v) mannitol and 42.2 mM $CaCl_2$; Formulation #17: 1% (w/v) CS 80.1% DDA $M_n$ 56 kDa with 2% (w/v) trehalose and 42.2 mM $CaCl_2$; Formulation #18: 1% (w/v) CS 80.1% DDA $M_n$ 56 kDa with 6% (w/v) trehalose and 42.2 mM $CaCl_2$; Formulation #19: 1% (w/v) CS 80.1% DDA $M_n$ 56 kDa with 2% (w/v) mannitol and 42.2 mM $CaCl_2$; Formulation #20: 1% (w/v) CS 80.1% DDA $M_n$ 56 kDa with 6% (w/v) mannitol and 42.2 mM $CaCl_2$.

Figure 6A:
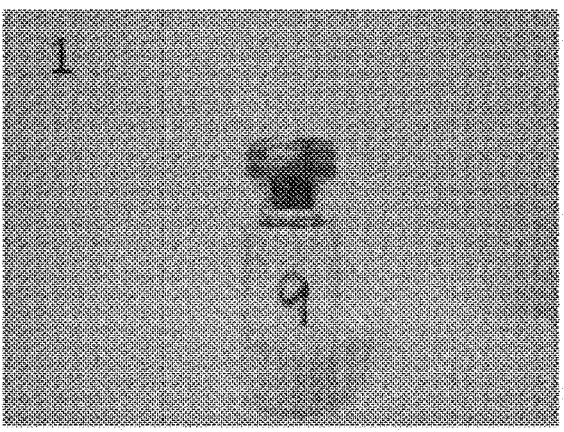
FIG. 6A depicts various freeze-dried chitosan cakes and hybrid clots of Example 6.
Figure 6A:
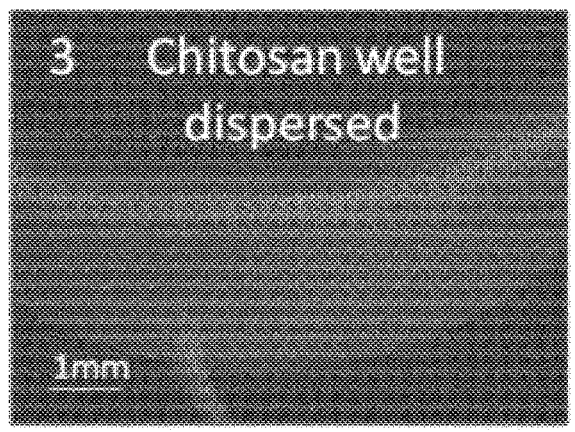
Figure 6A:
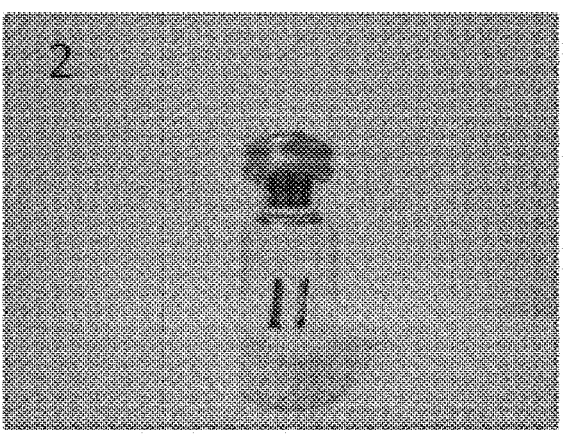
Figure 6A:
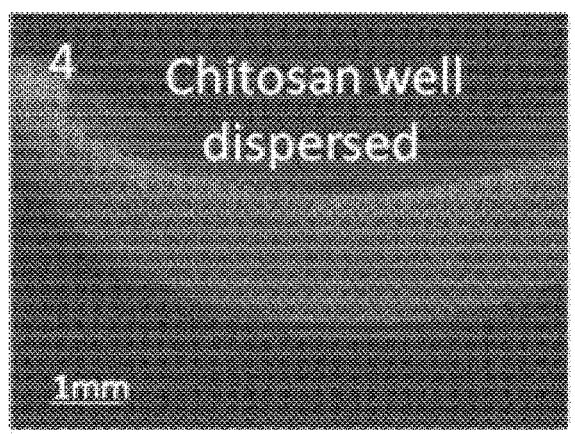

Referring now to FIG. 6A, freeze-dried chitosan cakes were obtained with formulation #9 (6A1) and formulation #11 (6A2). Chitosan dispersion in the hybrid clots was found to be mostly homogenous whether chitosan $M_n$ 28 kDa (6A3) or chitosan $M_n$ 56 kDa (6A4) was used (Formulations #12 and 16 shown in 6A3 and 6A4 respectively). Formulation #9: 1% (w/v) CS 80.5% DDA $M_n$ 28 kDa with 2% (w/v) trehalose and 42.2 mM $CaCl_2$; Formulation #11: 1% (w/v) CS 80.5% DDA $M_n$ 28 kDa with 2% (w/v) mannitol and 42.2 mM $CaCl_2$; Formulation #12: 1% (w/v) CS 80.5% DDA $M_n$ 28 kDa with 6% (w/v) mannitol and 42.2 mM $CaCl_2$; Formulation #16: 1% (w/v) CS 81.8% DDA $M_n$ 56 kDa with 6% (w/v) mannitol and 42.2 mM $CaCl_2$.

Referring now to FIG. 6B, TEG tracings showed a 2-phase coagulation mechanism (6B1 & 6B2). Liquid expression from the hybrid clots was mostly absent (0% liquid expression) with freeze dried chitosan/PRP versus about 80% volume loss with PRP alone (6B3). Formulation #9: 1% (w/v) CS 80.5% DDA $M_n$ 28 kDa with 2% (w/v) trehalose and 42.2 mM $CaCl_2$; Formulation #10: 1% (w/v) CS 80.5% DDA $M_n$ 28 kDa with 6% (w/v) trehalose and 42.2 mM $CaCl_2$; Formulation #11: 1% (w/v) CS 80.5% DDA $M_n$ 28 kDa with 2% (w/v) mannitol and 42.2 mM $CaCl_2$; Formulation #12: 1% (w/v) CS 80.5% DDA $M_n$ 28 kDa with 6% (w/v) mannitol and 42.2 mM $CaCl_2$; Formulation #13: 1% (w/v) CS 80.1% DDA $M_n$ 56 kDa with 2% (w/v) mannitol and 42.2 mM $CaCl_2$; Formulation #14: 1% (w/v) CS 80.1% DDA $M_n$ 56 kDa with 6% (w/v) mannitol and 42.2 mM $CaCl_2$; Formulation #15: 1% (w/v) CS 81.8% DDA $M_n$ 56 kDa with 2% (w/v) mannitol and 42.2 mM $CaCl_2$; Formulation #16: 1% (w/v) CS 81.8% DDA $M_n$ 56 kDa with 6% (w/v) mannitol and 42.2 mM $CaCl_2$.

Figure 6C:
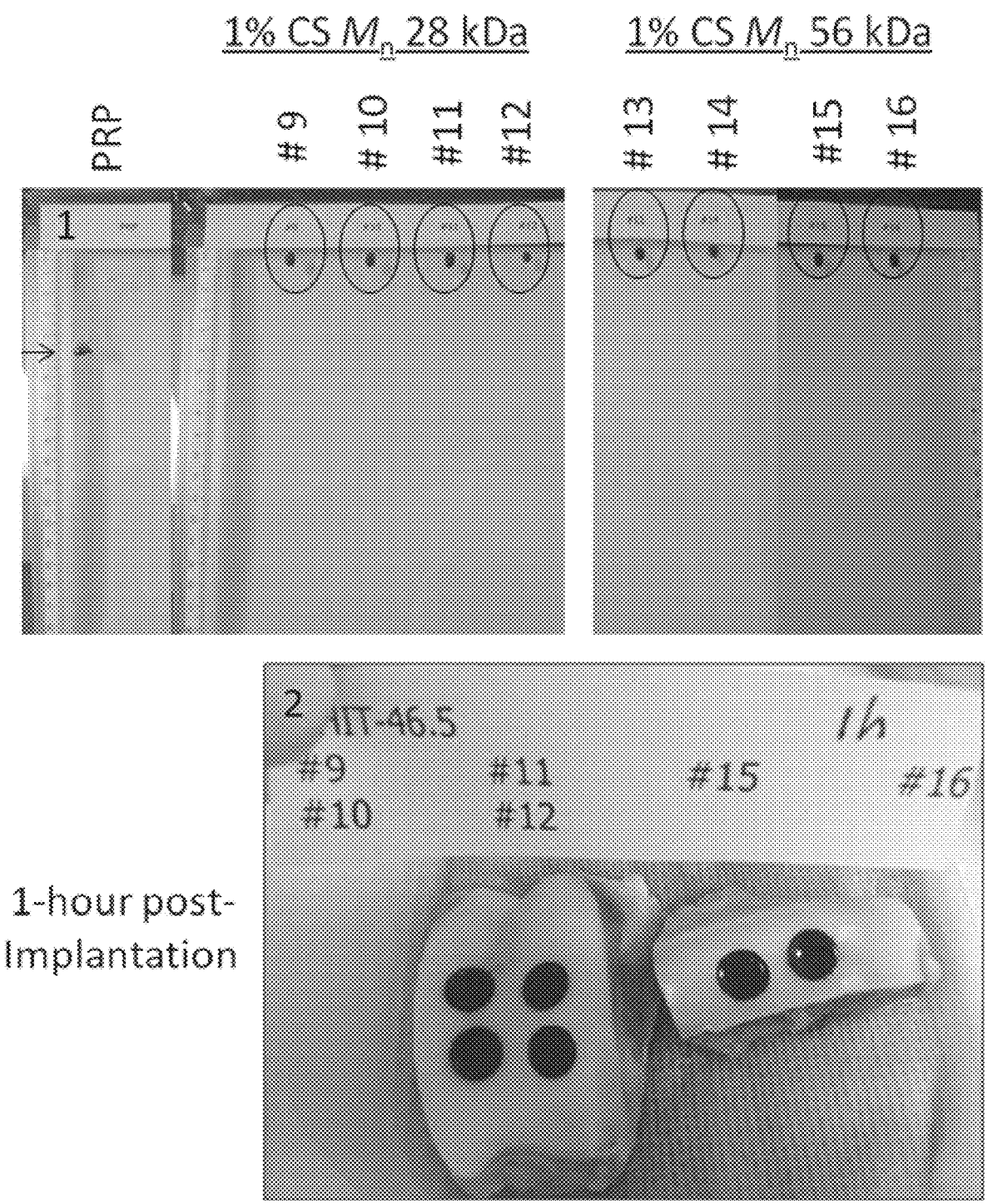
FIG. 6C depicts runniness test and ex vivo implantation of chitosan formulations of Example 6.

Referring now to FIG. 6C, all formulations (#1 to 16) were paste-like compared to PRP (Formulations #9 to 16 shown in 6C1). Black arrows in 6C1 point out runniness of PRP without chitosan. Black ovals in 6C1 point out the runniness of different chitosan-PRP formulations. Hybrid clots were delivered ex vivo to cartilage defects created in pig joints using a syringe equipped with a 20-gauge needle where they solidified (Formulations #9, 10, 11, 12, 15 and 16 shown in 6C2). Formulation #9: 1% (w/v) CS 80.5% DDA $M_n$ 28 kDa with 2% (w/v) trehalose and 42.2 mM $CaCl_2$; Formulation #10: 1% (w/v) CS 80.5% DDA $M_n$ 28 kDa with 6% (w/v) trehalose and 42.2 mM $CaCl_2$; Formulation #11: 1% (w/v) CS 80.5% DDA $M_n$ 28 kDa with 2% (w/v) mannitol and 42.2 mM $CaCl_2$; Formulation #12: 1% (w/v) CS 80.5% DDA $M_n$ 28 kDa with 6% (w/v) mannitol and 42.2 mM $CaCl_2$; Formulation #13: 1% (w/v) CS 80.1% DDA $M_n$ 56 kDa with 2% (w/v) mannitol and 42.2 mM $CaCl_2$; Formulation #14: 1% (w/v) CS 80.1% DDA $M_n$ 56 kDa with 6% (w/v) mannitol and 42.2 mM $CaCl_2$; Formulation #15: 1% (w/v) CS 81.8% DDA $M_n$ 56 kDa with 2% (w/v) mannitol and 42.2 mM $CaCl_2$; Formulation #16: 1% (w/v) CS 81.8% DDA $M_n$ 56 kDa with 6% (w/v) mannitol and 42.2 mM $CaCl_2$.

Figure 6D:
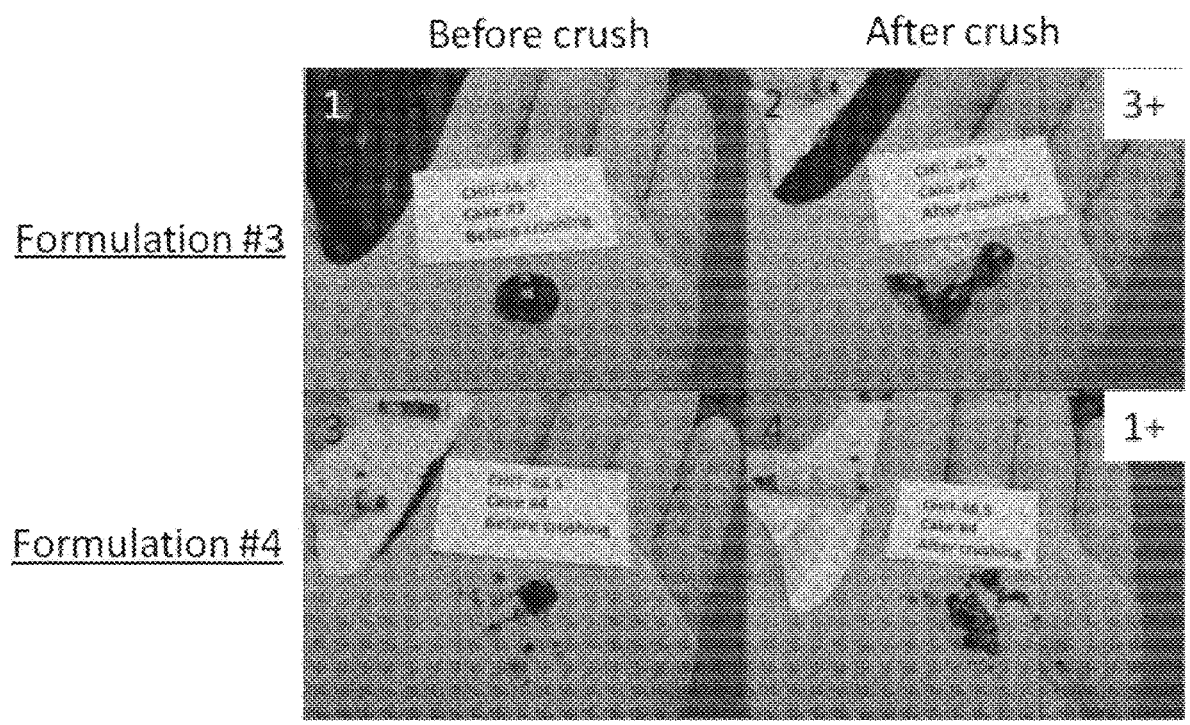
FIG. 6D depicts mechanical strength test of hybrid clots of Example 6.

Referring now to FIG. 6D, hybrid clots containing 2% (w/v) lyoprotectant (Formulation #3 shown in 6D1 and 6D2) had greater mechanical strength compared to hybrid clots prepared with 6% (w/v) lyoprotectant (Formulation #4 shown in 6D3 and 6D4). Formulation #3: 1% (w/v) CS 81.2% DDA $M_n$ 32 kDa with 2% (w/v) mannitol and 42.2 mM $CaCl_2$; Formulation #4: 1% (w/v) CS 81.2% DDA $M_n$ 32 kDa with 6% (w/v) mannitol and 42.2 mM $CaCl_2$.

Referring now to FIG. 7A, hybrid clots were prepared without the aid of stainless steel beads (7A1 to 7A4) and by mixing with three 0.39 g stainless steel beads (7A5 to 7A8). Formulation #15: 0.56% (w/v) CS 80.6% DDA $M_n$ 41 kDa with 2% (w/v) mannitol and 42.2 mM $CaCl_2$; Formulation #19: 1% (w/v) CS 80.6% DDA $M_n$ 41 kDa with 2% (w/v) mannitol and 42.2 mM $CaCl_2$; Formulation #23: 0.56% (w/v)cS 80.6% DDA $M_n$ 89 kDa with 2% (w/v) mannitol and 42.2 mM $CaCl_2$; Formulation #27: 1% (w/v) CS 80.6% DDA $M_n$ 108 kDa with 2% (w/v) mannitol and 42.2 mM $CaCl_2$.

Referring now to FIG. 7B, results for crush test, % liquid expression, runniness and maximal amplitude for formulations reconstituted without and with steel beads and for PRP control from 2 different donors are depicted in 7B. Formulation #15: 0.56% (w/v) CS 80.6% DDA $M_n$ 41 kDa with 2% (w/v) mannitol and 42.2 mM $CaCl_2$; Formulation #19: 1% (w/v) CS 80.6% DDA $M_n$ 41 kDa with 2% (w/v) mannitol and 42.2 mM $CaCl_2$; Formulation #23: 0.56% (w/v)cS 80.6% DDA $M_n$ 89 kDa with 2% (w/v) mannitol and 42.2 mM $CaCl_2$; Formulation #27: 1% (w/v) CS 80.6% DDA $M_n$ 108 kDa with 2% (w/v) mannitol and 42.2 mM $CaCl_2$.

Figure 7C:
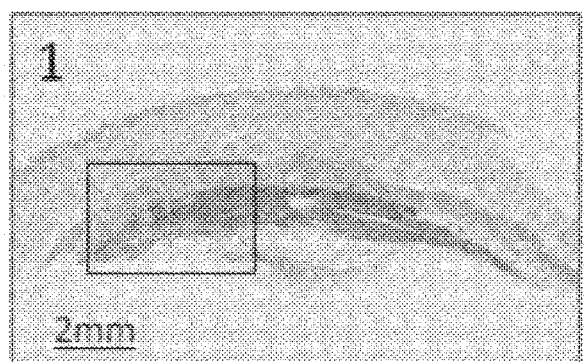
FIG. 7C depicts Day 1 histological results of freeze-dried chitosan/PRP implants injected in NZW rabbits of Example 7.
Figure 7C:
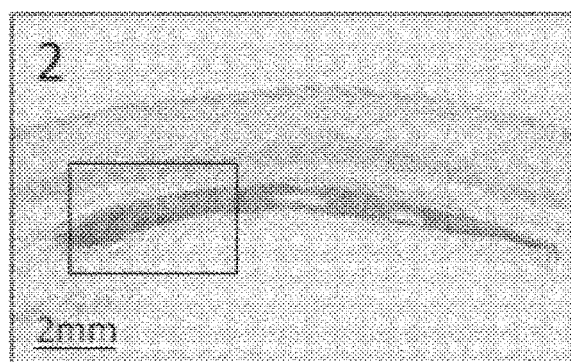
Figure 7C:
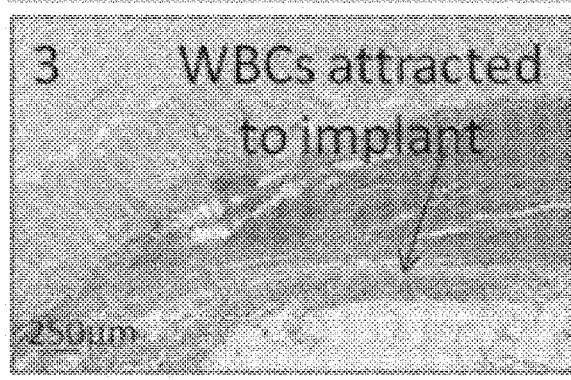
Figure 7C:
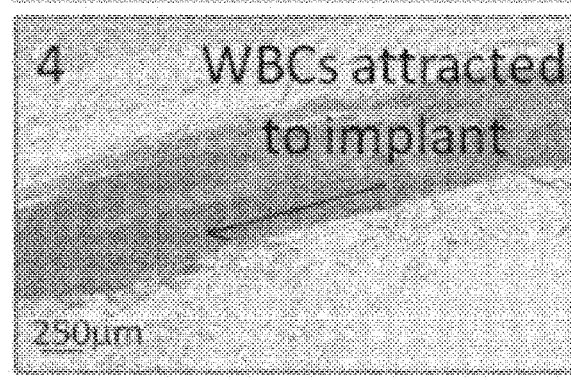
Figure 7C:
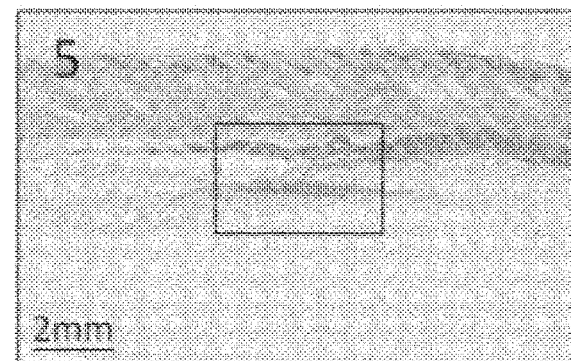
Figure 7C:
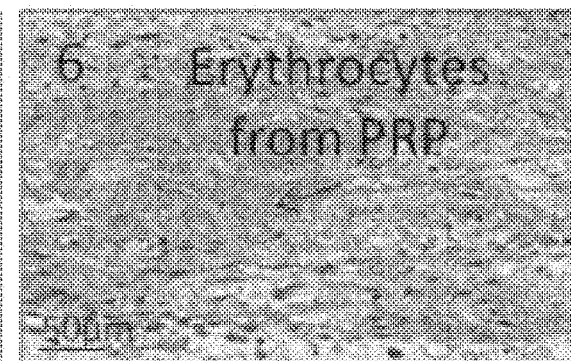

Referring now to FIG. 7C, subcutaneous freeze-dried chitosan/PRP implants injected into the backs of NZW rabbits showed leukocyte chemotaxis towards the implants at 1 day (7C1, 7C2, 7C3 and 7C4) post-injection. PRP-only controls attracted much less leukocytes at 1 day (7C5 and 7C6) post-injection. Formulation #13: 0.56% (w/v) CS 80.6% DDA $M_n$ 41 kDa with 2% (w/v) trehalose and 42.2 mM $CaCl_2$; Formulation #14: 0.56% (w/v) CS 80.6% DDA $M_n$ 41 kDa with 6% (w/v) trehalose and 42.2 mM $CaCl_2$.

Figure 7D:
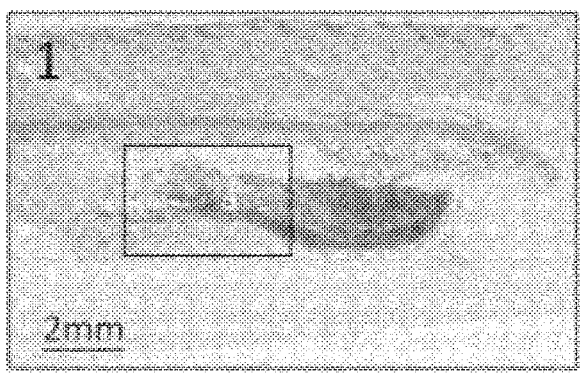
FIG. 7D depicts Day 3 histological results of freeze-dried chitosan/PRP implants injected in NZW rabbits of Example 7.
Figure 7D:
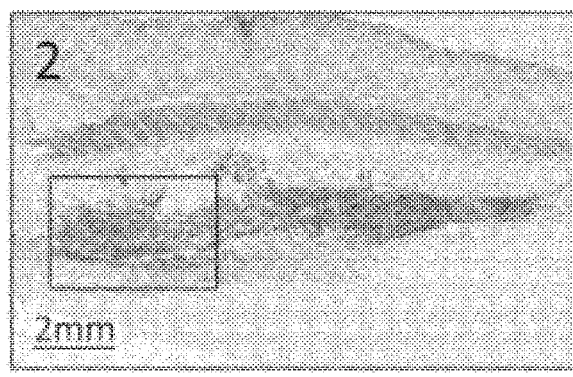
Figure 7D:
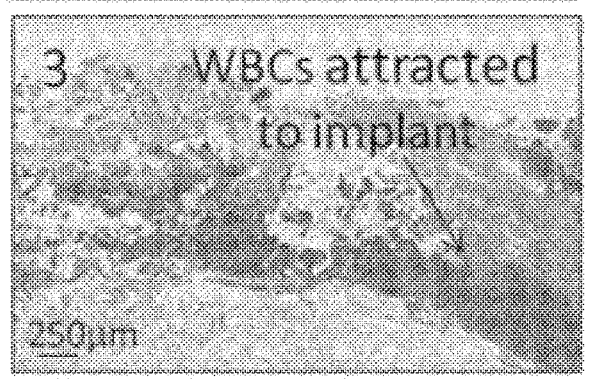
Figure 7D:
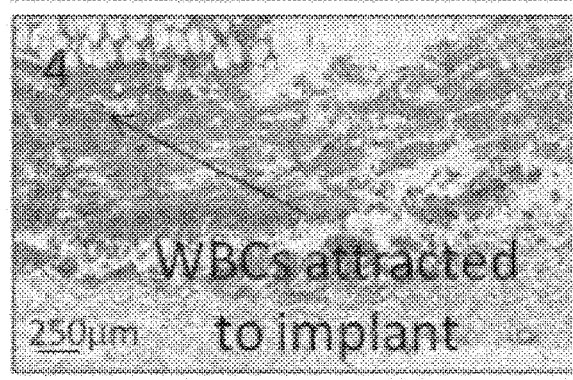
Figure 7D:
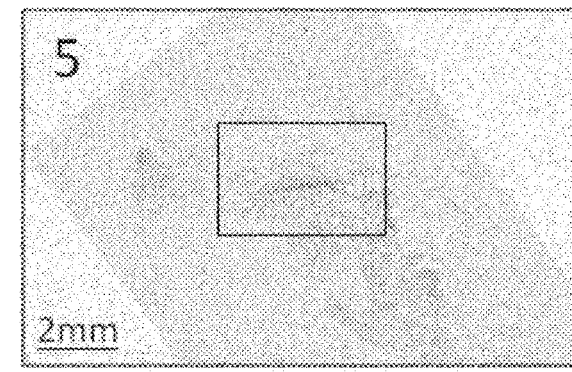
Figure 7D:
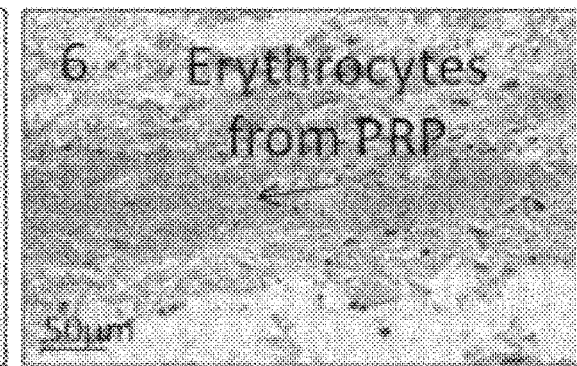

Referring now to FIG. 7D, subcutaneous freeze-dried chitosan/PRP implants injected into the backs of NZW rabbits showed leukocyte chemotaxis towards the implants at 3 days (7D1, 7D2, 7D3 and 7D4) post-injection. PRP-only controls attracted much less leukocytes at 3 days (7D5 and 7D6) post-injection. Formulation #13: 0.56% (w/v) CS 80.6% DDA $M_n$ 41 kDa with 2% (w/v) trehalose and 42.2 mM $CaCl_2$; Formulation #14: 0.56% (w/v) CS 80.6% DDA $M_n$ 41 kDa with 6% (w/v) trehalose and 42.2 mM $CaCl_2$.

Figure 7E:
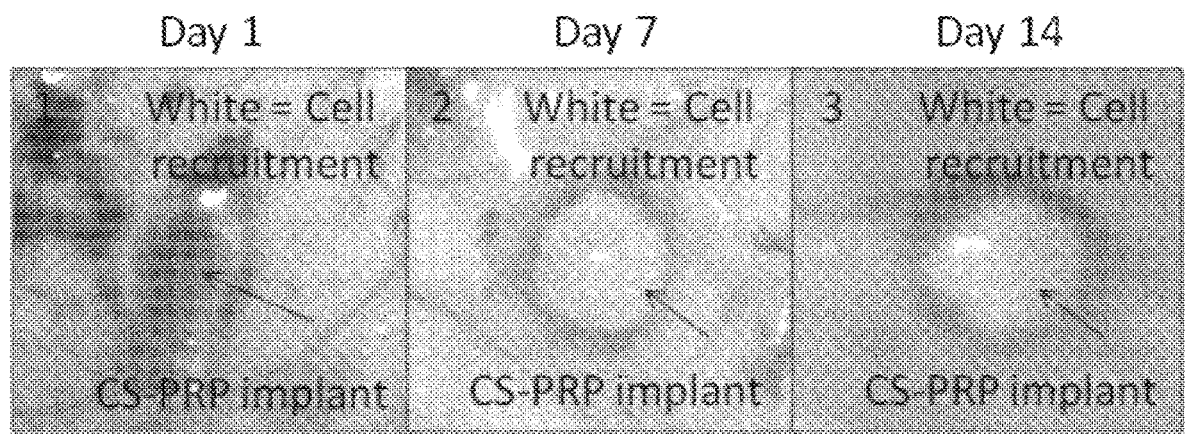
FIG. 7E depicts macroscopic results of freeze-dried chitosan/PRP implants injected in NZW rabbits of Example 7.
Figure 7E:
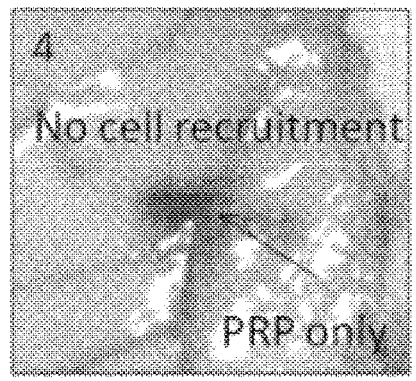

Referring now to FIG. 7E, freeze-dried chitosan/PRP hybrids were retained in vivo for at least 14 days post-implantation (7E1, 7E2 and 7E3) while recalcified PRP controls are present only until 3 days post-implantation (7E4 shows PRP control at day 1). Formulation #13: 0.56% (w/v) CS 80.6% DDA $M_n$ 41 kDa with 2% (w/v) trehalose and 42.2 mM $CaCl_2$; Formulation #14: 0.56% (w/v) CS 80.6% DDA $M_n$ 41 kDa with 6% (w/v) trehalose and 42.2 mM $CaCl_2$.

Figure 8A:
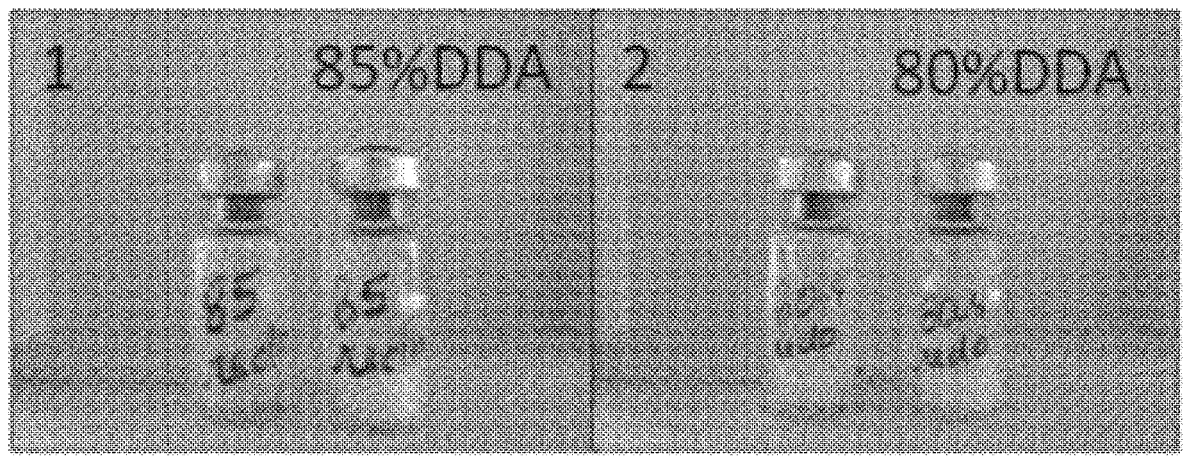
FIG. 8A depicts cake appearance and solubility of various freeze-dried chitosan cakes of Example 8.
Figure 8A:
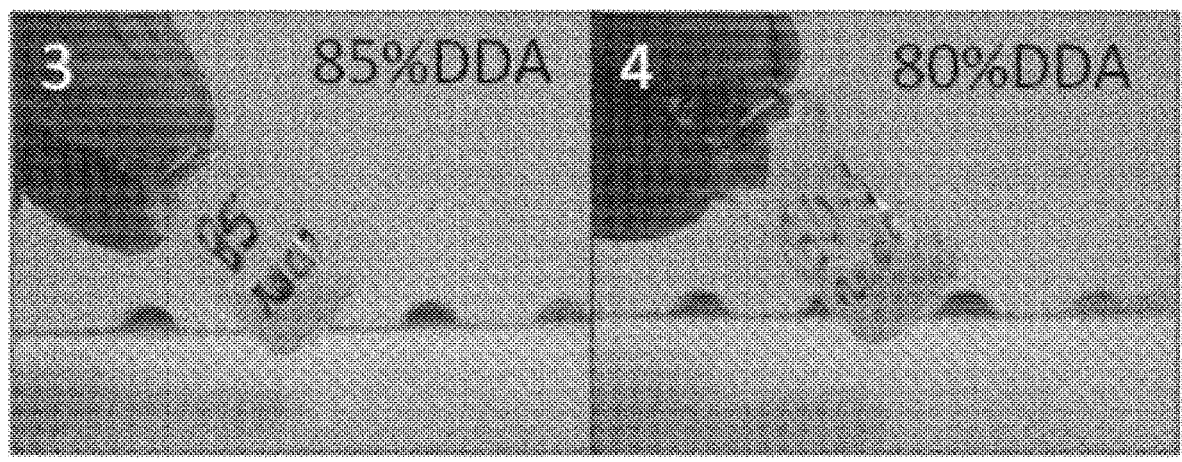

Referring now to FIG. 8A, freeze-dried chitosan cakes were obtained with CS $M_n$ 43 kDa and 85% DDA (8A1) and CS $M_n$ 36 kDa and 80% DDA (8A2) with 1% (w/v) CS concentration and 1% (w/v) trehalose concentration. Freeze dried chitosan cakes were completely soluble when mixed (8A3 & 8A4).

Figure 8B:
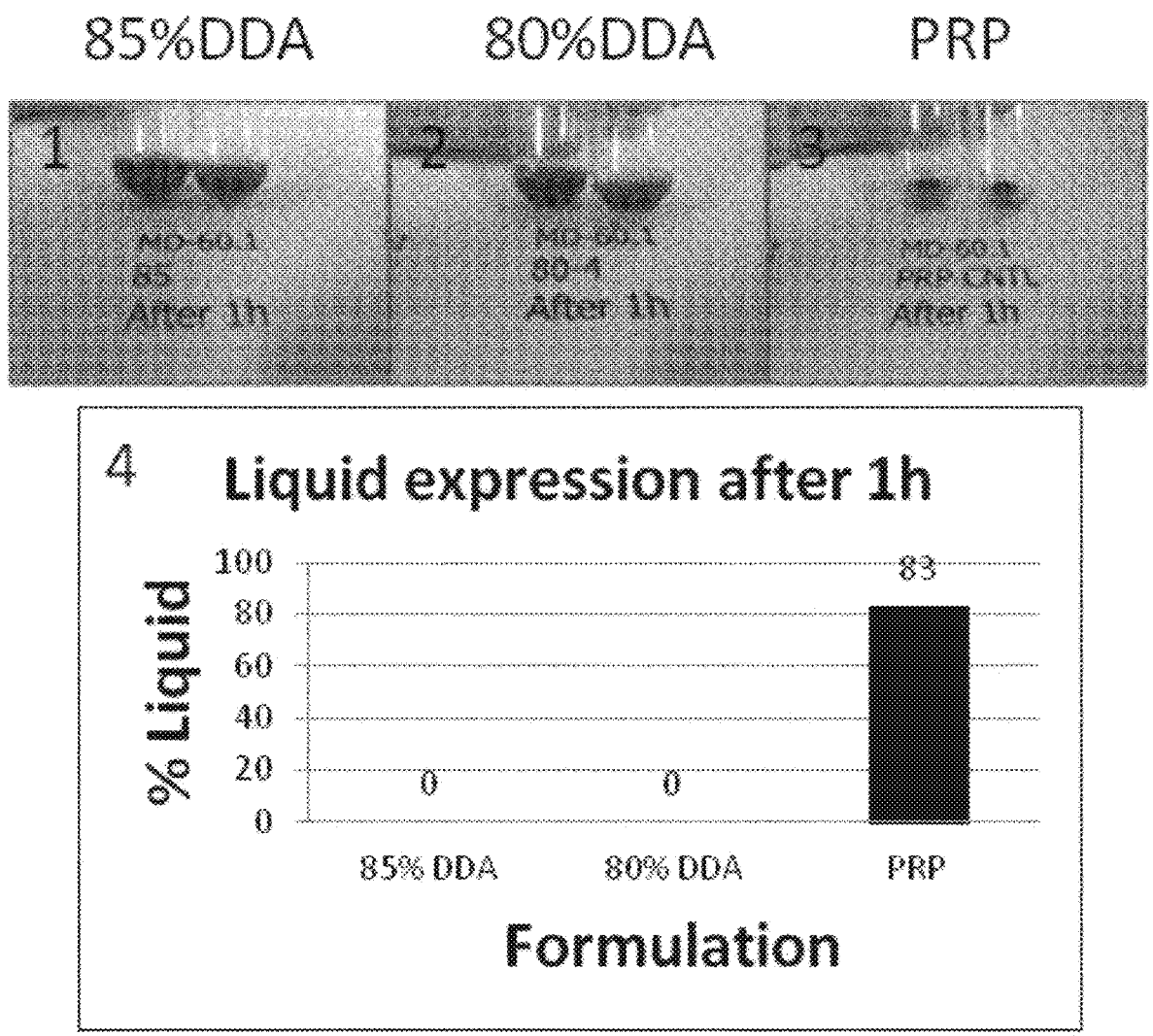
FIG. 8B depicts liquid expression testing of various freeze-dried chitosan cakes of Example 8.

Referring now to FIG. 8B, chitosan/PRP hybrids expressed no liquid, while PRP only controls expressed more than 80% their weight in serum (8B1, 8B2, 8B3 and 8B4).

Figure 8C:
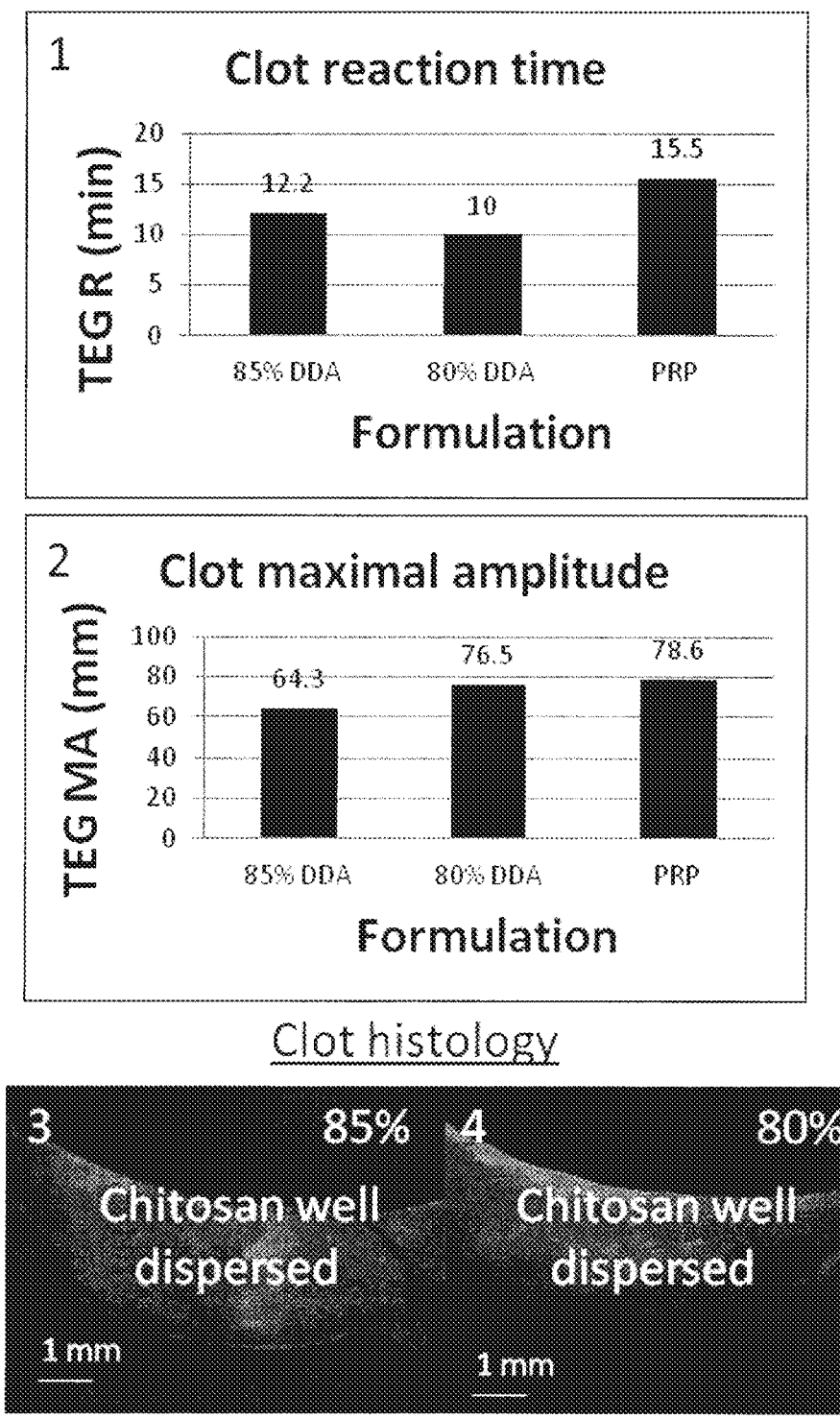
FIG. 8C depicts TEG testing and clot histology of various freeze-dried chitosan cakes of Example 8.

Referring now to FIG. 8C, chitosan/PRP hybrids had decreased clot reaction time and clot maximal amplitude as measured by thromboelastography (8C1 and 8C2). CS dispersion in hybrid clots was homogenous (8C3 and 8C4).

Figure 8D:
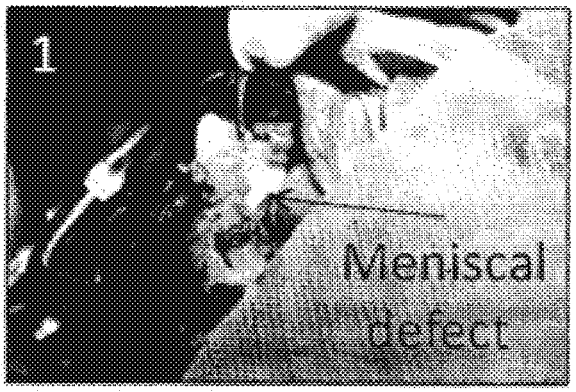
FIG. 8D depicts the application of chitosan/PRP hybrids to surgical meniscal defects of Example 8.
Figure 8D:
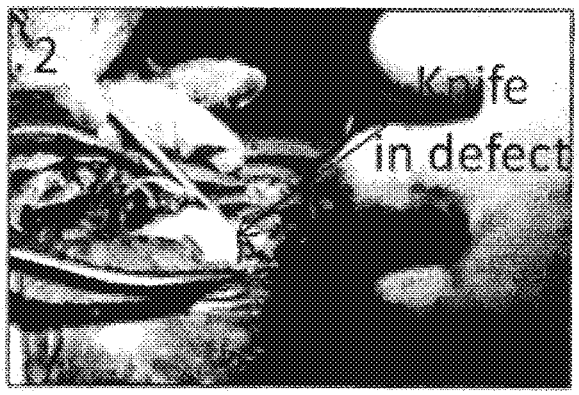
Figure 8D:
Figure 8D:
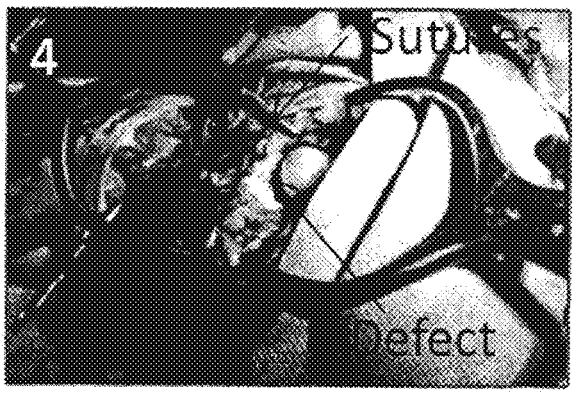
Figure 8D:
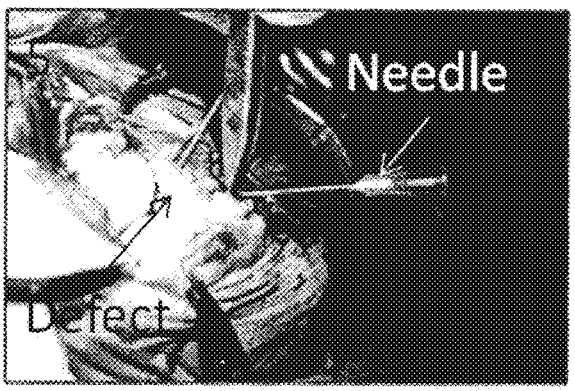
Figure 8D:
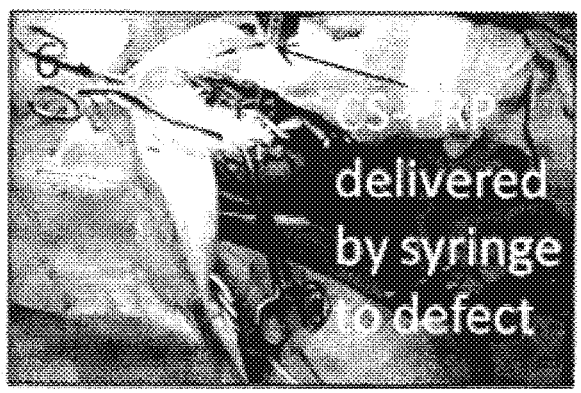

Referring now to FIG. 8D, surgical defects were created in the anterior portion of the medial meniscus in sheep using a scalpel blade (8D1). The defects were elongated to 10-mm length (8D2). The defects were rasped (8D3). The defects were sutured without tightening and 18-gauge needles were pre-placed to create trephination channels from the periphery of the meniscus to the tear (8D4 and 8D5). Chitosan/PRP hybrids were delivered to the meniscus tear through the trephination channels (8D6).

Figure 8E:
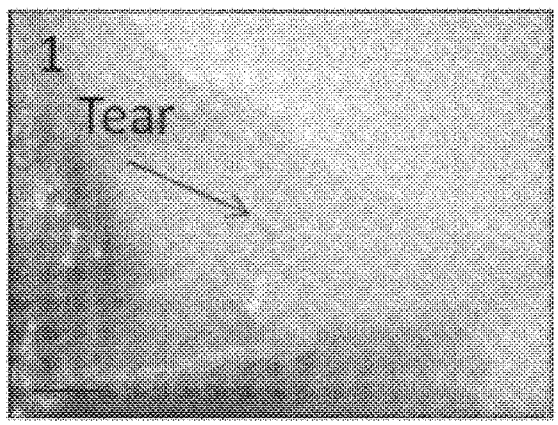
FIG. 8E depicts day 1 and day 21 results following implantation of chitosan/PRP hybrids to meniscal defects of Example 8.
Figure 8E:
Figure 8E:
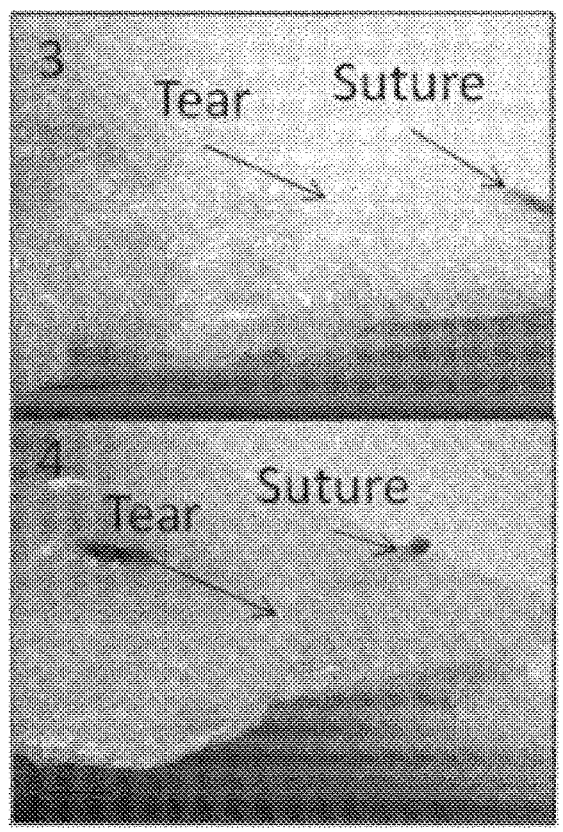
Figure 8E:
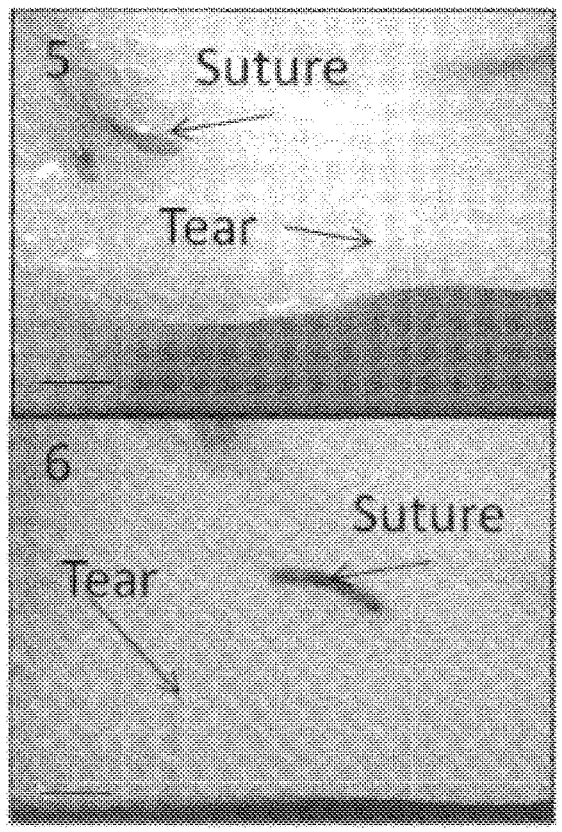

Referring now to FIG. 8E, chitosan/PRP hybrids were resident in the tears for at least 24 hours post-surgery (8E1 and 8E2). At 21 days, post-surgery the edges of the meniscus tears treated with chitosan/PRP hybrids were well apposed (8E3 and 8E4).

Figure 9A:
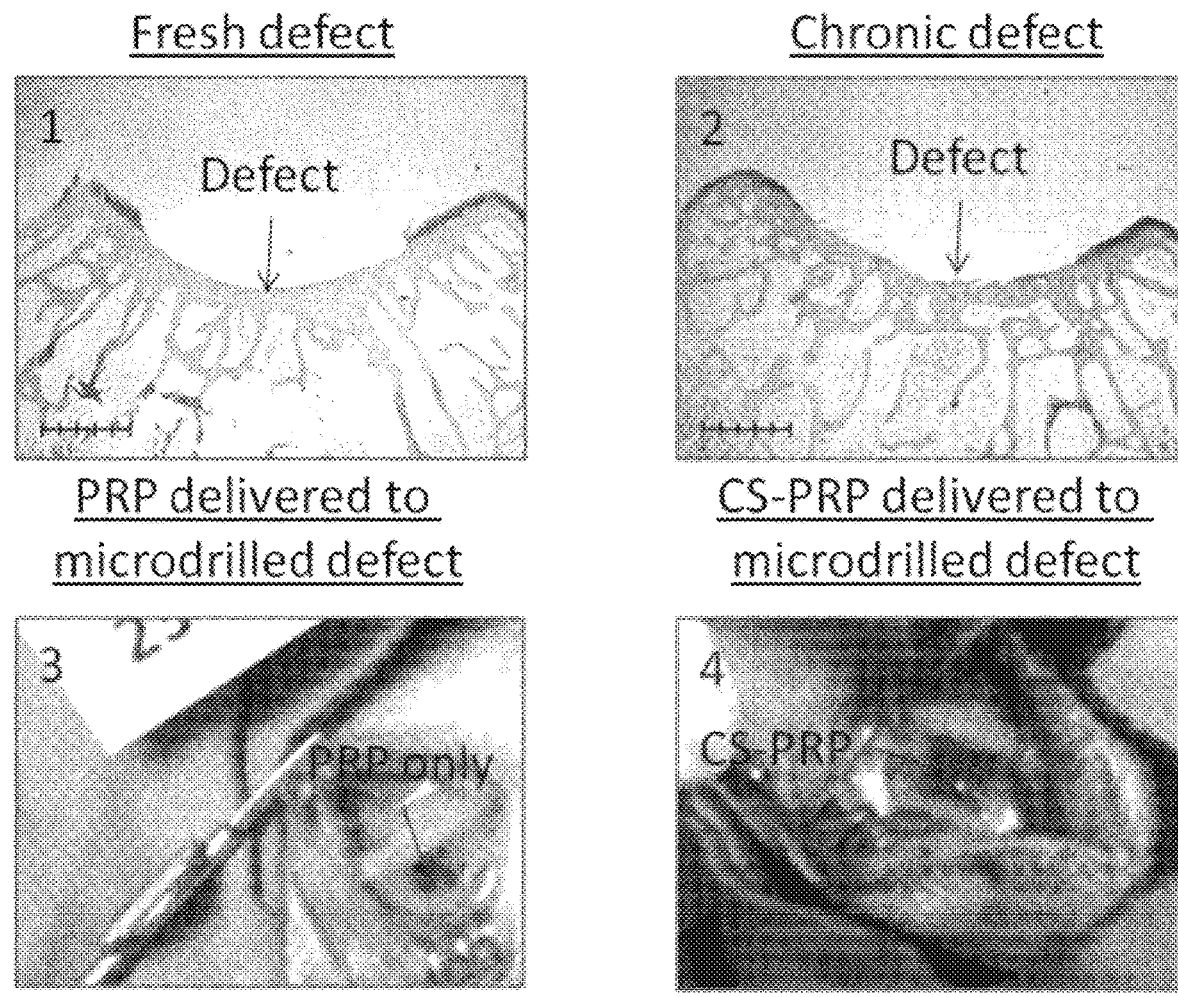
FIG. 9A depicts implantation of chitosan/PRP implants in chronic cartilage defects of Example 9.

Referring now to FIG. 9A, cartilage-only defects of 4 mm×4 mm were created on the trochlea of NZW rabbits (9A1). The knees were closed and the defects were allowed to develop to chronic stage for 1 month (9A2). The defects were debrided and 4 microdrill holes of 0.9 mm diameter were pierce through the subchondral bone to a depth of ~4 mm. One knee was treated by injecting the Chitosan/PRP implant (CS $M_n$ 40 kDa and 80% DDA with 1% (w/v) CS concentration and 2% (w/v) trehalose concentration) on top of the microdrilled defect (9A4). The contralateral knee was treated by injecting recalcified PRP as control on top of the microdrilled defect (9A3).

Figure 9B:
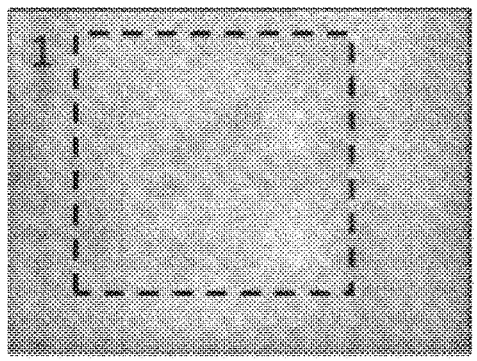
FIG. 9B depicts day 21 results following implantation of chitosan/PRP hybrids in chronic cartilage defects of Example 9.
Figure 9B:
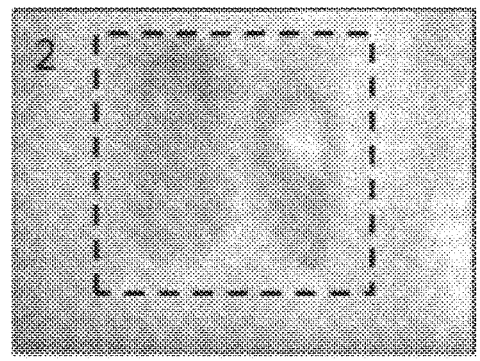
Figure 9B:
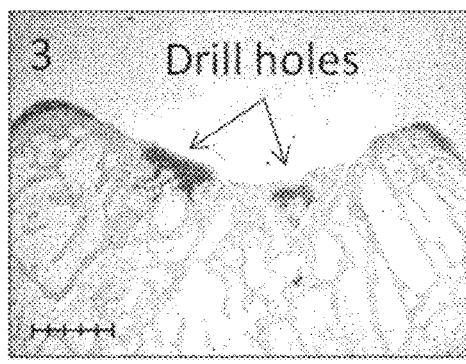
Figure 9B:
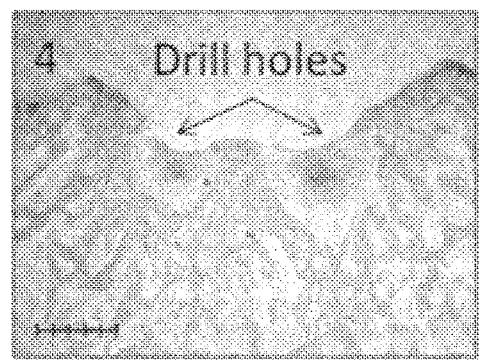

Referring now to FIG. 9B, evaluation of the macroscopic appearance of the defects (9B1 and 9B2) and histological assessment (9B3 and 9B4) were done after 21 days of healing. Black dashed squares in 9B1 and 9B2 show the borders of the chronic cartilage defect.

DETAILED DESCRIPTION

In a preferred embodiment, in one procedure, room temperature chitosan was weighed into 15 mL Falcon tubes and ddH$_2$O and HCl 1N were added to each tube. Chitosan concentration ranged between 0.42% to 2% (w/v). HCl concentration ranged between 12 and 57 mM. The tubes were placed on a rotator and stirred overnight at room temperature to ensure complete dissolution.

Two sterilization methods were used for sterilization of the chitosan solution: 1) Autoclave for 10 minutes for chitosan $M_n$>100 kDa or 2) Filtration for chitosan $M_n$<100 kDa.

Under a laminar flow hood, filter-sterilised 270 mM CaCl$_2$ was added to the chitosan solution to a final concentration of 45 mM or of 42.2 mM. Filter-sterilised 15% (w/v) trehalose, mannitol or autoclaved 20% (w/v) sucrose, trehalose were added as required resulting in a lyoprotectant concentration ranging between 0 to 10% (w/v). Autoclaved 5 M NaCl was added as required to achieve a final concentration between 130 and 201 mM. Filter-sterilised histidine was added as required to achieve a final concentration of 3.8, 33 or 39 mM. A filter-sterilised rhodamine-chitosan tracer was added to a final ratio of 0.01% (vol tracer/vol solution) for imaging purposes.

After mixing well with a vortex until a homogeneous solution was achieved, 1 mL aliquots were distributed into 3 mL or 10 mL glass vials for freeze-drying using a membrane on top of the vials to maintain sterility. Alternatively, smaller 300 μL aliquots were distributed into 2 mL glass vials for freeze-drying. The freeze-drying cycle consisted of: 1) Ramped freezing to −40° C. in 1 hour then isothermal 2 hours at −40° C., 2) −40° C. for 48 hours and 3) Ramped heating to 30° C. in 12 hours then isothermal 6 hours at 30° C., at 300 or 100 millitorrs. Cakes were visually assessed post-lyophilization. As per Criteria 1 above, freeze-dried cakes should be homogenous, solid and present good mechanical properties for storage and shipping.

Anti-coagulated whole blood was collected from rabbit, sheep and human donors and placed in Vacutainer tubes. The anti-coagulant was either acid citrate dextrose (13 mM trisodium citrate dihydrate; 7 mM citric acid; 24 mM dextrose in blood) or sodium citrate (12.9 mM trisodium citrate dihydrate in blood).

The Vacutainer tubes containing anti-coagulated whole blood were centrifuged in an ACE E-Z PRP™ centrifuge at 160 g for 10 minutes at room temperature. The supernatant was collected along with the first about 2 mm of erythrocytes and centrifuged again at 400 g for 10 minutes at room temperature in order to separate the platelet-rich plasma (bottom 1.5 mL in the tube, classified as a Leukocyte-PRP, also containing a fraction of erythrocytes) and platelet-poor plasma (clear plasma).

To test cake reconstitution and chitosan solubilisation, 1 mL of PRP or PPP (preferable for visual assessment because it is clear versus PRP which contains erythrocytes) was pipetted into each vial containing freeze-dried cake. Mixing was done by swirling or by shaking vigorously for 10 seconds in the presence or absence of three 0.39 g stainless steel balls. The ease of cake solubilisation was recorded. As per Criteria 2 above, cakes should be rapidly and easily reconstituted in PRP, PPP, blood or water, as required. pH and osmolality of reconstituted mixtures were also recorded to determine whether they are close to physiological. As per Criteria 8 above, the reconstituted mixtures should have close-to-physiological properties for in vivo implantation or intra-articular injections To test cake performance, 1 mL of PRP was pipetted into each vial containing freeze-dried cake. Mixing was done by swirling or by shaking vigorously for 10 seconds in the presence or absence of three 0.39 g stainless steel balls.

Coagulation properties were measured by loading 360 μL of each formulation into a TEG cup immediately after reconstitution and recording TEG tracings for 1 hour. As per Criteria 3 above, coagulation should not be inhibited when gelation in situ is required.

Mechanical properties of the formulations were assessed with a manual crush test. After 1 hour of clotting, each hybrid clot was subjected to manual crushing and mechanical strength scored on a scale of 0 (weak) to 4+(strong). As per Criteria 4 above, the chitosan/PRP hybrid implants should be mechanically stable to withstand loading at implantation sites.

Hybrid clot volume retention was assessed by dispensing the reconstituted formulations into glass tubes at 37° C. After 60 minutes, liquid expression from the hybrid clots was quantified by weight measurement. As per Criteria 5 above, the chitosan/PRP hybrid implants should be able to fill tissue defects without undergoing platelet-mediated retraction.

Chitosan dispersion versus aggregation in hybrid clots was assessed by histology. For example, hybrid clots containing the rhodamine-chitosan tracer were fixed in 10% Neutral Buffered Formalin (NBF) and thick razor blade sections were observed with epifluorescence microscopy. Hybrid clots were fixed in 10% NBF (neutral buffered formalin) and 5 μm paraffin sections were collected for Safranin O/Fast Green staining. As par Criteria 6 above, good mixing must be achieved without phase separation of the polymer and blood components to ensure optimal in vivo responses and timely biodegradability.

Paste-like properties of the formulations were assessed with a runniness test. Runniness was assessed by placing a 30 μL drop of each formulation onto a rigid piece of plastic fixed at a certain angle (38 degrees) immediately after reconstitution and taking pictures at fixed times. As per Criteria 7 above, the mixtures should have appropriate handling properties which would be viscous and paste-like for tissue repair applications or a viscous suspension in the case of intra-articular viscosupplementation.

Handling properties of the formulations were tested ex vivo in a meniscal defect model. For example, a straight razor blade was used to take ~0.5 mm cross-sections from pig meniscus and a horizontal flap was created towards the femoral (top) surface of the meniscus. A 4 mm biopsy punch was used to create a partial thickness defect towards the tibial (bottom) surface of the meniscus. The menisci were wrapped in humid plastic film and were placed at 37° C. for at least 30 min before the start of the experiment. Freeze-dried chitosan formulations reconstituted with PRP were injected into the partial-thickness meniscus defects using a syringe fitted with a 20-gauge needle and the flap was closed immediately. The menisci were immediately re-wrapped and sealed with humid plastic film and were placed at 37° C. for 1 hour. The menisci were fixed in 10% NBF and thick razor blade sections were observed with epifluorescence microscopy. Paraffin sections were stained with Safranin O/Fast Green.

Handling properties of the formulations were tested ex vivo in a cartilage defect model. Biopsy punches (8 mm dia.) and flat surgical blades were used to create cartilage defects in pig condyles and trochlea. The joints were placed in a humid chamber at 37° C. for at least 30 min before the start of the experiment. Freeze-dried chitosan formulations reconstituted in PRP were injected into the cartilage defects using a syringe and 20-gauge needle. The joints were immediately sealed in the humid chamber and were placed at 37° C. for 1 hour. The joints were then inspected to determine whether clotting occurred in situ.

In another embodiment, to test in vivo clearing of the freeze-dried formulations, chondral defects of 3.5 mm×4.5 mm were created bi-laterally in the trochlea of two 19-month old NZW rabbits. Four microdrill holes were pierced through the subchondral bone with a 0.9 mm drill bit to a depth of about 4 mm. Autologous PRP was prepared from rabbit blood extracted immediately prior to surgery. After creation of the defect, the freeze-dried chitosan cake was reconstituted with 1 mL PRP using the bead mixing method and the implant (1 hanging drop) was delivered over the defect site and allowed to solidify in situ for ~5 min before closing the knee. On the contralateral knee, the freeze-dried chitosan was mixed with 1 mL fresh blood collected immediately prior to reconstitution and delivery. Implant residency was assessed at 10 days and at 21 days.

In another embodiment, a second rabbit model allowing for the simultaneous testing of several different chitosan formulations was used to test in vivo biodegradability. Autologous PRP was prepared from rabbit blood extracted immediately prior to surgery. Each freeze-dried cake was reconstituted in 300 μL PRP without the aid the bead mixing and injected subcutaneously in the back of the rabbits using a syringe fitted with a SubQ needle. Controls were recalcified PRP without chitosan. Implant residency and cell recruitment were assessed at 1, 3, 7 and 14 days post-injection.

In another embodiment, a sheep meniscus repair model was used to test hybrid implant retention and effect of implants on meniscal tissue repair. Hybrid implants of freeze-dried chitosan, a clot activator, a lyoprotectant and autologous PRP were injected into surgically created meniscus defects. Implant retention was assessed at 1 day and tissue repair was assessed at 21 days post-surgery.

In another embodiment, a chronic cartilage repair model was developed in the rabbit and used to test the effect of hybrid implants of osteochondral repair. Surgical defects were created on the trochlea of NZW rabbits and allowed to progress to chronic stage. The cartilage defects were treated with hybrid implants composed of freeze-dried chitosan, a clot activator, a lyoprotectant and autologous PRP. Healing was assessed at 21 days post-surgery.

Example 1

1—Preparation of Chitosan Formulations

Formulations without lyoprotectants or buffer: Chitosan weight average molecular weight $M_w$ 500 kDa, measured by GPC as described in [Nguyen, S., F. M. Winnik, and M. D. Buschmann, *Improved reproducibility in the determination of the molecular weight of chitosan by analytical size exclusion chromatography*. Carbohydrate Polymers, 2009. 75(3): p. 528-533], and 80.6% DDA was dissolved in HCl overnight at room temperature to obtain a final chitosan concentration of 0.56% or 0.67% (w/v). The solutions were autoclaved for 10 minutes and cooled on ice. Post-autoclave chitosan $M_w$ was between 319-403 kDa. Autoclaved 5M NaCl and filter-sterilised 270 mM $CaCl_2$ were added as required before dispensing in 10 mL individual vials for freeze-drying.

Formulations with lyoprotectants and buffer: Chitosan ($M_w$ 500 kDa, 80.6% DDA) was dissolved in HCl overnight at room temperature to obtain a final chitosan concentration of 0.56% or 0.67% (w/v). Autoclaved 20% (w/v) sucrose or 20% (w/v) trehalose was added, as required. The solutions were autoclaved for 10 minutes and cooled on ice. Post-autoclave chitosan $M_w$ was between 342-421 kDa. Filter-sterilised 270 mM $CaCl_2$ and stock L-histidine 200 mM were added as required before dispensing in 10 mL individual vials for freeze-drying.

As per Tables 1&2, the HCl concentration was adjusted so that all formulations had theoretical target pH 6.6. The histidine buffer concentration was adjusted to match the overall monomer content in the cakes. The lyoprotectant concentrations were adjusted so that all formulations had theoretical osmolality 350 mOsm.

2—Freeze-Drying Cycle

The freeze-drying cycle consisted of: 1) Ramped freezing to −40° C. in 1 hour then isothermal 2 hours at −40° C., 2) −40° C. for 48 hours and 3) Ramped heating to 30° C. in 12 hours then isothermal 6 hours at 30° C., at 300 millitorrs.

TABLE 1

Formulations containing the clot activator (CaCl$_2$) to be reconstituted directly with PRP.

| Formulation | Group | Total volume prepared | Chitosan (w/v) | HCl (mM) | NaCl (mM) | Sucrose (mM) | Trehalose (mM) | Histidine (mM) | CaCl$_2$ (mM) | Aliquot volume for F/D | Rehydration volume |
|---|---|---|---|---|---|---|---|---|---|---|---|
| 1 | Chitosan-NaCl | 5 mL | 0.56% | 12 | 130 | — | — | — | 45 | 1 mL | 1 mL PRP [1] |
| 3 | Chitosan-6.3% Sucrose | 5 mL | 0.56% | 12 | — | 184 | — | — | 45 | 1 mL | 1 mL PRP [2] |
| 4 | Chitosan-7.0% Trehalose | 5 mL | 0.56% | 12 | — | — | 185 | — | 45 | 1 mL | 1 mL PRP [3] |
| 5 | Chitosan-5.2% Sucrose - Histidine | 5 mL | 0.56% | 12 | — | 152 | — | 33 | 45 | 1 mL | 1 mL PRP [4] |
| 6 | Chitosan-5.8% Trehalose - Histidine | 5 mL | 0.56% | 12 | — | — | 153 | 33 | 45 | 1 mL | 1 mL PRP [5] |

[1] Final hybrid: Chitosan (0.56%)-HCl(12 mM)-NaCl(130 mM)-CaCl$_2$(45 mM)-PRP
[2] Final hybrid: Chitosan (0.56%)-HCl(12 mM)- Sucrose (184 mM)-CaCl$_2$(45 mM)-PRP
[3] Final hybrid: Chitosan (0.56%)-HCl(12 mM)-Trehalose (185 mM)-CaCl$_2$(45 mM)- PRP
[4] Final hybrid: Chitosan (0.56%)-HCl(12 mM)-Sucrose (152 mM)-Histidine (33 mM)-CaCl$_2$(45 mM)-PRP
[5] Final hybrid: Chitosan (0.56%)-HCl(12 mM)- Trehalose (183 mM)-Histidine (33 mM)-CaCl$_2$(45 mM)-PRP

TABLE 2

Formulations to be activated with CaCl$_2$ after reconstitution with PRP.

| Formulation | Group | Total volume prepared | Chitosan (w/v) | HCl (mM) | NaCl (mM) | Sucrose (mM) | Trehalose (mM) | Histidine (mM) | Aliquot volume for F/D | Rehydration volume | 3% CaCl$_2$ volume |
|---|---|---|---|---|---|---|---|---|---|---|---|
| 2 | Chitosan- NaCl | 5 mL | 0.67% | 15 | 201 | — | — | — | 1 mL | 1 mL PRP | 200 µL[1] |
| 7 | Chitosan- 10.0% Sucrose | 5 mL | 0.67% | 15 | — | 293 | — | — | 1 mL | 1 mL PRP | 200 µL[2] |
| 8 | Chitosan- 11.2% Trehalose | 5 mL | 0.67% | 15 | — | — | 296 | — | 1 mL | 1 mL PRP | 200 µL[3] |
| 9 | Chitosan- 8.6% Sucrose - Histidine | 5 mL | 0.67% | 15 | — | 250 | — | 39 | 1 mL | 1 mL PRP | 200 µL[4] |
| 10 | Chitosan- 9.5% Trehalose - Histidine | 5 mL | 0.67% | 15 | — | — | 251 | 39 | 1 mL | 1 mL PRP | 200 µL[5] |

[1] Final hybrid: Chitosan (0.56%)-HCl(12 mM)-NaCl(167 mM)-CaCl$_2$(45 mM)-PRP
[2] Final hybrid: Chitosan (0.56%)-HCl(12 mM)- Sucrose (244 mM)-CaCl$_2$(45 mM)-PRP
[3] Final hybrid: Chitosan (0.56%)-HCl(12 mM)-Trehalose (247 mM)-CaCl$_2$(45 mM)- PRP
[4] Final hybrid: Chitosan (0.56%)-HCl(12 mM)-Sucrose (208 mM)-Histidine (39 mM)-CaCl$_2$(45 mM)-PRP
[5] Final hybrid: Chitosan (0.56%)-HCl(12 mM)- Trehalose (209 mM)-Histidine (39 mM)-CaCl$_2$(45 mM)-PRP

3—Cake Appearance

Cake appearance was scored on a scale of − (shrunken, sheet-like or cracked) to 3+(homogenous solid bulky form). Cakes that scored 2+ or 3+ were deemed acceptable.

Formulations containing NaCl had uneven surfaces and formulation #1 shrunk significantly during freeze-drying. Formulations containing histidine buffer (33 to 39 mM) had cracked and uneven surfaces.

Formulations containing sucrose or trehalose with and without CaCl$_2$ had a smooth even white surface and were slightly depressed at the top. The presence of a lyoprotectant aids in obtaining mechanically stable cakes.

4—Isolation of Rabbit PRP

Whole blood was extracted from NZW rabbits and mixed with acid citrate dextrose (ACD) anti-coagulant (8.5 mL blood to 1.5 mL ACD).

The blood was centrifuged in an ACE E-Z PRP™ centrifuge at 160 g for 10 minutes at room temperature.

The supernatant fractions containing plasma and the buffy coat as well as the first 1-2 mm of the erythrocyte layer was removed using a 2½ inch (18-gauge) blunt needle attached to a 10 mL syringe.

The plasma and buffy coat were further centrifuged at 400 g for 10 minutes at room temperature in order to separate platelet-rich plasma (PRP) from platelet poor plasma (PPP).

5—Cake Reconstitution

Cakes were reconstituted with 1 mL PRP only (Formulations #3 to 6) or with 1 mL PRP and then activated with 200 µL 3% (w/v) CaCl$_2$ (Formulations #2, 7 and 8).

Two different mixing methods were tested: Swirling the vial for 10 seconds and aspirating-ejecting twice with a syringe equipped with a needle or mixing with three 0.39 g steel beads for 10 seconds.

Undissolved chitosan particles were observed post-reconstitution with both mixing methods tested (FIGS. 1A1 and 1A2).

6—Liquid Expression

Formulations reconstituted in PRP were dispensed into glass tubes at 37° C. After 60 minutes, liquid expression and volume loss from the hybrid clots was quantified by weight measurement.

All tested formulations clotted. The clot activator can be added directly to the freeze-dried cake.

All hybrid clots expressed less liquid than PRP alone (FIG. 1B1).

7—Clot Homogeneity

Hybrid clots were fixed in 10% NBF and paraffin sections stained with Safranin O/Fast Green to evaluate chitosan dispersion in the clots.

Chitosan aggregates were not dispersed throughout the hybrid clots for any of the formulations (FIGS. 1A3 and 1A4).

8—In Vivo Cartilage Repair Model

Two formulations (#3 and #4) were tested in vivo in a rabbit cartilage repair model.

Chondral defects of 3.5 mm×4.5 mm were created bi-laterally in the trochlea of two 19-month old NZW rabbits. Four microdrill holes were pierced through the subchondral bone with a 0.9 mm drill bit to a depth of ~4 mm.

Autologous PRP was prepared from rabbit blood extracted immediately prior to surgery, as described above in section 4-Isolation of rabbit PRP. After creation of the defect, the freeze-dried chitosan cake was reconstituted with 1 mL PRP using the bead mixing method and the implant (1 hanging drop) was delivered over the defect site and allowed to solidify in situ for ~5 min before closing the knee.

On the contralateral knee, the freeze-dried chitosan was mixed with 1 mL fresh blood collected immediately prior to reconstitution and delivery.

At 10 days post-surgery, freeze-dried chitosan/PRP hybrid implants were observed at the surface of the microdrill holes, along with inflammatory infiltrate (FIG. 1B2). Hybrid implants were cleared by 21 days post-surgery.

TABLE 3

Performance of the 10 different formulations.

| Criteria number | Criteria description | Performance of formulations |
|---|---|---|
| 1 | Homogenous solid form with good mechanical properties for shipping (Assessed with cake appearance) | Four met criteria 1 (#3-6) |
| 2 | Rapid and complete reconstitution (Assessed with visual inspection post-mixing) | None met criteria 2 |
| 3 | The mixture should not inhibit coagulation (Assessed with thromboelastography) | Not checked |
| 4 | The coagulated mixtures (implants) should be mechanically stable (Assessed with manual crushing test) | Not checked |
| 5 | The coagulated mixtures (implants) should largely inhibit clot retraction (Assessed with liquid expression measurements) | Five met criteria 5 (#2, 3, 4, 5, 6) |
| 6 | Good mixing without phase separation of the polymer and blood components (Assessed with histology) | None met criteria 6 |
| 7 | The mixtures should have appropriate handling properties (Assessed with runniness test) | Not checked |
| 8 | The mixtures should have close to physiological properties (Assessed with pH and osmolality measurements) | Not checked |

In Example 1, lyoprotectants are required to obtain cakes that are mechanically stable for storage and shipping, but that adding buffer to the cakes induces surface cracking. The clot activator may be added directly to the freeze-dried cakes to induce coagulation of the chitosan/PRP mixtures in situ. Freeze-dried cakes prepared with high molecular weight chitosan however did not dissolve easily and completely in PRP. Freeze-dried chitosan/PRP hybrids did not induce chronic inflammation upon implantation in an acute rabbit chondral defect model and were cleared by 21 days in vivo.

Example 2

1—Preparation of Chitosan Formulations

Chitosan number average molecular weight $M_n$ 211 kDa, measured by GPC as described in [Nguyen, S., F. M. Winnik, and M. D. Buschmann, *Improved reproducibility in the determination of the molecular weight of chitosan by analytical size exclusion chromatography*. Carbohydrate Polymers, 2009. 75 (3): p. 528-533] and 80.6% DDA was dissolved in HCl overnight at room temperature to obtain a final chitosan concentration of 0.56% or 0.42% (w/v). The solutions were autoclaved for 10 minutes and cooled on ice. Post-autoclave chitosan $M_n$ was between 112-160 kDa. Autoclaved 20% (w/v) sucrose, 20% (w/v) trehalose and 5M NaCl as well as filter-sterilised 270 mM $CaCl_2$ and were added, as required. A filter-sterilised Rhodamine-chitosan tracer ($M_n$ 143 kDa, 80.0% DDA) was added before dispensing in 10 mL individual vials for freeze-drying.

As per Table 4, the HCl concentration was adjusted so that all formulations had theoretical target pH 6.45. The NaCl concentration was adjusted so that all formulations had theoretical osmolality 350 mOsm. Lyoprotectant concentration was adjusted to be between 1 and 10% (w/v).

2—Freeze-Drying Cycle

The freeze-drying cycle consisted of: 1) Ramped freezing to −40° C. in 1 hour then isothermal 2 hours at −40° C., 2) −40° C. for 48 hours and 3) Ramped heating to 30° C. in 12 hours then isothermal 6 hours at 30° C., at 100 millitorrs.

TABLE 4

Formulations containing the clot activator (CaCl$_2$) to be reconstituted directly with PRP.

| Formulation | Group | Total volume prepared | Volume of tracer added | Chitosan (w/v) | HCl (mM) | NaCl (mM) | Sucrose (mM) | Trehalose (mM) | CaCl$_2$ (mM) | Aliquot volume for F/D | Rehydration volume |
|---|---|---|---|---|---|---|---|---|---|---|---|
| 1 | Chitosan only | 10 mL | 0.1 mL | 0.56% | 14 mM | — | — | — | 42.2 mM | 1 mL | 1 mL PRP |
| 2 | Chitosan-NaCl | 10 mL | 0.1 mL | 0.56% | 14 mM | 130 mM | — | — | 42.2 mM | 1 mL | 1 mL PRP |
| 3 | Chitosan 1% Sucrose | 10 mL | 0.1 mL | 0.56% | 14 mM | — | 29 mM | — | 42.2 mM | 1 mL | 1 mL PRP |
| 4 | Chitosan 2% Sucrose | 10 mL | 0.1 mL | 0.56% | 14 mM | — | 58 mM | — | 42.2 mM | 1 mL | 1 mL PRP |
| 5 | Chitosan 4% Sucrose | 10 mL | 0.1 mL | 0.56% | 14 mM | — | 117 mM | — | 42.2 mM | 1 mL | 1 mL PRP |
| 6 | Chitosan 6% Sucrose | 10 mL | 0.1 mL | 0.56% | 14 mM | — | 175 mM | — | 42.2 mM | 1 mL | 1 mL PRP |
| 7 | Chitosan 8% Sucrose | 10 mL | 0.1 mL | 0.56% | 14 mM | — | 234 mM | — | 42.2 mM | 1 mL | 1 mL PRP |
| 8 | Chitosan 10% Sucrose | 10 mL | 0.1 mL | 0.56% | 14 mM | — | 292 mM | — | 42.2 mM | 1 mL | 1 mL PRP |
| 9 | Chitosan 1% Trehalose | 10 mL | 0.1 mL | 0.56% | 14 mM | — | — | 24 mM | 42.2 mM | 1 mL | 1 mL PRP |
| 10 | Chitosan 2% Trehalose | 10 mL | 0.1 mL | 0.56% | 14 mM | — | — | 48 mM | 42.2 mM | 1 mL | 1 mL PRP |
| 11 | Chitosan 4% Trehalose | 10 mL | 0.1 mL | 0.56% | 14 mM | — | — | 96 mM | 42.2 mM | 1 mL | 1 mL PRP |
| 12 | Chitosan 6% Trehalose | 10 mL | 0.1 mL | 0.56% | 14 mM | — | — | 144 mM | 42.2 mM | 1 mL | 1 mL PRP |
| 13 | Chitosan 8% Trehalose | 10 mL | 0.1 mL | 0.56% | 14 mM | — | — | 191 mM | 42.2 mM | 1 mL | 1 mL PRP |
| 14 | Chitosan 10% Trehalose | 10 mL | 0.1 mL | 0.56% | 14 mM | — | — | 239 mM | 42.2 mM | 1 mL | 1 mL PRP |
| 15 | Chitosan only | 10 mL | 0.1 mL | 0.42% | 10 mM | — | — | — | 42.2 mM | 1 mL | 1 mL PRP |
| 16 | Chitosan-NaCl | 10 mL | 0.1 mL | 0.42% | 10 mM | 133 mM | — | — | 42.2 mM | 1 mL | 1 mL PRP |
| 17 | Chitosan 1% Sucrose | 10 mL | 0.1 mL | 0.42% | 10 mM | — | 29 mM | — | 42.2 mM | 1 mL | 1 mL PRP |
| 18 | Chitosan 2% Sucrose | 10 mL | 0.1 mL | 0.42% | 10 mM | — | 58 mM | — | 42.2 mM | 1 mL | 1 mL PRP |
| 19 | Chitosan 4% Sucrose | 10 mL | 0.1 mL | 0.42% | 10 mM | — | 117 mM | — | 42.2 mM | 1 mL | 1 mL PRP |
| 20 | Chitosan 6% Sucrose | 10 mL | 0.1 mL | 0.42% | 10 mM | — | 175 mM | — | 42.2 mM | 1 mL | 1 mL PRP |
| 21 | Chitosan 8% Sucrose | 10 mL | 0.1 mL | 0.42% | 10 mM | — | 234 mM | — | 42.2 mM | 1 mL | 1 mL PRP |
| 22 | Chitosan 10% Sucrose | 10 mL | 0.1 mL | 0.42% | 10 mM | — | 292 mM | — | 42.2 mM | 1 mL | 1 mL PRP |
| 23 | Chitosan 1% Trehalose | 10 mL | 0.1 mL | 0.42% | 10 mM | — | — | 24 mM | 42.2 mM | 1 mL | 1 mL PRP |
| 24 | Chitosan 2% Trehalose | 10 mL | 0.1 mL | 0.42% | 10 mM | — | — | 48 mM | 42.2 mM | 1 mL | 1 mL PRP |
| 25 | Chitosan 4% Trehalose | 10 mL | 0.1 mL | 0.42% | 10 mM | — | — | 96 mM | 42.2 mM | 1 mL | 1 mL PRP |
| 26 | Chitosan 6% Trehalose | 10 mL | 0.1 mL | 0.42% | 10 mM | — | — | 144 mM | 42.2 mM | 1 mL | 1 mL PRP |
| 27 | Chitosan 8% Trehalose | 10 mL | 0.1 mL | 0.42% | 10 mM | — | — | 191 mM | 42.2 mM | 1 mL | 1 mL PRP |
| 28 | Chitosan 10% Trehalose | 10 mL | 0.1 mL | 0.42% | 10 mM | — | — | 239 mM | 42.2 mM | 1 mL | 1 mL PRP |

3—Cake Appearance

Formulations containing chitosan-only were sheet-like (FIG. 2A1). Formulations containing NaCl only shrunk significantly during freeze-drying.

Formulations containing 2% (w/v) or more of sucrose or trehalose were bulkier, confirming that lyoprotectants are required to obtain mechanically stable clots. Cakes were bulkiest when increasing lyoprotectant concentrations were used (FIG. 2A2).

4—Isolation of Sheep PRP

Whole blood was extracted from Arcott cross sheep and mixed with acid citrate dextrose (ACD) anti-coagulant (8.5 mL blood to 1.5 mL ACD).

The blood was centrifuged in an ACE E-Z PRP™ centrifuge at 160 g for 10 minutes at room temperature.

The supernatant fractions containing plasma and the buffy coat as well as the first 1-2 mm of the erythrocyte layer was removed using a 2½ inch (18-gauge) blunt needle attached to a 10 mL syringe.

The plasma and buffy coat were further centrifuged at 400 g for 10 minutes at room temperature in order to separate platelet-rich plasma (PRP) from platelet poor plasma (PPP).

5—Cake Reconstitution

Cakes were reconstituted with 1 mL PRP and mixed with three 0.39 g steel beads for 10 seconds. Two different sheep donors were used to test each cake.

Undissolved chitosan particles were observed post-reconstitution.

6—Thromboelastography (TEG)

360 µL of each formulation was loaded into a TEG cup immediately after mixing and TEG tracings were recorded for 1 hour.

Formulations containing chitosan only did not clot reproducibly.

Clotting was inhibited for the formulations containing NaCl only.

Formulations containing 2% (w/v) sucrose or trehalose coagulated normally and had clot reaction time (R) ranging between 9-18 minutes and maximal amplitude (MA) between 55 and 75 mm (FIG. 2B1).

Clotting was inhibited in 3 cases out of 8 for formulations containing 8% (w/v) sucrose or trehalose. For the other 5 cases, decreased maximal amplitude (MA) between 14 and 20 mm was observed (FIG. 2B2).

Clotting was inhibited in 5 cases out of 8 for formulations containing 10% (w/v) sucrose or trehalose (FIG. 2B3). For the other 3 cases, decreased maximal amplitude (MA) between 9 and 24 mm was observed.

6—Liquid Expression

Formulations reconstituted in PRP were dispensed into glass tubes at 37° C. After 60 minutes, liquid expression and volume loss from the hybrid clots was quantified by weight measurement.

All hybrid clots tested expressed less liquid than PRP alone.

7—Clot Homogeneity

Hybrid clots were fixed in 10% NBF and thick razor blade sections were observed with epifluorescence microscopy to evaluate chitosan dispersion in the clots.

Chitosan aggregates were not dispersed throughout the hybrid clots containing sucrose or trehalose (FIGS. 2A3 & 2A4). Dispersion was better in the formulations devoid of lyoprotectants.

TABLE 5

Performance of the 28 different formulations.

| Criteria number | Criteria description | Performance of formulations |
|---|---|---|
| 1 | Homogenous solid form with good mechanical properties for shipping (Assessed with cake appearance) | Sixteen met criteria 1 (#5-8, 11-14, 19-22, 25-28) |
| 2 | Rapid and complete reconstitution (Assessed with visual inspection post-mixing) | None met criteria 2 |
| 3 | The mixture should not inhibit coagulation (Assessed with thromboelastography) | Four met criteria 3 (#4, 10, 18, 24) |
| 4 | The coagulated mixtures (implants) should be mechanically stable (Assessed with manual crushing test) | Not checked |
| 5 | The coagulated mixtures (implants) should largely inhibit clot retraction (Assessed with liquid expression measurements) | Sixteen met criteria 5 (#1, 2, 4, 7, 8, 10, 13, 14, 15, 16, 18, 21, 22, 24, 27, 28) |
| 6 | Good mixing without phase separation of the polymer and blood components (Assessed with histology) | Four met criteria 6 (#1, 2, 15, 16) |
| 7 | The mixtures should have appropriate handling properties (Assessed with runniness test) | Not checked |
| 8 | The mixtures should have close to physiological properties (Assessed with pH and osmolality measurements) | Not checked |

In Example 2, increasing lyoprotectant concentrations improves mechanical stability of cakes but also inhibits coagulation of chitosan/PRP mixtures. Freeze-dried cakes containing high molecular weight chitosan do not dissolve easily and completely in PRP.

Example 3

1—Preparation of Chitosan Formulations

Chitosan ($M_n$ 211 kDa, 80.6% DDA) was dissolved in HCl overnight at room temperature to obtain a final chitosan concentration of 0.56% (w/v). The solutions were autoclaved for 10 minutes and cooled on ice. Post-autoclave chitosan $M_n$ was 151 and 162 kDa. Autoclaved 20% (w/v) trehalose and 5M NaCl, as well as filter-sterilised 270 mM $CaCl_2$ and were added, as required. Filter-sterilised Rhodamine-chitosan tracer ($M_n$ 143 kDa, 80.0% DDA) was added before dispensing in 10 mL individual vials for freeze-drying.

As per Table 6, the HCl concentration was adjusted so that all formulations had theoretical target pH 6.45. The NaCl concentration was adjusted so that the formulation had theoretical osmolality 350 mOsm. Lyoprotectant concentration was set at 2% (w/v) for formulation #2.

The freeze-drying cycle was identical to the one described in Example 2, Section 2-Freeze-drying cycle.

TABLE 6

Freeze-dried formulations containing the clot activator (CaCl₂) to be reconstituted directly with PRP.

| Formulation | Group | Total volume prepared | Volume of tracer added | Chitosan (w/v) | HCl (mM) | NaCl (mM) | Trehalose (mM) | CaCl₂ (mM) | Aliquot volume for F/D | Rehydration volume |
|---|---|---|---|---|---|---|---|---|---|---|
| 1[1] | Chitosan-NaCl | 10 mL | 0.1 mL | 0.56% | 14 mM | 130 mM | — | 42.2 mM | 1 mL | 1 mL PRP |
| 2[2] | Chitosan 2% Trehalose | 10 mL | 0.1 mL | 0.56% | 14 mM | — | 48 mM | 42.2 mM | 1 mL | 1 mL PRP |

[1]Final hybrid: Chitosan (0.56%)-HCl(14 mM)-NaCl(130 mM)-CaCl₂(42.2 mM)-PRP
[2]Final hybrid: Chitosan (0.56%)-HCl(14 mM)- Trehalose (48 mM)-CaCl₂(42.2 mM)-PRP 2—Isolation of Human PRP Whole blood was extracted from a human donor and mixed with 3.8% (w/v) tri sodium citrate dihydrate solution (9 mL blood to 1 mL sodium citrate).

The blood was centrifuged in an ACE E-Z PRP™ centrifuge at 160 g for 10 minutes at room temperature.

The supernatant fractions containing plasma and the buffy coat as well as the first 1-2 mm of the erythrocyte layer was removed using a 2⅞ inch (18-gauge) blunt needle attached to a 10 mL syringe.

The plasma and buffy coat were further centrifuged at 400 g for 10 minutes at room temperature in order to separate platelet-rich plasma (PRP) from platelet poor plasma (PPP).

3—Cake Appearance

The formulation containing NaCl only shrunk significantly during freeze-drying.

The formulation containing 2% (w/v) trehalose was mechanically stable and met performance criteria 1.

4—Cake Reconstitution

Cakes were reconstituted with 1 mL PRP and mixed with three 0.39 g steel beads for 10 seconds.

Undissolved chitosan particles were observed post-reconstitution.

5—Preparation and Mixing of Liquid Formulations

Liquid chitosan formulations were also prepared to test in parallel with the freeze-dried formulations (Table 7). The solutions were autoclaved for 10 minutes and cooled on ice. Post autoclave chitosan $M_n$ was 145 and 163 kDa.

400 μL of liquid chitosan formulation was mixed with 800 μL PRP and activated using 240 μL of 3% (w/v) CaCl₂.

6—Clot Homogeneity

Reconstituted freeze-dried formulations and liquid formulations were dispensed into glass tubes at 37° C. and left to clot for 1 hour.

Hybrid clots were fixed in 10% NBF and thick razor blade sections were observed with epifluorescence microscopy to evaluate chitosan dispersion in the clots.

Chitosan aggregates were not dispersed throughout the freeze-dried hybrid clots (FIGS. 3A1 & 3A2).

Chitosan was well dispersed within the hybrid clots prepared with liquid solutions (FIGS. 3A3 & 3A4).

7—Ex Vivo Implantation in Meniscal Defects

A straight razor blade was used to take ~0.5 mm cross-sections from pig meniscus and a horizontal flap was created towards the femoral (top) surface of the meniscus.

A 4 mm biopsy punch was used to create a partial thickness defect towards the tibial (bottom) surface of the meniscus.

The menisci were wrapped in humid plastic film and were placed at 37° C. for at least 30 min before the start of the experiment.

Reconstituted freeze-dried formulations and liquid formulations were injected into the partial-thickness meniscus defects using a syringe fitted with a 20-gauge needle and the flap was closed immediately.

The menisci were immediately re-wrapped and sealed with humid plastic film and were placed at 37° C. for 1 hour.

Freeze-dried chitosan/PRP and liquid formulations were successfully implanted ex vivo in meniscal defects where they coagulated in situ.

Pig menisci were fixed in 10% NBF and thick razor blade sections were observed with epifluorescence microscopy to evaluate chitosan dispersion in the clots.

TABLE 7

Liquid formulations to be mixed with PRP and activated with the clot activator (CaCl₂).

| Sol Group | Total volume prepared | Volume of tracer added | Chito-san (w/v) | HCl (mM) | NaCl (mM) | Trehalose (mM) |
|---|---|---|---|---|---|---|
| 3[1] Chitosan-NaCl | 10 mL | 0.1 mL | 2% | 50 mM | 150 mM | — |
| 4[2] Chitosan 2% Trehalose | 10 mL | 0.1 mL | 2% | 50 mM | — | 171 mM |

[1]Final hybrid: Chitosan (0.56%)-HCl(14 mM)-NaCl(42 mM)-CaCl₂(45 mM)-PRP
[2]Final hybrid: Chitosan (0.56%)-HCl(14 mM)- Trehalose (48 mM)-CaCl₂(45 mM)-PRP Chitosan was aggregated and not dispersed throughout the meniscal defects for the freeze-dried formulations (FIGS. 3B1 & 3B2).

Chitosan was well dispersed within the meniscal defects for the liquid formulations (FIGS. 3B3 & 3B4).

TABLE 8

Performance of the 2 different freeze-dried formulations.

| Criteria number | Criteria description | Performance of formulations |
|---|---|---|
| 1 | Homogenous solid form with good mechanical properties for shipping (Assessed with cake appearance) | One met criteria 1 (#2) |
| 2 | Rapid and complete reconstitution (Assessed with visual inspection post-mixing) | None met criteria 2 |
| 3 | The mixture should not inhibit coagulation (Assessed with thromboelastography) | Not checked |
| 4 | The coagulated mixtures (implants) should be mechanically stable (Assessed with manual crushing test) | Not checked |
| 5 | The coagulated mixtures (implants) should largely inhibit clot retraction (Assessed with liquid expression measurements) | All met criteria 5 (#1, 2) |
| 6 | Good mixing without phase separation of the polymer and blood components (Assessed with histology) | None met criteria 6 |
| 7 | The mixtures should have appropriate handling properties (Assessed with runniness test) | Not checked |
| 8 | The mixtures should have close to physiological properties (Assessed with pH and osmolality measurements) | Not checked |

In Example 3, although liquid formulations of chitosan can be easily mixed with PRP, reconstitution of freeze-dried chitosan formulations in PRP is much more challenging. Freeze-dried cakes containing high molecular weight chitosan did not dissolve easily and completely in PRP but could still be implanted ex vivo in a meniscal defect model using a standard operating room apparatus.

Example 4

1—Preparation of Chitosan Formulations

Formulations with Chitosan $M_n$>100 kDa: Chitosans ($M_n$ 211 kDa, 80.6% DDA and $M_n$ 105 kDa, 81.2% DDA) were dissolved in HCl overnight at room temperature to obtain a final chitosan concentration of 0.56% (w/v). The solutions were autoclaved for 10 minutes and cooled on ice. Filter-sterilised 15% (w/v) trehalose, 15% (w/v) mannitol, 270 mM $CaCl_2$, stock L-histidine buffer 55 mM pH 6.5 (prepared by mixing 10 mL of 0.017% w/v L-histidine and 10 mL of HCl 30 mM) and autoclaved 5M NaCl were added, as required. Filter-sterilised Rhodamine-chitosan tracer ($M_n$ 110 kDa, 80.2% DDA) was added before dispensing in 3 mL individual vials for freeze-drying.

Formulations with Chitosan $M_n$<100 kDa: Chitosans ($M_n$ 38 kDa, 82.5% DDA, $M_n$ 11 kDa, 84.4% DDA and $M_n$ 4 kDa, 80.2% DDA) were dissolved in HCl overnight at room temperature to obtain a final chitosan concentration of 0.56% (w/v). The solutions were filter-sterilised. Filter-sterilised 15% (w/v) trehalose, 15% (w/v) mannitol, 270 mM $CaCl_2$, 5M NaCl and stock histidine buffer 55 mM pH 6.5 (prepared by mixing 10 mL of 0.017% w/v L-histidine and 10 mL of HCl 30 mM) were added, as required. Filter-sterilised Rhodamine-chitosan tracer ($M_n$ 40 kDa, 80.0% DDA or $M_n$ 10 kDa, 81.9% DDA) was added before dispensing in 3 mL individual vials for freeze-drying.

As per Table 9, the HCl concentration was adjusted so that all formulations had a HCl:glucosamine ratio of 0.6. The NaCl concentration was adjusted so that the formulation had theoretical osmolality 350 mOsm. A lower concentration of histidine (3.8 mM vs 33-39 mM in previous examples) was chosen to prevent cake cracking. Lyoprotectant concentration was set at 2% or 6% (w/v) enough to provide a stable cake but not impede coagulation.

The freeze-drying cycle was identical to the one described in Example 2, Section 2-Freeze-drying cycle.

TABLE 9

Freeze-dried formulations containing the clot activator ($CaCl_2$) to be reconstituted directly with PRP.

| Formulation | Group | Chitosan (w/v) | HCl (mM) | NaCl (mM) | Trehalose (mM) | Mannitol (mM) | Histidine (mM) | $CaCl_2$ (mM) | $M_n$ (kDa) | Type of chitosan |
|---|---|---|---|---|---|---|---|---|---|---|
| 1 | CS-NaCl | 0.56% | 16 | 150 | 0 | 0 | 0 | 42.2 | 126 | High $M_n$ Chitosan |
| 2 | CS-NaCl-Hist | 0.56% | 16 | 150 | 0 | 0 | 3.8 | 42.2 | 130 | |
| 3 | CS-2% Trehalose | 0.56% | 16 | 0 | 53 | 0 | 0 | 42.2 | 131 | |
| 4 | CS-2% Trehalose-Hist | 0.56% | 16 | 0 | 53 | 0 | 3.8 | 42.2 | 129 | |
| 5 | CS-6% Trehalose | 0.56% | 16 | 0 | 159 | 0 | 0 | 42.2 | N/D | |
| 6 | CS-6% Trehalose-Hist | 0.56% | 16 | 0 | 159 | 0 | 3.8 | 42.2 | 183 | |
| 7 | CS-2% Mannitol | 0.56% | 16 | 0 | 0 | 110 | 0 | 42.2 | 150 | |
| 8 | CS-2% Mannitol-Hist | 0.56% | 16 | 0 | 0 | 110 | 3.8 | 42.2 | 148 | |
| 9 | CS-6% Mannitol | 0.56% | 16 | 0 | 0 | 329 | 0 | 42.2 | 154 | |
| 10 | CS-6% Mannitol-Hist | 0.56% | 16 | 0 | 0 | 329 | 3.8 | 42.2 | 167 | |
| 11 | CS-NaCl | 0.56% | 16.4 | 150 | 0 | 0 | 0 | 42.2 | 38 | Medium $M_n$ Chitosan |
| 12 | CS-NaCl-Hist | 0.56% | 16.4 | 150 | 0 | 0 | 3.8 | 42.2 | 38 | |
| 13 | CS-2% Trehalose | 0.56% | 16.4 | 0 | 53 | 0 | 0 | 42.2 | 38 | |
| 14 | CS-2% Trehalose-Hist | 0.56% | 16.4 | 0 | 53 | 0 | 3.8 | 42.2 | 38 | |
| 15 | CS-6% Trehalose | 0.56% | 16.1 | 0 | 159 | 0 | 0 | 42.2 | 79 | |
| 16 | CS-6% Trehalose-Hist | 0.56% | 16.1 | 0 | 159 | 0 | 3.8 | 42.2 | 102 | |
| 17 | CS-2% Mannitol | 0.56% | 16.4 | 0 | 0 | 110 | 0 | 42.2 | 38 | |

TABLE 9-continued

Freeze-dried formulations containing the clot activator (CaCl$_2$) to be reconstituted directly with PRP.

| Formulation | Group | Chitosan (w/v) | HCl (mM) | NaCl (mM) | Trehalose (mM) | Mannitol (mM) | Histidine (mM) | CaCl$_2$ (mM) | M$_n$ (kDa) | Type of chitosan |
|---|---|---|---|---|---|---|---|---|---|---|
| 18 | CS-2% Mannitol-Hist | 0.56% | 16.4 | 0 | 0 | 110 | 3.8 | 42.2 | 38 | |
| 19 | CS-6% Mannitol | 0.56% | 16.1 | 0 | 0 | 329 | 0 | 42.2 | 88 | |
| 20 | CS-6% Mannitol-Hist | 0.56% | 16.1 | 0 | 0 | 329 | 3.8 | 42.2 | 89 | |
| 21 | CS-NaCl | 0.56% | 17 | 150 | 0 | 0 | 0 | 42.2 | 11 | Low M$_n$ Chitosan |
| 22 | CS-NaCl-Hist | 0.56% | 17 | 150 | 0 | 0 | 3.8 | 42.2 | 11 | |
| 23 | CS-2% Trehalose | 0.56% | 17 | 0 | 53 | 0 | 0 | 42.2 | 11 | |
| 24 | CS-2% Trehalose-Hist | 0.56% | 17 | 0 | 53 | 0 | 3.8 | 42.2 | 11 | |
| 25 | CS-6% Trehalose | 0.56% | 16 | 0 | 159 | 0 | 0 | 42.2 | 4 | |
| 26 | CS-6% Trehalose-Hist | 0.56% | 16 | 0 | 159 | 0 | 3.8 | 42.2 | 4 | |
| 27 | CS-2% Mannitol | 0.56% | 17 | 0 | 0 | 110 | 0 | 42.2 | 11 | |
| 28 | CS-2% Mannitol-Hist | 0.56% | 17 | 0 | 0 | 110 | 3.8 | 42.2 | 11 | |
| 29 | CS-6% Mannitol | 0.56% | 16 | 0 | 0 | 329 | 0 | 42.2 | 4 | |
| 30 | CS-6% Mannitol-Hist | 0.56% | 16 | 0 | 0 | 329 | 3.8 | 42.2 | 4 | |

2—Cake Appearance

Formulations without lyoprotectant shrunk significantly during freeze-drying.

Histidine buffer used at a 3.8 mM concentration did not induced cake cracking as seen previously in Example 1 with higher concentrations of 33-39 mM.

Cakes were bulkiest when increased lyoprotectant concentrations were used. Cakes containing mannitol were bulkier than cakes containing trehalose (FIGS. 4A1 & 4A2).

3—Cake Reconstitution

Human PRP and PPP were extracted as described above in Example 3, Section 2-Isolation of human PRP.

Cakes were reconstituted with 1 mL PRP or 1 mL PPP and mixed with three 0.39 g steel beads for 10 seconds.

Medium and low M$_n$ chitosans dissolved better than higher M$_n$ chitosans, especially in the presence of lyoprotectants.

4—Liquid Expression

Formulations reconstituted in PRP were dispensed into glass tubes at 37° C. After 60 minutes, liquid expression from the hybrid clots was quantified by weight measurement.

All hybrid clots expressed less liquid than PRP alone.

5—Clot Homogeneity

Hybrid clots were fixed in 10% NBF and thick razor blade sections were observed with epifluorescence microscopy to evaluate chitosan dispersion in the clots.

Chitosan aggregated in most hybrid clots prepared with high M$_n$ chitosan (FIGS. 4B1 & 4B2).

Chitosan was well dispersed within most hybrid clots when medium M$_n$ chitosan was used (FIGS. 4B3 & 4B4).

Erythrocytes present in the PRP sedimented towards the bottom of the clots leaving a band of chitosan at the surface of the clot when the lowest M$_n$ chitosans were used (FIGS. 4B5 & 4B6).

6—Ex Vivo Implantation in Meniscal Defects

Freeze-dried chitosan/PRP formulations were successfully implanted ex vivo in meniscal defects where they coagulated in situ as described in Example 3, Section 7-Ex vivo implantation in meniscal defects.

TABLE 10

Performance of the 30 different formulations.

| Criteria number | Criteria description | Performance of formulations |
|---|---|---|
| 1 | Homogenous solid form with good mechanical properties for shipping (Assessed with cake appearance) | Sixteen met criteria 1 (#5-10, 15-20, 27-30) |
| 2 | Rapid and complete reconstitution (Assessed with visual inspection post-mixing) | Eighteen met criteria 2 (#9-10, 13-20, 23-30) |
| 3 | The mixture should not inhibit coagulation (Assessed with thromboelastography) | Not checked |
| 4 | The coagulated mixtures (implants) should be mechanically stable (Assessed with manual crushing test) | Not checked |
| 5 | The coagulated mixtures (implants) should largely inhibit clot retraction (Assessed with liquid expression measurements) | Twenty-two met criteria 5 (#1-10, 13-20, 23, 25, 27, 29) |
| 6 | Good mixing without phase separation of the polymer and blood components (Assessed with histology) | Six met criteria 6 (#13-18) |
| 7 | The mixtures should have appropriate handling properties (Assessed with runniness test) | Not checked |
| 8 | The mixtures should have close to physiological properties (pH 6.6-7.0 and osmolality 400-600 mOsm) (Assessed with pH and osmolality measurements) | Ten met criteria 8 (#3-4, 7-8, 13-14, 17-18, 23, 27) |

In Example 4, decreasing chitosan molecular weight improves cake solubility in PRP, but that only chitosan of medium molecular weight (M$_n$ 38 kDa) produced chitosan/PRP hybrid clots that were homogenous without any phase separation that occurs at lower molecular weight or aggregation that occurs at higher molecular weight.

Example 5

1—Preparation of Chitosan Formulations

Medium $M_n$ Chitosans ($M_n$ 56 kDa, 80.1% DDA and $M_n$ 32 kDa, 81.2% DDA) were dissolved in HCl overnight at room temperature to obtain a final chitosan concentration of 0.56%, 1% or 2% (w/v). The solutions were filter-sterilised. Filter-sterilised 15% (w/v) trehalose, 15% (w/v) mannitol and 270 mM $CaCl_2$ were added, as required. Filter-sterilised Rhodamine-chitosan tracer ($M_n$ 40 kDa, 80.0% DDA) was added before dispensing in 3 mL individual vials for freeze-drying.

As per Table 11, the HCl concentration was adjusted so that all formulations had a HCl:glucosamine ratio of 0.6. Lyoprotectant concentration was set at 2% or 6% (w/v) enough to provide a stable cake but not impede coagulation.

The freeze-drying cycle was identical to the one described in Example 2, Section 2-Freeze-drying cycle.

4—Thromboelastography (TEG)

360 μL of each formulation was loaded into a TEG cup immediately after mixing and TEG tracings were recorded for 1 hour.

Formulations containing 0.56% (w/v) chitosan $M_n$ 32 kDa clotted in 1-phase manner similar to PRP only controls (FIG. 5B1).

Increasing chitosan $M_n$ or concentration induced a 2-phase coagulation mechanism as revealed by TEG tracings (FIGS. 5B2 & 5B3).

In all cases, adding 6% (w/v) lyoprotectant gave softer clots with lower maximal amplitude (MA between 24-61 mm) than adding 2% (w/v) lyoprotectant (MA between 51-84 mm).

5—Runniness Test

Runniness was assessed by placing a 30 μL drop of each formulation onto a rigid piece of plastic fixed at a certain

TABLE 11

Freeze-dried formulations containing the clot activator ($CaCl_2$) to be reconstituted directly with PRP.

| CS | Formulation | Group | Chitosan (w/v) | HCl (mM) | Trehalose (mM) | Mannitol (mM) | $CaCl_2$ (mM) | Aliquot into | Rehydrated in |
|---|---|---|---|---|---|---|---|---|---|
| Chitosan 81.2% DDA $M_n$ 32 kDa | 1 | 0.56% CS-2% Trehalose | 0.56% | 16 mM | 53 mM | — | 42.2 mM | 1 mL | 1 mL PRP |
| | 2 | 0.56% CS-6% Trehalose | 0.56% | 16 mM | 159 mM | — | 42.2 mM | 1 mL | 1 mL PRP |
| | 3 | 0.56% CS-2% Mannitol | 0.56% | 16 mM | — | 110 mM | 42.2 mM | 1 mL | 1 mL PRP |
| | 4 | 0.56% CS-6% Mannitol | 0.56% | 16 mM | — | 329 mM | 42.2 mM | 1 mL | 1 mL PRP |
| | 5 | 1% CS-2% Trehalose | 1% | 29 mM | 53 mM | — | 42.2 mM | 1 mL | 1 mL PRP |
| | 6 | 1% CS-6% Trehalose | 1% | 29 mM | 159 mM | — | 42.2 mM | 1 mL | 1 mL PRP |
| | 7 | 1% CS-2% Mannitol | 1% | 29 mM | — | 110 mM | 42.2 mM | 1 mL | 1 mL PRP |
| | 8 | 1% CS-6% Mannitol | 1% | 29 mM | — | 329 mM | 42.2 mM | 1 mL | 1 mL PRP |
| | 9 | 2% CS-2% Trehalose | 2% | 57 mM | 53 mM | — | 42.2 mM | 1 mL | 1 mL PRP |
| | 10 | 2% CS-6% Trehalose | 2% | 57 mM | 159 mM | — | 42.2 mM | 1 mL | 1 mL PRP |
| | 11 | 2% CS-2% Mannitol | 2% | 57 mM | — | 110 mM | 42.2 mM | 1 mL | 1 mL PRP |
| | 12 | 2% CS-6% Mannitol | 2% | 57 mM | — | 329 mM | 42.2 mM | 1 mL | 1 mL PRP |
| Chitosan 80.1% DDA $M_n$ 56 kDa | 13 | 0.56% CS-2% Trehalose | 0.56% | 16 mM | 53 mM | — | 42.2 mM | 1 mL | 1 mL PRP |
| | 14 | 0.56% CS-6% Trehalose | 0.56% | 16 mM | 159 mM | — | 42.2 mM | 1 mL | 1 mL PRP |
| | 15 | 0.56% CS-2% Mannitol | 0.56% | 16 mM | — | 110 mM | 42.2 mM | 1 mL | 1 mL PRP |
| | 16 | 0.56% CS-6% Mannitol | 0.56% | 16 mM | — | 329 mM | 42.2 mM | 1 mL | 1 mL PRP |
| | 17 | 1% CS-2% Trehalose | 1% | 29 mM | 53 mM | — | 42.2 mM | 1 mL | 1 mL PRP |
| | 18 | 1% CS-6% Trehalose | 1% | 29 mM | 159 mM | — | 42.2 mM | 1 mL | 1 mL PRP |
| | 19 | 1% CS-2% Mannitol | 1% | 29 mM | — | 110 mM | 42.2 mM | 1 mL | 1 mL PRP |
| | 20 | 1% CS-6% Mannitol | 1% | 29 mM | — | 329 mM | 42.2 mM | 1 mL | 1 mL PRP |
| | 21 | 2% CS-2% Trehalose | 2% | 57 mM | 53 mM | — | 42.2 mM | 1 mL | 1 mL PRP |
| | 22 | 2% CS-6% Trehalose | 2% | 57 mM | 159 mM | — | 42.2 mM | 1 mL | 1 mL PRP |
| | 23 | 2% CS-2% Mannitol | 2% | 57 mM | — | 110 mM | 42.2 mM | 1 mL | 1 mL PRP |
| | 24 | 2% CS-6% Mannitol | 2% | 57 mM | — | 329 mM | 42.2 mM | 1 mL | 1 mL PRP |

2—Cake Appearance

Cakes were bulkiest when increased lyoprotectant concentrations were used. Cakes containing mannitol were bulkier than cakes containing trehalose.

3—Cake Reconstitution

Human PRP and PPP were extracted from 2 different human donors as described above in Example 3, Section 2-Isolation of human PRP.

Cakes were reconstituted with 1 mL PRP or 1 mL PPP and mixed with three 0.39 g steel beads for 10 seconds.

Formulations containing 2% (w/v) chitosan did not solubilise well.

Cakes containing lower $M_n$ chitosan 32 kDa were easier to reconstitute compared to cakes containing higher $M_n$ chitosan 56 kDa at both 0.56% and 1% (w/v) chitosan concentration.

angle (38 degrees) immediately after reconstitution and taking pictures at fixed times.

Increasing chitosan concentration improved paste-like properties of formulations (Compare FIGS. 5A1 & 5A2). Increasing chitosan $M_n$ improved paste-like properties of formulations (Compare FIGS. 5A1 & 5A3).

TABLE 12

Performance of the 24 different formulations.

| Criteria number | Criteria description | Performance of formulations |
|---|---|---|
| 1 | Homogenous solid form with good mechanical properties for shipping (Assessed with cake appearance) | Twenty met criteria 1 (#3-12, 15-24) |
| 2 | Rapid and complete reconstitution (Assessed with visual inspection post-mixing) | Fourteen met criteria 2 (#1-8, 13-16, 19-20) |

TABLE 12-continued

Performance of the 24 different formulations.

| Criteria number | Criteria description | Performance of formulations |
|---|---|---|
| 3 | The mixture should not inhibit coagulation (Assessed with thromboelastography) Note that #20 was not tested due to insufficient PRP extraction | Thirteen met criteria 3 (#1-8, 13-16, 19) |
| 4 | The coagulated mixtures (implants) should be mechanically stable (Assessed with manual crushing test) | Not checked |

$M_n$ 30 kDa, 81.0% DDA and $M_n$ 28 kDa, 80.5% DDA) were dissolved in HCl overnight at room temperature to obtain a final chitosan concentration of 1% (w/v). The solutions were filter-sterilised. Filter-sterilised 15% (w/v) trehalose, 15% (w/v) mannitol and 270 mM $CaCl_2$ were added, as required. Filter-sterilised Rhodamine-chitosan tracer ($M_n$ 40 kDa, 80.0% DDA or $M_n$ 110 kDa, 80.2% DDA) was added before dispensing in 3 mL individual vials for freeze-drying.

As per Table 13, the HCl concentration was adjusted so that all formulations had a HCl:glucosamine ratio of 0.6. Lyoprotectant concentration was set at 2% or 6% (w/v) enough to provide a stable cake but not impede coagulation.

The freeze-drying cycle was identical to the one described in Example 2, Section 2-Freeze-drying cycle.

TABLE 13

Formulations with $CaCl_2$ reconstituted directly with PRP

| CS | Formulation | Group | Chitosan (w/v) | HCl (mM) | Trehalose (mM) | Mannitol (mM) | $CaCl_2$ (mM) | Aliquot into | Rehydrated in |
|---|---|---|---|---|---|---|---|---|---|
| DDA 81.2% | 1 | 1% CS-2% Trehalose | 1% | 29 mM | 53 mM | — | 42.2 mM | 1 mL | 1 mL PRP |
| $M_n$ 32 kDa | 2 | 1% CS-6% Trehalose | 1% | 29 mM | 159 mM | — | 42.2 mM | 1 mL | 1 mL PRP |
|  | 3 | 1% CS-2% Mannitol | 1% | 29 mM | — | 110 mM | 42.2 mM | 1 mL | 1 mL PRP |
|  | 4 | 1% CS-6% Mannitol | 1% | 29 mM | — | 329 mM | 42.2 mM | 1 mL | 1 mL PRP |
| DDA 81.0% | 5 | 1% CS-2% Trehalose | 1% | 29 mM | 53 mM | — | 42.2 mM | 1 mL | 1 mL PRP |
| $M_n$ 30 kDa | 6 | 1% CS-6% Trehalose | 1% | 29 mM | 159 mM | — | 42.2 mM | 1 mL | 1 mL PRP |
|  | 7 | 1% CS-2% Mannitol | 1% | 29 mM | — | 110 mM | 42.2 mM | 1 mL | 1 mL PRP |
|  | 8 | 1% CS-6% Mannitol | 1% | 29 mM | — | 329 mM | 42.2 mM | 1 mL | 1 mL PRP |
| DDA 80.5% | 9 | 1% CS-2% Trehalose | 1% | 29 mM | 53 mM | — | 42.2 mM | 1 mL | 1 mL PRP |
| $M_n$ 28 kDa | 10 | 1% CS-6% Trehalose | 1% | 29 mM | 159 mM | — | 42.2 mM | 1 mL | 1 mL PRP |
|  | 11 | 1% CS-2% Mannitol | 1% | 29 mM | — | 110 mM | 42.2 mM | 1 mL | 1 mL PRP |
|  | 12 | 1% CS-6% Mannitol | 1% | 29 mM | — | 329 mM | 42.2 mM | 1 mL | 1 mL PRP |
| DDA 80.1% | 13 | 1% CS-2% Mannitol | 1% | 29 mM | — | 110 mM | 42.2 mM | 1 mL | 1 mL PRP |
| $M_n$ 56 kDa | 14 | 1% CS-6% Mannitol | 1% | 29 mM | — | 329 mM | 42.2 mM | 1 mL | 1 mL PRP |
| DDA 81.8%, | 15 | 1% CS-2% Mannitol | 1% | 29 mM | — | 110 mM | 42.2 mM | 1 mL | 1 mL PRP |
| $M_n$ 56 kDa | 16 | 1% CS-6% Mannitol | 1% | 29 mM | — | 329 mM | 42.2 mM | 1 mL | 1 mL PRP |

TABLE 12-continued

Performance of the 24 different formulations.

| Criteria number | Criteria description | Performance of formulations |
|---|---|---|
| 5 | The coagulated mixtures (implants) should largely inhibit clot retraction (Assessed with liquid expression measurements) | Fourteen met criteria 5 (#2-8, 13-19) |
| 6 | Good mixing without phase separation of the polymer and blood components (Assessed with histology) | Five met criteria 6 (#6, 7, 8, 9, 16) |
| 7 | The mixtures should have appropriate handling properties (Assessed with runniness test) | Twelve met criteria 7 (#5-8, 13-20) |
| 8 | The mixtures should have close to physiological properties (pH 6.6-7.0 and osmolality 400-600 mOsm) (Assessed with pH and osmolality measurements) | Eleven met criteria 8 (#1-3, 5-7, 13-15, 17, 19) |

In Example 5, paste-like properties of formulations can be improved by increasing chitosan concentration or chitosan $M_n$. Freeze-dried cakes containing medium molecular weight chitosan can be easily reconstituted in PRP as long as the chitosan concentration is below 2% (w/v).

Example 6

1—Preparation of Chitosan Formulations

Five different medium $M_n$ Chitosans ($M_n$ 56 kDa, 80.1% DDA, $M_n$ 56 kDa, 81.8% DDA, $M_n$ 32 kDa, 81.2% DDA,

2—Cake Appearance

Cakes were bulkiest when increased lyoprotectant concentrations were used. Cakes containing mannitol were bulkier than cakes containing trehalose (FIGS. 6A1 and 6A2).

3—Cake Reconstitution

Human PRP and PPP were extracted as described above in Example 3, Section 2-Isolation of human PRP.

Cakes were reconstituted with 1 mL PRP or 1 mL PPP and mixed with three 0.39 g steel beads for 10 seconds.

All formulations dissolved well and met performance criteria 2.

4—Thromboelastography (TEG)

360 μL of each formulation was loaded into a TEG cup immediately after mixing and TEG tracings were recorded for 1 hour.

All formulations induced a 2-phase coagulation mechanism as revealed by TEG tracings (FIGS. 6B1 and 6B2).

In all cases, adding 6% (w/v) lyoprotectant gave softer clots with lower maximal amplitude (MA between 37-67 mm) than adding 2% (w/v) lyoprotectant (MA between 68-79 mm).

5—Runniness Test

Runniness was assessed by placing a 30 μL drop of each formulation onto a rigid piece of plastic fixed at a certain angle (38 degrees) immediately after reconstitution and taking pictures at fixed times.

All formulations had paste-like properties compared to PRP alone (FIG. 6C1).

6—Liquid Expression

Formulations reconstituted in PRP were dispensed into glass tubes at 37° C. After 60 minutes, liquid expression from the hybrid clots was quantified by weight measurement.

All hybrid clots expressed less liquid than PRP alone (FIG. 6B3).

7—Clot Homogeneity

Hybrid clots were fixed in 10% NBF and thick razor blade sections were observed with epifluorescence microscopy to evaluate chitosan dispersion in the clots.

Chitosan was dispersed throughout the hybrid clots for all the formulations (FIGS. 6A3 and 6A4)

8—Crushing Test

After 1 hour of clotting, each hybrid clot was subjected to a crushing test and mechanical strength scored.

0=Clot could not be handled without disintegrating.

+=Clot was easily broken and crushed appearance was multiple fragments (more than 5 fragments).

++=Clot was relatively firm and crushed appearance was multiple fragments (3-5 fragments).

+++=Clot was firm and elastic, crushed appearance was 2-3 fragments.

++++=Clot was firm and elastic, crushed appearance was 2 fragments (sometimes still connected) or there was just a hole in the center of clot.

Adding 6% (w/v) lyoprotectant decreased clot mechanical strength compared to 2% (w/v) lyoprotectant (Compare FIGS. 6D1 and 6D2 to 6D3 and 6D4).

9—Ex Vivo Implantation in Cartilage Defects

Biopsy punches of 8 mm and flat surgical blades were used to create cartilage defects in pig condyle and trochlea.

The joints were placed in a humid chamber at 37° C. for at least 30 min before the start of the experiment.

Reconstituted freeze-dried chitosan/PRP formulations were injected into the cartilage defects.

The joints were immediately sealed in the humid chamber and were placed at 37° C. for 1 hour.

Freeze-dried chitosan/PRP formulations were successfully implanted ex vivo in cartilage defects using a syringe and 20-gauge needle where they coagulated in situ (FIG. 6C2).

TABLE 14

Performance of the 16 different formulations.

| Criteria number | Criteria description | Performance of formulations |
|---|---|---|
| 1 | Homogenous solid form with good mechanical properties for shipping (Assessed with cake appearance) | All met criteria 1 (#1-16) |
| 2 | Rapid and complete reconstitution (Assessed with visual inspection post-mixing) | All met criteria 2 (#1-16) |

TABLE 14-continued

Performance of the 16 different formulations.

| Criteria number | Criteria description | Performance of formulations |
|---|---|---|
| 3 | The mixture should not inhibit coagulation (Assessed with thromboelastography) | All met criteria 3 (#1-16) |
| 4 | The coagulated mixtures (implants) should be mechanically stable (Assessed with manual crushing test) | Eight met criteria 4 (#1, 3, 5, 7, 9, 11, 13, 15) |
| 5 | The coagulated mixtures (implants) should largely inhibit clot retraction (Assessed with liquid expression measurements) | All met criteria 5 (#1-16) |
| 6 | Good mixing without phase separation of the polymer and blood components (Assessed with histology) | Six met criteria 6 (#6, 8, 10, 12, 14, 16) |
| 7 | The mixtures should have appropriate handling properties (Assessed with runniness test) | All met criteria 7 (#1-16) |
| 8 | The mixtures should have close to physiological properties (pH 6.6-7.0 and osmolality 400-600 mOsm) (Assessed with pH and osmolality measurements) | Eleven met criteria 8 (#1-3, 5-7, 9-11, 13, 15) |

In Example 6, different batches of chitosan powder with similar $M_n$ can be used to prepare cakes that will have equivalent performance characteristics. Chitosan cakes with high concentrations of lyoprotectant produce chitosan/PRP hybrids that are undesirably soft.

Example 7

1—Preparation of Chitosan Formulations

Four different $M_n$ Chitosans ($M_n$ 10 kDa, 80.6% DDA, $M_n$ 41 kDa, 80.6% DDA, $M_n$ 89 kDa, 80.6% DDA and $M_n$ 108 kDa, 80.6% DDA) were dissolved in HCl overnight at room temperature to obtain final chitosan concentrations of 0.56% (w/v), 1% (w/v) and 2% (w/v), the latter concentration only prepared for the chitosan $M_n$ 10 kDa. The solutions were filter-sterilised. Filter-sterilised 15% (w/v) trehalose, 15% (w/v) mannitol and 270 mM $CaCl_2$ were added, as required. Filter-sterilised Rhodamine-chitosan tracer ($M_n$ 10 kDa, 81.9% DDA, $M_n$ 40 kDa, 80.0% DDA or $M_n$ 110 kDa, 80.2% DDA) was added before dispensing in 3 mL or 2 mL individual vials for freeze-drying.

As per Table 15, the HCl concentration was adjusted so that all formulations had a HCl:glucosamine ratio of 0.6. Lyoprotectant concentration was set at 2%, 4% or 6% (w/v) enough to provide a stable cake but not impede coagulation.

The freeze-drying cycle was identical to the one described in Example 2, Section 2-Freeze-drying cycle.

TABLE 15

Formulations with CaCl₂ reconstituted directly with PRP.

| CS | Sol Formulation | Chitosan (w/vol) | HCl for 60% protonated (mM) | Trehalose (mM) | Mannitol (mM) | $CaCl_2$ (mM) | Aliquot into | Rehydrated in (volume) of PRP |
|---|---|---|---|---|---|---|---|---|
| $M_n$ 10 kDa, 80.6% DDA | 1  0.56% CS-2% Trehalose | 0.56% | 16 mM | 53 mM | — | 42.2 mM | 1 mL or 300 μL | 1 mL or 300 μL |
| | 2  0.56% CS-6% Trehalose | 0.56% | 16 mM | 159 mM | — | 42.2 mM | 1 mL or 300 μL | 1 mL or 300 μL |
| | 3  0.56% CS-2% Mannitol | 0.56% | 16 mM | — | 110 mM | 42.2 mM | 1 mL or 300 μL | 1 mL or 300 μL |
| | 4  0.56% CS-6% Mannitol | 0.56% | 16 mM | — | 329 mM | 42.2 mM | 1 mL or 300 μL | 1 mL or 300 μL |
| | 5  1% CS-2% Trehalose | 1% | 29 mM | 53 mM | — | 42.2 mM | 1 mL or 300 μL | 1 mL or 300 μL |
| | 6  1% CS-6% Trehalose | 1% | 29 mM | 159 mM | — | 42.2 mM | 1 mL or 300 μL | 1 mL or 300 μL |
| | 7  1% CS-2% Mannitol | 1% | 29 mM | — | 110 mM | 42.2 mM | 1 mL or 300 μL | 1 mL or 300 μL |
| | 8  1% CS-6% Mannitol | 1% | 29 mM | — | 329 mM | 42.2 mM | 1 mL or 300 μL | 1 mL or 300 μL |
| | 9  2% CS-2% Trehalose | 2% | 57 mM | 53 mM | — | 42.2 mM | 1 mL or 300 μL | 1 mL or 300 μL |
| | 10  2% CS-6% Trehalose | 2% | 57 mM | 159 mM | — | 42.2 mM | 1 mL or 300 μL | 1 mL or 300 μL |
| | 11  2% CS-2% Mannitol | 2% | 57 mM | — | 110 mM | 42.2 mM | 1 mL or 300 μL | 1 mL or 300 μL |
| | 12  2% CS-6% Mannitol | 2% | 57 mM | — | 329 mM | 42.2 mM | 1 mL or 300 μL | 1 mL or 300 μL |
| $M_n$ 41 kDa, 80.6% DDA | 13  0.56% CS-2% Trehalose | 0.56% | 16 mM | 53 mM | — | 42.2 mM | 1 mL or 300 μL | 1 mL or 300 μL |
| | 14  0.56% CS-6% Trehalose | 0.56% | 16 mM | 159 mM | — | 42.2 mM | 1 mL or 300 μL | 1 mL or 300 μL |
| | 15  0.56% CS-2% Mannitol | 0.56% | 16 mM | — | 110 mM | 42.2 mM | 1 mL or 300 μL | 1 mL or 300 μL |
| | 16  0.56% CS-6% Mannitol | 0.56% | 16 mM | — | 329 mM | 42.2 mM | 1 mL or 300 μL | 1 mL or 300 μL |
| | 17  1% CS-2% Trehalose | 1% | 29 mM | 53 mM | — | 42.2 mM | 1 mL or 300 μL | 1 mL or 300 μL |
| | 18  1% CS-6% Trehalose | 1% | 29 mM | 159 mM | — | 42.2 mM | 1 mL or 300 μL | 1 mL or 300 μL |
| | 19  1% CS-2% Mannitol | 1% | 29 mM | — | 110 mM | 42.2 mM | 1 mL or 300 μL | 1 mL or 300 μL |
| | 20  1% CS-6% Mannitol | 1% | 29 mM | — | 329 mM | 42.2 mM | 1 mL or 300 μL | 1 mL or 300 μL |
| $M_n$ 89 kDa, 80.6% DDA | 21  0.56% CS-2% Trehalose | 0.56% | 16 mM | 53 mM | — | 42.2 mM | 1 mL or 300 μL | 1 mL or 300 μL |
| | 22  0.56% CS-6% Trehalose | 0.56% | 16 mM | 159 mM | — | 42.2 mM | 1 mL or 300 μL | 1 mL or 300 μL |
| | 23  0.56% CS-2% Mannitol | 0.56% | 16 mM | — | 110 mM | 42.2 mM | 1 mL or 300 μL | 1 mL or 300 μL |
| | 24  0.56% CS-6% Mannitol | 0.56% | 16 mM | — | 329 mM | 42.2 mM | 1 mL or 300 μL | 1 mL or 300 μL |
| $M_n$ 108 kDa, 80.6% DDA | 25  1% CS-2% Trehalose | 1% | 29 mM | 53 mM | — | 42.2 mM | 1 mL or 300 μL | 1 mL or 300 μL |
| | 26  1% CS-6% Trehalose | 1% | 29 mM | 159 mM | — | 42.2 mM | 1 mL or 300 μL | 1 mL or 300 μL |
| | 27  1% CS-2% Mannitol | 1% | 29 mM | — | 110 mM | 42.2 mM | 1 mL or 300 μL | 1 mL or 300 μL |
| | 28  1% CS-6% Mannitol | 1% | 29 mM | — | 329 mM | 42.2 mM | 1 mL or 300 μL | 1 mL or 300 μL |
| $M_n$ 10 kDa, 80.6% DDA | 29  0.56% CS-4% Trehalose | 0.56% | 16 mM | 106 mM | — | 42.2 mM | 1 mL or 300 μL | 1 mL or 300 μL |
| | 30  0.56% CS-4% Mannitol | 0.56% | 16 mM | — | 220 mM | 42.2 mM | 1 mL or 300 μL | 1 mL or 300 μL |
| | 31  1% CS-4% Trehalose | 1% | 29 mM | 106 mM | — | 42.2 mM | 1 mL or 300 μL | 1 mL or 300 μL |
| | 32  1% CS-4% Mannitol | 1% | 29 mM | — | 220 mM | 42.2 mM | 1 mL or 300 μL | 1 mL or 300 μL |
| $M_n$ 41 kDa, 80.6% DDA | 33  0.56% CS-4% Trehalose | 0.56% | 16 mM | 106 mM | — | 42.2 mM | 1 mL or 300 μL | 1 mL or 300 μL |
| | 34  0.56% CS-4% Mannitol | 0.56% | 16 mM | — | 220 mM | 42.2 mM | 1 mL or 300 μL | 1 mL or 300 μL |
| | 35  1% CS-4% Trehalose | 1% | 29 mM | 106 mM | — | 42.2 mM | 1 mL or 300 μL | 1 mL or 300 μL |
| | 36  1% CS-4% Mannitol | 1% | 29 mM | — | 220 mM | 42.2 mM | 1 mL or 300 μL | 1 mL or 300 μL |
| $M_n$ 89 kDa, 80.6% DDA | 37  0.56% CS-4% Trehalose | 0.56% | 16 mM | 106 mM | — | 42.2 mM | 1 mL or 300 μL | 1 mL or 300 μL |
| | 38  0.56% CS-4% Mannitol | 0.56% | 16 mM | — | 220 mM | 42.2 mM | 1 mL or 300 μL | 1 mL or 300 μL |
| | 39  1% CS-4% Trehalose | 1% | 29 mM | 106 mM | — | 42.2 mM | 1 mL or 300 μL | 1 mL or 300 μL |
| | 40  1% CS-4% Mannitol | 1% | 29 mM | — | 220 mM | 42.2 mM | 1 mL or 300 μL | 1 mL or 300 μL |

2—Cake Appearance

Cakes were bulkiest when increased lyoprotectant concentrations were used. Cakes containing mannitol were bulkier than cakes containing trehalose.

3—Cake Reconstitution

Human PRP and PPP were extracted as described above in Example 3, Section 2-Isolation of human PRP.

Cakes were reconstituted with 1 mL PRP or 1 mL PPP and mixed by hand without the aid steel beads for 10 seconds. For four of the formulations (#15, 19, 23, 27), three 0.39 g steel beads were used to reconstitute the cakes as well to compare with previously obtained results.

The formulations prepared with chitosan $M_n$ 10 kDa at 0.56% (w/v) and at 1% (w/vol) dissolved completely. Formulations prepared with chitosan $M_n$ 10 kDa at 2% (w/vol) and with chitosan $M_n$ 41 kDa at 0.56% and 1% (w/vol) dissolved well. Formulations prepared with chitosan $M_n$ 89 kDa and 108 kDa were thicker and more difficult to handle.

4—Thromboelastography (TEG)

360 μL of each formulation was loaded into a TEG cup immediately after mixing and TEG tracings were recorded for 1 hour.

Formulations containing chitosan $M_n$ 10 kDa at 0.56% (w/v) induced a 1-phase coagulation tracing. Increasing chitosan concentration and $M_n$ induced a 2-phase coagulation mechanism as revealed by TEG tracings.

Clot reaction time was high for formulations containing chitosan $M_n$ 10 kDa and short for formulations containing chitosan $M_n$ 108 kDa, with the 40 kDa formulations falling in between.

Maximal amplitude was greater for hybrid clots containing 2% (w/v) lyoprotectant compared to hybrid clots containing 4% or 6% (w/v) lyoprotectant.

5—Runniness Test

Runniness was assessed by placing a 30 μL drop of each formulation onto a rigid piece of plastic fixed at a certain angle (38 degrees) immediately after reconstitution and taking pictures at fixed times.

The formulations containing chitosan $M_n$ 10 kDa at 0.56% (w/vol) and 1% (w/vol) were runny.

All other formulations had paste-like properties compared to PRP alone.

6—Liquid Expression

Formulations reconstituted in PRP were dispensed into glass tubes at 37° C. After 60 minutes, liquid expression from the hybrid clots was quantified by weight measurement.

All hybrid clots expressed less liquid than PRP alone.

7—Clot Homogeneity

Large chitosan aggregates were observed in most hybrid clots prepared with chitosan $M_n$ 89 kDa and 108 kDa (FIGS. 7A3, 7A4, 7A7 and 7A8). Chitosan was well dispersed within most hybrid clots when chitosan $M_n$ 41 kDa was used (FIGS. 7A1, 7A2, 7A5 and 7A6). Erythrocytes present in the PRP sedimented towards the bottom of the clots leaving a band of chitosan at the surface of the clot when the chitosan $M_n$ 10 kDa was used.

8—Crushing Test

After 1 hour of clotting, each hybrid clot was subjected to a crushing test and mechanical strength scored.

0=Clot could not be handled without disintegrating.

+=Clot was easily broken and crushed appearance was multiple fragments (more than 5 fragments).

++=Clot was relatively firm and crushed appearance was multiple fragments (3-5 fragments).

+++=Clot was firm and elastic, crushed appearance was 2-3 fragments.

++++=Clot was firm and elastic, crushed appearance was 2 fragments (sometimes still connected) or there was just a hole in the center of clot.

Adding 6% (w/v) lyoprotectant decreased clot mechanical strength.

9—Ex Vivo Implantation in Cartilage Defects

Biopsy punches of 8 mm and flat surgical blades were used to create cartilage defects in pig condyle, trochlea and tibial plateau.

The joints were placed in a humid chamber at 37° C. for at least 30 min before the start of the experiment.

Reconstituted freeze-dried chitosan/PRP formulations were injected into the cartilage defects.

The joints were immediately sealed in the humid chamber and were placed at 37° C. for 1 hour.

Freeze-dried chitosan/PRP formulations were successfully implanted ex vivo in cartilage defects using a syringe and 20-gauge needle where they coagulated in situ.

10—Reconstituting the Freeze-Dried Formulations without Beads Versus Mixing with Beads Histological appearance of hybrid clots was similar whether the freeze-dried cakes were reconstituted without the aid of stainless steel beads or by mixing with three 0.39 g stainless steel beads (compare FIGS. 7A1, 7A2, 7A3 and 7A4 with 7A5, 7A6, 7A7 and 7A8).

Performance characteristics of freeze-dried formulations were similar for hybrid clots prepared without the aid the without the aid of stainless steel beads or by mixing with three 0.39 g stainless steel beads (see Table of FIG. 7B).

11—Osmolality of Formulations Reconstituted with PRP

Freeze-dried chitosan formulations containing mannitol had higher osmolality than freeze-dried formulations containing trehalose. Osmololality increased with lyoprotectant concentration. Formulations containing 2% (w/vol) trehalose had osmolality between 443-495 mOsm. Formulations containing 2% (w/vol) mannitol had osmolality between 526-582 mOsm. Formulations containing 4% (w/vol) trehalose had osmolality between 516-564 mOsm. Formulations containing 4% (w/vol) mannitol had osmolality between 608-665 mOsm. Formulations containing 6% (w/vol) trehalose had osmolality between 595-631 mOsm. Formulations containing 6% (w/vol) mannitol had osmolality between 759-823 mOsm.

12—Subcutaneous Implantation of Freeze-Dried Chitosan Formulations

Several formulations with low and high osmolality were tested in vivo in a rabbit subcutaneous implant model (Table 16).

TABLE 16

Formulations tested in vivo in a rabbit subcutaneous implant model.

| No | Formulation | CS DDA[1] | CS $M_n$ | CS $M_w$ | CS PD | CS conc | HCl conc | Trehalose conc | Mannitol conc | CaCl$_2$ conc | pH[3] | mOsm[3] |
|---|---|---|---|---|---|---|---|---|---|---|---|---|
| 13 | 0.56% CS-2% Trehalose | 80.6% | 41 kDa | 75 kDa | 1.837 | 0.56% | 16 mM | 53 mM | — | 42.2 mM | 6.913 | 477 |
| 33 | 0.56% CS-4% Trehalose | 80.6% | 41 kDa | 75 kDa | 1.837 | 0.56% | 16 mM | 106 mM | — | 42.2 mM | 6.995 | 564 |
| 14 | 0.56% CS-6% Trehalose | 80.6% | 41 kDa | 75 kDa | 1.837 | 0.56% | 16 mM | 159 mM | — | 42.2 mM | 6.962 | 593 |
| 17 | 1% CS-2% Trehalose | 80.6% | 41 kDa | 75 kDa | 1.837 | 1% | 29 mM | 53 mM | — | 42.2 mM | 6.870 | 483 |
| 35 | 1% CS-4% Trehalose | 80.6% | 41 kDa | 75 kDa | 1.837 | 1% | 29 mM | 106 mM | — | 42.2 mM | 6.794 | 527 |
| 18 | 1% CS-6% Trehalose | 80.6% | 41 kDa | 75 kDa | 1.837 | 1% | 29 mM | 159 mM | — | 42.2 mM | 6.861 | 628 |
| 21 | 0.56% CS-2% Trehalose | 80.6% | 89 kDa | 156 kDa | 1.757 | 0.56% | 16 mM | 53 mM | — | 42.2 mM | 6.970 | 461 |
| 22 | 0.56% CS-6% Trehalose | 80.6% | 89 kDa | 156 kDa | 1.757 | 0.56% | 16 mM | 159 mM | — | 42.2 mM | 6.950 | 629 |
| 25 | 1% CS-2% Trehalose | 80.6% | 108 kDa | 173 kDa | 1.544 | 1% | 29 mM | 53 mM | — | 42.2 mM | 6.957 | 443 |
| 27[1] | 1% CS-2% Mannitol | 80.6% | 108 kDa | 173 kDa | 1.544 | 1% | 29 mM | — | 110 mM | 42.2 mM | 6.915 | 582 |

[1]DDA of source chitosan depolymerised to $M_n$ 41, 89 and 108 kDa.
[2] Note that formulation #27 was chosen because there were no mores cakes available containing the formulation 1% CS ($M_n$ 108 kDa) with 6% Trehalose.
[3]pH and osmolality values obtained after reconstitution in human PRP.

The hair on the back of NZW rabbits was shaved and the skin was disinfected with 3 passages of Baxedin®, then with 3 alternating passages of proviodine and isopropanol 70%.

Autologous PRP was prepared from rabbit blood extracted immediately prior to surgery, as described above in Example 1 section 4—Isolation of rabbit PRP. Each 300 µL freeze-dried chitosan cake was reconstituted with 300 μL PRP without the aid of beads for mixing.

A 1-cc syringe equipped with a Sub Q needle was used to deliver 150 μL of each implant under the skin of the back of the rabbit PRP controls were recalcified with 42.2 mM $CaCl_2$ prior to injection.

The injection sites were systematically varied on each animal to avoid site-dependent outcomes.

Animals were euthanized at 1 (FIGS. 7C1 to 7C6), 3 (FIGS. 7D1 to 7D6), 7 and 14 days post-injection (FIGS. 7E2 and 7E3).

At day 1, the chitosan implants appeared largely intact. In some instances the erythrocytes present in the PRP were visible within the implants. White blood cells were attracted to the implants and were found mostly at the periphery of the implants (FIGS. 7C1, 7C2, 7C3 and 7C4).

By day 3, the chitosan/PRP implants were partly degraded and white blood cells were invading the implants (FIGS. 7D1, 7D2, 7D3 and 7D4).

There was an effect of time as white blood cell recruitment was increased at day 3 compared to day 1 (Compare FIGS. 7D1-7D4 to FIGS. 7C1-7C4).

The chitosan/PRP hybrids were resident in vivo until 14 days post-injection (FIGS. 7E1, 7E2 and 7E3).

The recalcified PRP controls were only visible until 3 days post-injection (FIG. 7E4 shows PRP control at 1 day) and did not induce much cell recruitment (FIGS. 7C5, 7C6, 7D5, 7D6 and 7E4).

TABLE 17

Performance of the 40 different formulations.

| Criteria number | Criteria description | Performance of formulations |
|---|---|---|
| 1 | Homogenous solid form with good mechanical properties for shipping (Assessed with cake appearance) | All met criteria 1 |
| 2 | Rapid and complete reconstitution (Assessed with visual inspection post-mixing) | 30 met criteria 2 (#1-20; 29-38) |
| 3 | The mixture should not inhibit coagulation (Assessed with thromboelastography) | All met criteria 3 |
| 4 | The coagulated mixtures (implants) should be mechanically stable (Assessed with manual crushing test) | 27 met criteria 4 |

TABLE 17-continued

Performance of the 40 different formulations.

| Criteria number | Criteria description | Performance of formulations |
|---|---|---|
| 5 | The coagulated mixtures (implants) should largely inhibit clot retraction (Assessed with liquid expression measurements) | All met criteria 5 |
| 6 | Good mixing without phase separation of the polymer and blood components (Assessed with histology) | 12 met criteria 6 (#13-20; 35-38) |
| 7 | The mixtures should have appropriate handling properties (Assessed with runniness test) | All met criteria 7 |
| 8 | The mixtures should have close to physiological properties (pH 6.6-7.0 and osmolality 400-600 mOsm) (Assessed with pH and osmolality measurements) | Seven did not meet criteria 8 (#4, 8, 12, 16, 20, 24, 27) |

In Example 7, mixing with stainless steel beads is not required for reconstitution of freeze-dried chitosan cakes with PRP. Formulations containing high concentrations of lyoprotectant have high osmolality and attract more leukocytes upon implantation in vivo. Chitosan/PRP hybrids were also found to be retained longer than recalcified PRP only controls in vivo. 8 specific formulations (#13, 15, 17, 19, 35-38) met all of the pre-defined performance characteristics.

Example 8

1—Preparation of Chitosan Formulations

Two different Chitosans ($M_n$ 43 kDa, 85% DDA and $M_n$ 36 kDa, 80% DDA) were dissolved in HCl overnight at room temperature to obtain final chitosan concentrations of 1% (w/v). The solutions were filter-sterilised. Filter-sterilised 15% (w/v) trehalose and 270 mM $CaCl_2$ were added, as required. Filter-sterilised Rhodamine-chitosan tracer ($M_n$ 40 kDa, 80.0% DDA) was added to some of the vials before dispensing in 3 mL individual vials for freeze-drying.

As per Table 18, the HCl concentration was adjusted so that all formulations had a HCl:glucosamine ratio of 0.6. Lyoprotectant concentration was set at 1% (w/v) in order to have osmolality close to physiological, provide a stable cake but not impede coagulation.

The freeze-drying cycle was identical to the one described in Example 2, Section 2-Freeze-drying cycle.

TABLE 18

Formulations with $CaCl_2$ reconstituted directly with PRP.

| Sol | CS Mn | CS DDA | Formulation | Chitosan (w/vol) | HCl for 60% protonated (mM) | Trehalose (mM) | Mannitol (mM) | $CaCl_2$ (mM) | Aliquot into | Rehydrated in (volume) of PRP |
|---|---|---|---|---|---|---|---|---|---|---|
| 1 | 43 kDa | 85% | 1% CS-1% Trehalose | 1% | 31 mM | 26 mM | — | 42.2 mM | 1 mL | 1 mL |
| 2 | 36 kDa | 80% | 1% CS-1% Trehalose | 1% | 28 mM | 26 mM | — | 42.2 mM | 1 mL | 1 mL |

2—Cake Appearance

Cakes had a smooth surface and nice appearance without any collapse. There was a slight retraction of all the cakes in the glass vials upon freeze-drying (FIGS. 8A1 and 8A2).

3—Cake Reconstitution

Human PRP and PPP were extracted as described above in Example 3, Section 2-Isolation of human PRP.

Cakes were reconstituted with 1 mL PRP or 1 mL PPP and mixed by hand without the aid steel beads for 10 seconds.

The formulations had good solubility and dissolved completely (FIGS. 8A3 and 8A4).

4—Thromboelastography (TEG)

360 µL of each formulation was loaded into a TEG cup immediately after mixing and TEG tracings were recorded for 1 hour.

Clot reaction time and maximal amplitude were lower for chitosan/PRP formulations compared to the PRP control (FIGS. 8C1 and 8C2).

5—Runniness Test

Runniness was assessed by placing a 30 µL drop of each formulation onto a rigid piece of plastic fixed at a certain angle (38 degrees) immediately after reconstitution and taking pictures at fixed times.

Formulations had paste-like properties compared to PRP control.

6—Liquid Expression

Formulations reconstituted in PRP were dispensed into glass tubes at 37° C. After 60 minutes, liquid expression from the hybrid clots was quantified by weight measurement.

Hybrid clots expressed no liquid while PRP controls expressed more than 80% of their weight in serum (FIGS. 8B1, 8B2, 8B3 and 8B4).

7—Clot Homogeneity

Hybrid clots were fixed in 10% NBF and chitosan dispersion observed using epifluorescent microscopy.

Chitosan was well dispersed within the hybrid clots (FIGS. 8C3 and 8C4).

8—Crushing Test

After 1 hour of clotting, each hybrid clot was subjected to a crushing test and mechanical strength scored as described in Example 7, Section 8-Crushing test.

Hybrid clots had good mechanical strength.

11—Osmolality of Formulations Reconstituted with PRP

The formulation containing Chitosan $M_n$ 43 kDa, 85% DDA had osmolality of 457 mOsm upon reconstitution. The formulation containing Chitosan $M_n$ 36 kDa, 80% DDA had osmolality of 444 mOsm upon reconstitution.

12—In Vivo Implantation in Meniscus Defects

The two above described formulations as well as PRP-only controls were tested in a sheep meniscus repair model.

On the morning of surgery, PRP was extracted from the sheep blood as described in Example 2, Section 4-Isolation of sheep PRP.

A 1.5 cm long arthrotomy was made to access the medial femorotibial joint space and a horizontal incision was made in the medial joint capsule to access the anterior $\frac{1}{3}^{rd}$ of the meniscus.

A 10 mm tear was created at $\frac{1}{3}^{rd}$ the length between the capsular and free borders (closer to the capsule) using a #11 scalpel blade to create a stab wound (FIG. 8D1) which was lengthened by a meniscus push knife (FIG. 8D2).

The tear and synovium were rasped to create some 3D space for the FD chitosan/PRP implant to adhere to without disrupting circumferential fibres that impart hoop strains (FIG. 8D3).

Two 3-0 polypropylene sutures were placed in a horizontal mattress pattern around the meniscus tear (FIG. 8D4).

Two trephination channels were created from the periphery of the meniscus to the tear with by placing two 18 gauge needles ~2 mm apart (FIG. 8D5).

The chitosan cakes were reconstituted with 1 mL of autologous PRP and mixed vigorously for 10 seconds.

The chitosan/PRP mixture was aspirated using a 1-cc syringe.

The chitosan/PRP hybrid material was extruded into the channels and into the tear while pulling out the 18 gauge needles (FIG. 8D6).

The sutures were tightened 5 minutes after delivery with sufficient tension to appose the meniscal tear edges.

The joint capsule was sutured and the procedure repeated with the other knee as per study design.

The PRP-only controls were recalcified with 42.2 mM $CaCl_2$ immediately prior to injection.

Animals were euthanized at 1 and 21 days post-injection surgery.

At day 1, chitosan/PRP was resident in the tears (FIGS. 8E1 and 8E2).

At day 21, the edges of the tears treated with chitosan/PRP were well apposed (FIGS. 8E3 and 8E4).

Example 8, exhibited that chitosan/PRP formulations may be injected into meniscus defects in vivo using standard surgical instrumentation, that chitosan/PRP hybrids are resident in the meniscus tears and that tears treated with chitosan/PRP hybrids have well apposed edges after 21 days of healing.

Example 9

1—Preparation of Chitosan Formulation

Chitosan ($M_n$ 40 kDa, 80% DDA) was dissolved in HCl overnight at room temperature to obtain final chitosan concentrations of 1% (w/v). The solution was filter-sterilised. Filter-sterilised 15% (w/v) trehalose and 270 mM $CaCl_2$ were added, as required. Filter-sterilised Rhodamine-chitosan tracer ($M_n$ 40 kDa, 80.0% DDA) was added to the vials before dispensing in 2 mL individual vials for freeze-drying.

As per Table 19, the HCl concentration was adjusted so that the formulations had a HCl:glucosamine ratio of 0.6. Lyoprotectant concentration was set at 2% (w/v).

The freeze-drying cycle was identical to the one described in Example 2, Section 2-Freeze-drying cycle.

TABLE 19

Formulation with CaCl₂ reconstituted directly with PRP.

| Sol | CS Mn | CS DDA | Formulation | Chitosan (w/vol) | HCl for 60% protonated (mM) | Trehalose (mM) | Mannitol (mM) | CaCl₂ (mM) | Aliquot into | Rehydrated in (volume) of PRP |
|---|---|---|---|---|---|---|---|---|---|---|
| 1 | 40 kDa | 80% | 1% CS-2% Trehalose | 1% | 28 mM | 53 mM | — | 42.2 mM | 300 µL | 300 µL |

8—In Vivo Chronic Cartilage Repair Model

Chondral-only defects of 4 mm×4 mm were created bi-laterally in the trochlea of three 9-month old NZW rabbits (FIG. 9A1), the knees sutured and the defects were allowed to develop to chronic stage for 1 month (FIG. 9A2).

The knees were reopened, the defects debrided and four microdrill holes were pierced through the subchondral bone with a 0.9 mm drill bit to a depth of ~4 mm.

Autologous PRP was prepared from rabbit blood extracted immediately prior to surgery, as described above in Example 1, section 4—Isolation of rabbit PRP. After creation of the defect, the freeze-dried chitosan cake was reconstituted with 300 µL PRP, mixed vigorously for 10 seconds and the implant (1 hanging drop) was delivered over the defect site and allowed to solidify in situ for ~5 min before closing the knee (FIG. 9A4).

Recalcified PRP was delivered to the contralateral knee as control (FIG. 9A3).

At 21 days post-surgery, the repair tissues on the treated and control sides had a different appearance (FIGS. 9B1 and 9B2).

Increased cell recruitment and extensive bone remodeling were observed in the chitosan/PRP treated knee (FIG. 9B4), which was absent in the control knee (FIG. 9B3).

Example 9, provided that chitosan/PRP hybrid implants may be delivered in vivo to chronic cartilage defects, where they stimulate cell recruitment and bone remodeling, features previously associated with improved repair.

Based on the above, we were able to determine which chitosan compositions fulfilled at least one, in some instances more than one, and in some instances all of our pre-defined performance characteristics. The criteria that were met include: 1) Mechanically stable cakes for storage and shipping (FIGS. 6A1 and 6A2); 2) Rapid, easy and complete reconstitution in PRP (FIGS. 6A1 and 6A2); 3) In situ coagulation achieved and not inhibited (FIGS. 6B1 and 6B2); 4) Chitosan/PRP hybrid implants able to withstand mechanical loading post-implantation (FIGS. 6D1 and 6D2); 5) Inhibition of platelet-mediated clot retraction to fill tissue defects (FIG. 6B3); 6) Good mixing without phase separation of polymers and blood components (FIGS. 6A3 and 6A4); 7) Viscous and paste-like formulations for tissue repair applications (FIG. 6C1) and 8) Close-to-physiological properties for in vivo application (Example 7). Chitosan/PRP hybrids are resident for at least 14 days in order to successfully stimulate tissue repair in vivo in contrast recalcified PRP only which was cleared within 3 days (FIGS. 7C, 7D and 7E). In addition, chitosan/PRP hybrids were used in vivo in animal models to treat meniscus defects (FIGS. 8D and 8E), acute cartilage defects (FIG. 1B) and chronic cartilage defects (FIGS. 9A and 9B). Examples of preferred embodiments for tissue implantation and in situ gelation are: 1) Chitosan of a molecular weight between about $M_n$ 28 and about 56 kDa at a concentration of no more than about 1% (w/v) and no more than about 4% (w/v) lyoprotectant or 2) Chitosan of a molecular weight between about $M_n$ 89 and about 108 kDa at a concentration no more than about 0.56% (w/v) and no more than about 4% (w/v) lyoprotectant. Other formulations tested that met some of the pre-defined criteria contained chitosan of a molecular weight between about $M_n$ 4 and about 211 kDa at a concentration range of about 0.42 and about 2% (w/v), between about 1 to about 10% lyoprotectant (sucrose, trehalose, mannitol), a salt (NaCl) or a buffer (histidine).

The scope of the claims should not be limited by the preferred embodiments set forth in the examples, but should be given the broadest interpretation consistent with the description as a whole.

What is claimed is:

1. A freeze-dried homogeneous solid cake comprising chitosan having a molecular weight number of from about 4 kDa to about 250 kDa and a degree of deacetylation of from about 80% to about 85%, a clot activator present in an amount between 42.2 and 45 mM, and at least one lyoprotectant, wherein said composition is without glycerol phosphate and said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution forming an injectable solution which upon injection:
   i) into tissue solidifies forming an implant for tissue repair; or
   ii) into an articular joint mixes with intra-articular fluids.

2. The freeze-dried homogeneous solid cake of claim 1 wherein the at least one lyoprotectant is selected from the group consisting of monosaccharide, polyol, disaccharide, trisaccharide, oligosaccharide/polysaccharide, high molecular weight excipient, amino acid, protein and a combination thereof.

3. The freeze-dried homogeneous solid cake of claim 1 wherein the chitosan has a molecular weight number from about 20 to about 250 kDa.

4. The freeze-dried homogeneous solid cake of claim 1 wherein the chitosan is present from about 0.25% to about 10% w/v.

5. The freeze-dried homogeneous solid cake of claim 1 wherein the at least one lyoprotectant is present from about 0.1% to about 30% w/v.

6. The freeze-dried homogeneous solid cake of claim 1 wherein the clot activator is selected from the group consisting of calcium chloride, calcium gluconate, calcium acetate, calcium carbonate, calcium glubionate, calcium gluceptate, calcium lactate, calcium lactobionate, calcium phosphate and combinations thereof.

7. The freeze-dried homogenous solid cake of claim 1 wherein said freeze-dried homogenous solid cake is soluble in said blood or blood product in 5 minutes or less.

8. A freeze-dried homogeneous solid cake consisting of: chitosan at a concentration of no more than about 1% (w/v), having a molecular weight in the range of about $M_n$ 28 to about 56 kDa and at least one lyoprotectant at a concentration of no more than about 4% (w/v), wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution.

9. The freeze-dried homogeneous solid cake of claim 8 wherein said composition is without glycerol phosphate.

10. The freeze-dried homogeneous solid cake of claim 8 wherein said freeze-dried homogenous solid cake is soluble in said blood or blood product in 5 minutes or less.

11. A freeze-dried homogeneous solid cake consisting of: chitosan at a concentration of no more than about 0.56% (w/v), having a molecular weight in the range of about $M_n$ 89 to about 108 kDa and at least one lyoprotectant at a concentration of no more than about 4% (w/v), wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution.

12. The freeze-dried homogeneous solid cake of claim 11 wherein said composition is without glycerol phosphate.

13. The freeze-dried homogeneous solid cake of claim 11 wherein said freeze-dried homogenous solid cake is soluble in said blood or blood product in 5 minutes or less.

14. A freeze-dried homogeneous solid cake comprising: chitosan at a concentration range of about 0.42 and about 2% (w/v), having a molecular weight range of about $M_n$ 4 to about 211 kDa and a degree of deacetylation of from about 80% to about 85%, at least one lyoprotectant at a concentration range between about 1 and about 10%, and a salt or a buffer, and being without glycerol phosphate, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution, wherein said salt is a clot activator present in an amount from about 42.2 to 45 mM.

15. The freeze-dried homogeneous solid cake of claim 14 wherein said freeze-dried homogenous solid cake is soluble in said blood or blood product in 5 minutes or less.

16. A freeze-dried homogeneous solid cake comprising chitosan having a molecular weight number of from about 4 kDa to about 250 kDa and a degree of deacetylation of from about 80% to about 85% and at least one lyoprotectant, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution forming an injectable solution, exhibiting at least one of the following:
   i) in situ coagulation achieved and not inhibited;
   ii) able to withstand mechanical loading post-implantation;
   iii) inhibition of platelet-mediated clot retraction to fill tissue defects;
   iv) good mixing without phase separation of polymers and PRP, blood product and combinations thereof;
   v) viscous and paste-like formulations for tissue repair applications;
   vi) close-to-physiological properties for in vivo application; and combinations thereof, wherein said freeze-dried homogenous solid cake further comprises a clot activator present in an amount from about 42.2 to 45 mM.

17. The freeze-dried homogeneous solid cake of claim 16 wherein said freeze-dried homogenous solid cake is soluble in said blood or blood product in 5 minutes or less.

18. A freeze-dried homogeneous solid cake consisting of: chitosan at a concentration range of about 0.42 and about 2% (w/v), having a molecular weight range of about $M_n$ 4 to about 211 kDa and a degree of deacetylation of from about 80% to about 85%, at least one lyoprotectant at a concentration range between about 1 and about 10%, and a salt or a buffer, and being without glycerol phosphate, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution.

19. The freeze-dried homogeneous solid cake of claim 18 wherein said freeze-dried homogenous solid cake is soluble in said blood or blood product in 5 minutes or less.

20. A freeze-dried homogeneous solid cake consisting of chitosan having a molecular weight number of from about 4 kDa to about 250 kDa and a degree of deacetylation of from about 80% to about 85% and at least one lyoprotectant, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution forming an injectable solution, exhibiting at least one of the following:
   i) in situ coagulation achieved and not inhibited;
   ii) able to withstand mechanical loading post-implantation;
   iii) inhibition of platelet-mediated clot retraction to fill tissue defects;
   iv) good mixing without phase separation of polymers and PRP, blood product and combinations thereof;
   v) viscous and paste-like formulations for tissue repair applications;
   vi) close-to-physiological properties for in vivo application; and combinations thereof.

21. The freeze-dried homogeneous solid cake of claim 20 wherein said freeze-dried homogenous solid cake is soluble in said blood or blood product in 5 minutes or less.

22. A freeze-dried homogeneous solid cake consisting of: chitosan at a concentration of no more than about 1% (w/v), having a molecular weight in the range of about $M_n$ 28 to about 56 kDa, at least one lyoprotectant at a concentration of no more than about 4% (w/v), and a clot activator present from about 42.2 to 45 mM, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution.

23. A freeze-dried homogeneous solid cake consisting of: chitosan at a concentration of no more than about 0.56% (w/v), having a molecular weight in the range of about $M_n$ 89 to about 108 kDa and at least one lyoprotectant at a concentration of no more than about 4% (w/v), a clot activator present from about 42.2 to 45 mM, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution.

24. A freeze-dried homogeneous solid cake consisting of: chitosan at a concentration range of about 0.42 and about 2% (w/v), having a molecular weight range of about $M_n$ 4 to about 211 kDa and a degree of deacetylation of from about 80% to about 85%, at least one lyoprotectant at a concentration range between about 1 and about 10%, and a salt or a buffer, and being without glycerol phosphate, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution, wherein said salt is a clot activator present from about 42.2 to 45 mM.

25. A freeze-dried homogeneous solid cake consisting of chitosan having a molecular weight number of from about 4 kDa to about 250 kDa and a degree of deacetylation of from about 80% to about 85% and at least one lyoprotectant, a clot activator present from about 42.2 to 45 mM, wherein said freeze-dried homogeneous solid cake is soluble in blood or a blood product selected from the group consisting of platelet rich plasma (PRP), platelet-poor plasma (PPP), autologous conditioned plasma, platelet suspension, platelet lysate and combinations thereof for reconstitution of an injectable solution forming an injectable solution, exhibiting at least one of the following:
    i) in situ coagulation achieved and not inhibited;
    ii) able to withstand mechanical loading post-implantation;
    iii) inhibition of platelet-mediated clot retraction to fill tissue defects;
    iv) good mixing without phase separation of polymers and PRP, blood product and combinations thereof;
    v) viscous and paste-like formulations for tissue repair applications;
close-to-physiological properties for in vivo application; and combinations thereof.

* * * * *

UNITED STATES PATENT AND TRADEMARK OFFICE
CERTIFICATE OF CORRECTION

PATENT NO. : 11,285,100 B2
APPLICATION NO. : 15/119397
DATED : March 29, 2022
INVENTOR(S) : Anik Chevrier et al.

It is certified that error appears in the above-identified patent and that said Letters Patent is hereby corrected as shown below:

In the Claims

Column 52, Line 29, Claim 1 replace "composition" with "freeze-dried homogeneous solid cake"

Column 53, Line 9, Claim 9 replace "composition" with "freeze-dried homogeneous solid cake"

Column 53, Line 26, Claim 12 replace "composition" with "freeze-dried homogeneous solid cake"

Signed and Sealed this
Seventh Day of June, 2022

Katherine Kelly Vidal
*Director of the United States Patent and Trademark Office*